(12) United States Patent
Coburn et al.

(10) Patent No.: US 10,745,377 B2
(45) Date of Patent: Aug. 18, 2020

(54) PIPERIDINE OR PIPERAZINE LINKED IMIDAZOLE AND TRIAZOLE DERIVATIVES AND METHODS OF USE

(71) Applicants: MERCK SHARP & DOHME CORP., Rahway, NJ (US); Craig A. Coburn, Novato, CA (US); Milana M. Maletic, Summit, NJ (US); Yunfu Luo, Shanghai (CN); Zhiqi Qi, Shanghai (CN); Tingting Yu, Shanghai (CN); Richard Soll, Shanghai (CN)

(72) Inventors: Craig A. Coburn, Novato, CA (US); Milana M. Maletic, Summit, NJ (US); Yunfu Luo, Shanghai (CN); Zhiqi Qi, Shanghai (CN); Tingting Yu, Shanghai (CN); Richard Soll, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/036,268

(22) PCT Filed: Nov. 7, 2014

(86) PCT No.: PCT/US2014/064465
§ 371 (c)(1),
(2) Date: May 12, 2016

(87) PCT Pub. No.: WO2015/073310
PCT Pub. Date: May 21, 2015

(65) Prior Publication Data
US 2016/0297792 A1    Oct. 13, 2016

(30) Foreign Application Priority Data
Nov. 12, 2013  (WO) ................ PCT/CN2013/086923

(51) Int. Cl.
| | | |
|---|---|---|
| *A61K 31/4178* | (2006.01) |
| *A61K 31/4439* | (2006.01) |
| *A61K 31/4436* | (2006.01) |
| *A61K 31/443* | (2006.01) |
| *A61K 31/551* | (2006.01) |
| *A61K 31/541* | (2006.01) |
| *A61K 31/5377* | (2006.01) |
| *A61K 31/496* | (2006.01) |
| *C07D 401/06* | (2006.01) |
| *C07D 401/14* | (2006.01) |
| *C07D 401/04* | (2006.01) |
| *C07D 403/06* | (2006.01) |

(Continued)

(52) U.S. Cl.
CPC ........ *C07D 401/06* (2013.01); *A61K 31/4178* (2013.01); *A61K 31/454* (2013.01); *A61K 31/4545* (2013.01); *A61K 31/496* (2013.01); *A61K 31/541* (2013.01); *A61K 31/551* (2013.01); *A61K 45/06* (2013.01); *A61P 31/18* (2018.01); *C07D 213/14* (2013.01); *C07D 233/61* (2013.01); *C07D 249/08* (2013.01); *C07D 401/14* (2013.01); *C07D 403/06* (2013.01); *C07D 403/14* (2013.01); *C07D 405/14* (2013.01); *C07D 409/06* (2013.01); *C07D 413/14* (2013.01); *C07D 417/14* (2013.01); *C07D 471/04* (2013.01); *C07D 471/10* (2013.01)

(58) Field of Classification Search
CPC ............ A61K 31/4178; A61K 31/4439; A61K 31/4436; A61K 31/443; A61K 31/551; A61K 31/541; A61K 31/5377; A61K 31/496; C07D 401/06; C07D 401/14; C07D 401/04; C07D 403/06; C07D 403/14; C07D 409/06; C07D 413/04; C07D 417/04
USPC .......... 514/218, 227.8, 235.8, 252.2, 252.11, 514/252.14, 252.18, 254.02, 254.05, 278, 514/321, 326, 397; 540/492; 544/58.2, 544/121, 354, 362, 364, 366, 367, 368, 544/369, 370; 546/20, 194, 198, 209, 546/210; 548/341.1, 343.1
See application file for complete search history.

(56) References Cited

U.S. PATENT DOCUMENTS

| | | | |
|---|---|---|---|
| 5,717,100 A | 2/1998 | Selnick et al. | |
| 5,856,326 A | * 1/1999 | Anthony | .............. C07D 233/64 514/218 |

(Continued)

FOREIGN PATENT DOCUMENTS

| | | | | |
|---|---|---|---|---|
| WO | WO9909985 A1 | 3/1999 | | |
| WO | WO 00/51614 | * 9/2000 | .......... A61K 31/496 |

(Continued)

OTHER PUBLICATIONS

Arjomandi et al., Strategy 14C-Labeling of a Series of Bis(Heteroaryl)Piperazines, Journal of Labelled Compounds and Radiopharmaceuticals, vol. 54, No. 7, pp. 363-366, 2011.*

(Continued)

*Primary Examiner* — Brenda L Coleman
(74) *Attorney, Agent, or Firm* — Jeffrey P. Bergman; Catherine D. Fitch

(57) ABSTRACT

The present invention relates to piperidine or piperazine linked imidazole and triazole derivatives, compositions comprising said compounds, alone or in combination with other drugs, and methods of using the compounds for improving the pharmacokinetics of a drug. The compounds of the invention are useful in human and veterinary medicine for inhibiting CYP3A4 and for improving the pharmacokinetics of a therapeutic compound that is metabolized by CYP3A4.

8 Claims, No Drawings

(51) Int. Cl.

| | | |
|---|---|---|
| *C07D 403/14* | (2006.01) | |
| *C07D 409/06* | (2006.01) | |
| *C07D 413/04* | (2006.01) | |
| *C07D 417/04* | (2006.01) | |
| *A61K 45/06* | (2006.01) | |
| *A61K 31/454* | (2006.01) | |
| *C07D 405/14* | (2006.01) | |
| *C07D 413/14* | (2006.01) | |
| *C07D 417/14* | (2006.01) | |
| *C07D 249/08* | (2006.01) | |
| *C07D 233/61* | (2006.01) | |
| *A61P 31/18* | (2006.01) | |
| *C07D 213/14* | (2006.01) | |
| *C07D 471/04* | (2006.01) | |
| *A61K 31/4545* | (2006.01) | |
| *C07D 471/10* | (2006.01) | |

(56) References Cited

U.S. PATENT DOCUMENTS

| | | | | |
|---|---|---|---|---|
| 5,891,889 | A | 4/1999 | Anthony | |
| 5,965,578 | A | 10/1999 | Graham et al. | |
| 6,172,076 | B1 | 1/2001 | Embrey et al. | |
| 6,355,643 | B1 * | 3/2002 | Lumma | C07D 233/64 514/218 |
| 6,358,956 | B1 * | 3/2002 | Hartman | C07D 233/64 514/252.13 |
| 6,387,903 | B1 * | 5/2002 | Dinsmore | C07D 403/06 514/254.05 |
| 6,562,823 | B1 * | 5/2003 | Dinsmore | C07D 498/18 514/250 |
| 7,919,488 | B2 | 4/2011 | Planken et al. | |
| 2002/0052380 | A1 * | 5/2002 | Dinsmore | C07D 403/06 514/254.05 |
| 2002/0072081 | A1 * | 6/2002 | Eng | C07D 233/64 435/15 |
| 2006/0009645 | A1 | 1/2006 | Smith et al. | |
| 2007/0167497 | A1 | 7/2007 | Nambu et al. | |
| 2008/0021011 | A1 | 1/2008 | Planken et al. | |
| 2009/0175820 | A1 | 7/2009 | Desai et al. | |
| 2012/0076756 | A1 | 3/2012 | Qiu et al. | |
| 2014/0005103 | A1 * | 1/2014 | Coburn | C07D 401/14 514/4.1 |

FOREIGN PATENT DOCUMENTS

| | | | | |
|---|---|---|---|---|
| WO | WO 00/75135 | * | 12/2000 | C07D 401/14 |
| WO | WO 01/07437 | * | 2/2001 | C07D 403/06 |
| WO | WO 01/22963 | * | 4/2001 | A61K 31/44 |
| WO | 2006108879 A2 | | 10/2006 | |
| WO | 2007034312 A2 | | 3/2007 | |
| WO | 2006010921 A2 | | 1/2008 | |
| WO | 2010133544 A1 | | 11/2010 | |
| WO | WO2014004416 A1 | | 1/2014 | |
| WO | WO2014197345 A2 | | 12/2014 | |

OTHER PUBLICATIONS

Ho et al., Synthesis of a 14C-Labeled FPTase Inhibitor via a Pd-Catalyzed Cyanation With Zn(14CN)2 and via Bromo[14C]acetic Acid, Journal of Labelled Compounds and Radiopharmaceuticals, vol. 51, No. 12, pp. 399-403, 2008.*
Nguyen et al., Potent Inhibitors of Farnesyltransferase and Geranylgeranyltransferase-I, Bioorganic & Medicinal Chemistry Letters, vol. 12, No. 9, pp. 1269-1273, 2002.*
Singh et al., Pharmacokinetics and Metabolism of a RAS Farnesyl Transferase Inhibitor in Rats and Dogs: In Vitro-In Vivo Correlation, Drug Metabolism and Disposition, vol. 29, No. 12, pp. 1578-1587, 2001.*
Qin, Tandem Mass Spectrum of a Farnesyl Transferase Inhibitor—Gas-Phase Rearrangements Involving Imidazole, Journal of Mass Spectrometry, vol. 36, No. 8, pp. 911-917, 2001.*
Dinsmore et al., Oxo-Piperazine Derivatives of N-Arylpiperazinones as Inhibitors of Farnesyltransferase, Bioorganic & Medicinal Chemistry Letters, vol. 11, No. 4, pp. 537-540, 2001.*
Tucker et al., The Synthesis and Biological Evaluation of a Series of Potent Dual Inhibitors of Farnesyl and Geranyl-Geranyl Protein Transferases, Bioorganic & Medicinal Chemistry Letters, vol. 12, No. 7, pp. 2027-2030, 2002.*
Berge et al., "Pharmaceutical Salts", J. Pharm Sci., 1977, pp. 1-19, vol. 66, No. 1.
Bingham et al., Over one hundred solvates of sulfathiazole, Chem. Commun., 2001, pp. 603-604.
Bolm, C., et al, "a-Trialkylsily-Substituted a-Amino Acids", Angew Chem. Int. Ed., 2000, pp. 2288-2290, vol. 39, No. 13.
Caira et al., Preparation and Crystal Characterization of a Polymorph, a Monohydrate, and an Ethyl Acetate Solvate of the Antifungal Fiuconazole, J. Pharmaceutical Sci, 2004, 601-611, 93(3).
Giralt, E., et al, "Replacement of a Proline With Silaproline Causes a 20-Fold Increase in the Cellular Uptake of a Pro-Rich Peptide", J. Am. Chem. Soc., 2006, p. 8479-8483, vol. 128.
Gould, P.L., "Salt Selections for Basic Drugs", Intl. J. Pharmaceutics, 1936, pp. 201-217, vol. 33.
Green & Wuts, "Protective Groups in Organic Synthesis", 2nd Edition, 1991.
Greene, et al., "Protection for the Carbonyl Group", Organic Synthesis, 1999, pp. 312-344.
Johansson, T., et al, "In Vitro Metabolism of Haloperidol and Sila-Haloperidol: New Metabolic Pathways Resulting From Carbon/Silicon Exchange", Drug Metabolism and Disposition, 2010, pp. 78-83, vol. 38.
Masato Chiba, et al, "P450 Interaction With Farnesyl-Protein Transferase Inhibitors Metobolic Stability, Inhibitory Potency, and P450 Binding Spectra in Human Liver Microsomes", Biochemical Pharmacology, 2001, 773-776, vol. 62, WO.
T. Higuchi and V. Stella, "Pro-drugs as Novel Delivery Systems" (1987) 14 of the A.C.S. Symposium Series.
Van Tonder, et al, "Preparation and Physicochemical Characterization of 5 Niclosamide Solvates and 1 Hemisolvate", AAPS Pharmscitech, 2004, pp. 1-10, vol. 5, No. 1.
Supplementary European Search Report and Written Opinion for 14861810.1 dated Apr. 7, 2017, 7 pages.

* cited by examiner

PIPERIDINE OR PIPERAZINE LINKED IMIDAZOLE AND TRIAZOLE DERIVATIVES AND METHODS OF USE

CROSS-REFERENCE TO RELATED APPLICATIONS

This application is the national stage application under 35 U.S.C. 371 of International Patent Application No. PCT/US2014/064465, filed Nov. 7, 2014, which claims priority to International Patent Application No. PCT/CN2013/086923, filed Nov. 12, 2013. Each of the aforementioned PCT applications is incorporated by reference in its entirety.

BACKGROUND OF THE INVENTION

The cytochrome P450 enzyme system (CYP450) is responsible for the biotransformation of drugs from active substances to inactive metabolites that can be excreted from the body. In addition, the metabolism of certain drugs by CYP450 can alter their PK profile and result in sub-therapeutic plasma levels of those drugs over time. In the area of antiviral therapy, this can lead to resistance of the virus to the drug.

The virus causing acquired immunodeficiency syndrome (AIDS) is know by various names, including human immunodeficiency virus (HIV), of which two distinct families have been identified—HIV-1 and HIV-2. Many inhibitors of HIV, including HIV protease inhibitors, HIV integrase inhibitors and non-nucleoside reverse transcriptase inhibitors are metabolized by CYP450. This metabolic activity can lead to unfavorable pharmacokinetics, requiring administering more frequent and/or higher doses than are optimal.

Many drugs, including some HIV protease inhibitors, are now paired with other agents that improve exposure of the drug, with the drug-drug interaction being commonly referred to as "boosting." International Publication Nos. WO 2006/108879, WO 2007/034312 and WO 2008/010921; U.S. Patent Publication No. US 2009/0175820; and U.S. Pat. No. 7,919,488 describe compounds useful as pharmacokinetic enhancers.

Ritonavir, a common boosting agent, is widely used with HIV agents and is an HIV protease inhibitor itself that exerts its boosting effect through inhibition of Cytochrome P450 3A4 (CYP3A4) and p-glycoprotein drug transporters. Ritonavir, however, is associated with certain risks, including hepatotoxicity, hyperlipidemia and unfavorable gastrointestinal effects.

SUMMARY OF THE INVENTION

The present invention relates to piperidine or piperazine linked imidazole and triazole derivatives, compositions comprising said compounds, alone or in combination with other drugs, and methods of using the compounds for improving the pharmacokinetics of a drug. The compounds of the invention are useful in human and veterinary medicine for inhibiting CYP3A4 and for improving the pharmacokinetics of a therapeutic compound that is metabolized by CYP3A4.

DETAILED DESCRIPTION OF THE INVENTION

The invention encompasses a genus of compounds having the formula (I):

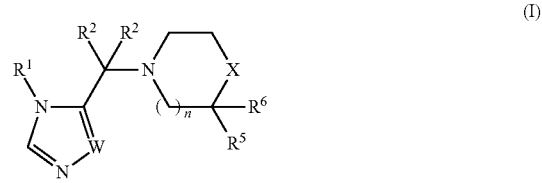

or a pharmaceutically acceptable salt thereof,
wherein:
n is 0 or 1;
W is —N= or —CH=;
X is —C(R$^3$)(R$^4$)—, —N(R$^3$)— or —S(O)$_2$—;
R$^1$ is selected from —(C$_1$-C$_6$ alkylene)-aryl, —(C$_1$-C$_6$ alkylene)-(5 or 6-membered heteroaryl), —(C$_1$-C$_6$ alkylene)-O-aryl, —(C$_1$-C$_6$ alkylene)-O-(5 or 6-membered heteroaryl) and C$_3$-C$_6$ cycloalkyl, wherein any aryl, heteroaryl or C$_3$-C$_6$ cycloalkyl group can be optionally substituted with up to four R$^9$ groups, which can be the same or different, and wherein said C$_3$-C$_6$ cycloalkyl group can be fused to a benzene ring and said fused benzene ring can be optionally substituted with up to four R$^9$ groups, which can be the same or different;
each occurrence of R$^2$ is independently selected from H, C$_1$-C$_6$ alkyl, —OH, —O—(C$_1$-C$_6$ alkyl) and —(C$_1$-C$_6$ alkylene)-O—(C$_1$-C$_6$ alkyl); or the two R$^2$ groups can be joined together with the atom to which they are attached to form a C$_3$-C$_6$ cycloalkyl ring;
R$^3$ and R$^4$ are independently selected from H, halo, —OH, —CN, Y, —O—Y, —C(O)—Y,
—C(O)—O—Y, —(C$_1$-C$_6$ alkylene)-Y, —(C$_1$-C$_6$ alkylene)-C(O)—Y, —(C$_1$-C$_6$ alkylene)-C(O)—O—Y and —(C$_1$-C$_6$ alkylene)-O—Y, wherein each Y is independently selected from:
(1) C$_1$-C$_6$ alkyl,
(2) C$_1$-C$_6$ haloalkyl,
(3) C$_1$-C$_6$ hydroxyalkyl,
(4) C$_3$-C$_6$ cyclohaloalkyl,
(5) C$_3$-C$_6$ cycloalkyl,
(6) phenyl, wherein said phenyl group can be optionally substituted with up to four R$^7$ groups,
(7) 5 or 6-membered heteroaryl, wherein said 5 or 6-membered heteroaryl group can be optionally substituted with up to four R$^7$ groups, and
(8) 5 or 6-membered monocyclic heterocycloalkyl or 9 or 10-membered bicyclic heterocycloalkyl, wherein said 5 or 6-membered monocyclic heterocycloalkyl group can optionally form a spirocycle with a C$_3$-C$_6$ cycloalkyl group or another 5 or 6-membered monocyclic heterocycloalkyl group, and wherein said 5 or 6-membered monocyclic heterocycloalkyl group and said 9 or 10-membered bicyclic heterocycloalkyl group can be optionally substituted on one or more ring carbon atoms with up to four R$^7$ groups, which can be the same or different, and wherein a ring carbon atom of a 5 or 6-membered monocyclic heterocycloalkyl group may be functionalized as a carbonyl group;
or R$^3$ and R$^4$ together with the carbon atom to which they are attached are joined together to form a 5 or 6-membered monocyclic heterocycloalkyl group, wherein said heterocycloalkyl group can be optionally substituted on one or more ring carbon atoms with up to four $R^7$ groups, which can be the same or different, and wherein a ring carbon atom of a 5 or 6-membered monocyclic heterocycloalkyl group may be functionalized as a carbonyl group;

$R^5$ is selected from H, $C_1$-$C_6$ alkyl, phenyl, —C(O)N($R^8$)$_2$ and —C(O)—Z, wherein Z is selected from piperidinyl, piperazinyl and morhoplinyl and wherein said Z is optionally substituted with 1 to 3 halo groups, and phenyl is optionally substituted with —N($R^8$)$_2$, $R^6$ is H or may be joined together with $R^5$ to form carbonyl, each occurrence of $R^7$ and each occurrence of $R^9$ are independently selected from $C_1$-$C_6$ alkyl, phenyl, benzyl, 5 or 6-membered heteroaryl, —CH$_2$-(5 or 6-membered heteroaryl), 5 or 6-membered heterocycloalkyl, —CH$_2$— (5 or 6-membered heterocycloalkyl), $C_1$-$C_6$ hydroxyalkyl, $C_1$-$C_6$ haloalkyl, halo, —CN, —N($R^8$)$_2$, —($C_1$-$C_6$ alkylene)-N($R^8$)$_2$, —OR$^8$, —C(O)OR$^8$, —SR$^8$, —S(O)$_2$R$^8$, —C(O)N($R^8$)$_2$, —($C_1$-$C_6$ alkylene)-C(O)OR$^8$, —($C_1$-$C_6$ alkylene)-SR$^8$, —($C_1$-$C_6$ alkylene)-S(O)$_2$R$^8$ and —($C_1$-$C_6$ alkylene)-C(O)N($R^8$)$_2$, wherein said phenyl, 5 or 6-membered heteroaryl and 5 or 6-membered heterocycloalkyl groups can be optionally substituted with one to three groups selected from $C_1$-$C_6$ alkyl, halo, $C_1$-$C_6$ hydroxyalkyl, $C_1$-$C_6$ haloalkyl, halo, —CN, —N($R^8$)$_2$ and —OR$^8$; and each occurrence of $R^8$ is independently H, $C_1$-$C_6$ alkyl or benzyl optionally substituted with one or two methoxy groups ("Embodiment E1").

In another embodiment (Embodiment E2"), the invention encompasses compounds having the formula (Ia):

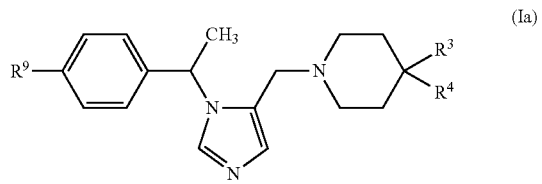

(Ia)

or a pharmaceutically acceptable salt thereof, wherein $R^3$, $R^4$ and $R^9$ are defined as in Embodiment E1.

In another embodiment (Embodiment E3"), the invention encompasses compounds of formula (Ia), or a pharmaceutically acceptable salt thereof, wherein $R^9$ is —F or —CN, and $R^3$ and $R^4$ and are defined as in Embodiment E1.

In another embodiment (Embodiment E4"), the invention encompasses compounds of formula (Ia), or a pharmaceutically acceptable salt thereof, wherein $R^3$ is selected from (1) $C_1$-$C_6$ alkyl, (2) $C_3$-$C_6$ cycloalkyl, (3) phenyl, wherein said phenyl group can be optionally substituted with up to four halo groups, (4) 5 or 6-membered heteroaryl, wherein said 5 or 6-membered heteroaryl group can be optionally substituted with methyl, and (5) 5 or 6-membered monocyclic heterocycloalkyl; and $R^4$ is selected from —CN or —CH$_3$, and $R^9$ is defined as in Embodiment E1 or Embodiment E2.

In another embodiment (Embodiment E5"), the invention encompasses compounds of formula (Ia), or a pharmaceutically acceptable salt thereof, wherein $R^3$ is selected from benzo[d]oxazol-2-yl and benzo[d]thiazol-2-yl, said benzo[d]oxazol-2-yl and benzo[d]thiazol-2-yl groups each optionally substituted with 1 to 3 groups independently selected from: halo, —CH$_3$ and —OCH$_3$; and $R^4$ is H, and $R^9$ is defined as in Embodiment E1 or Embodiment E2.

In another embodiment (Embodiment E6"), the invention encompasses compounds having the formula (Ib):

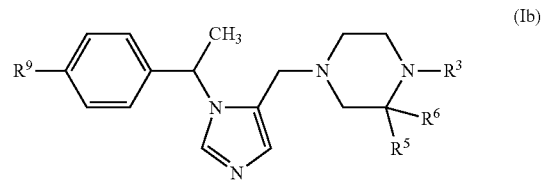

(Ib)

or a pharmaceutically acceptable salt thereof, $R^3$, $R^5$, $R^6$ and $R^9$ are defined as in Embodiment E1.

In another embodiment (Embodiment E7"), the invention encompasses compounds of formula (Ib), or a pharmaceutically acceptable salt thereof, wherein $R^9$ is —F or —CN, and $R^3$, $R^5$ and $R^6$ is defined as in Embodiment E1.

In another embodiment (Embodiment E8"), the invention encompasses compounds of formula (Ib), or a pharmaceutically acceptable salt thereof, wherein $R^3$ is thiazolyl substituted with —($C_1$-$C_6$ alkylene)-S(O)$_2$R$^8$, $R^5$ is H and $R^6$ is H, and $R^9$ is defined as in Embodiment E1 or Embodiment E7.

In another embodiment (Embodiment E9"), the invention encompasses compounds of formula (Ib), or a pharmaceutically acceptable salt thereof, wherein $R^3$ is phenyl, $R^5$ is —C(O)—Z, wherein Z is selected from piperidinyl, piperazinyl and morhoplinyl and wherein said Z is optionally substituted with 1 to 3 halo groups, and $R^6$ is H, and $R^9$ is defined as in Embodiment E1 or Embodiment E7.

In another embodiment (Embodiment E10"), the invention encompasses compounds of formula (Ib), or a pharmaceutically acceptable salt thereof, wherein $R^3$ is —C(O)—Y, Y is selected from (1) $C_1$-$C_6$ alkyl, (2) 1-methylcyclopropyl, (3) cyclobutyl optionally substituted with one or two halo groups, (4) phenyl, (5) pyridinyl, and (6) tetrahydro-2H-pyran-4-yl, $R^5$ is selected from H, $C_1$-$C_4$ alkyl and phenyl, and $R^6$ is H, and $R^9$ is defined as in Embodiment E1 or Embodiment E7.

In another embodiment (Embodiment E11"), the invention encompasses compounds of formula (Ib), or a pharmaceutically acceptable salt thereof, wherein $R^3$ is —CH$_2$—Y, Y is selected from phenyl, imidazo[1,2-a]pyridinyl, oxadiazolyl and thiazolyl, wherein said Y is optionally substituted with a group selected from: (1) phenyl wherein said phenyl is optionally substituted with one or two methoxy groups, (2) —N($R^8$)$_2$, (3) morpholinyl, (4) piperazinyl wherein said piperazinyl is optionally substituted with a methyl group, and (5) triazolylmethyl; and $R^5$ and $R^6$ are joined together to form carbonyl, and $R^9$ is defined as in Embodiment E1 or Embodiment E7.

In another embodiment (Embodiment E12"), the invention encompasses compounds of formula (Ib), or a pharmaceutically acceptable salt thereof, wherein $R^3$ is selected from $C_1$-$C_6$ hydroxyalkyl, —($C_1$-$C_6$ alkylene)-C(O)—Y, —($C_1$-$C_6$ alkylene)-C(O)—O—Y and —($C_1$-$C_6$ alkylene)-O—Y, where Y is $C_1$-$C_6$ alkyl; and $R^5$ is H and $R^6$ is H, and $R^9$ is defined as in Embodiment E1 or Embodiment E7.

Another embodiment of the invention encompasses a Compound of Formula (I), or a pharmaceutically acceptable salt thereof, wherein W is —C(H)—, X is —C($R^3$)($R^4$)— or —N($R^3$)—, n is 1, $R^1$ is —($C_1$-$C_4$ alkylene)-phenyl wherein said phenyl portion is substituted at the 4-position with —F or —CN, both $R^2$ groups are H, and all other variable are defined as in Embodiment E1.

In another embodiment, the Compounds of Formula (I) are in substantially purified form.

Other embodiments of the present invention include the following:

(a) A pharmaceutical composition comprising an effective amount of a Compound of Formula (I) or a pharmaceutically acceptable salt thereof, and a pharmaceutically acceptable carrier.

(b) The pharmaceutical composition of (a), further comprising one or more therapeutic compounds that are metabolized by CYP3A, preferably CYP3A4.

(c) The pharmaceutical composition of (b), wherein the therapeutic compound is an anti-HIV drug, preferably the anti-HIV drug(s) are selected from the group consisting of HIV protease inhibitors, HIV integrase inhibitors nucleoside reverse transcriptase inhibitors and non-nucleoside reverse-transcriptase inhibitors.

(d) A pharmaceutical combination that is (i) a Compound of Formula (I) and ii) a therapeutic compound metabolized by CYP3A4 that is an anti-HIV drug; wherein the Compound of Formula (I) and the therapeutic compound metabolized by CYP3A4 are each employed in an amount that renders the combination effective for inhibiting HIV replication, or for treating HIV infection and/or reducing the likelihood or severity of symptoms of HIV infection.

(e) The combination of (d), wherein the therapeutic compound metabolized by CYP3A4 is selected from the group consisting of HIV protease inhibitors, HIV integrase inhibitors, nucleoside reverse transcriptase inhibitors and non-nucleoside reverse-transcriptase inhibitors.

(f) A method of inhibiting HIV replication in a subject in need thereof which comprises administering to the subject: (i) a Compound of Formula (I) and (ii) one or more anti-HIV drugs, wherein the amounts of the Compound of Formula (I) and the anti-HIV drug(s) are together effective to inhibit HIV replication.

(g) A method of treating HIV infection and/or reducing the likelihood or severity of symptoms of HIV infection in a subject in need thereof which comprises administering to the subject (i) a Compound of Formula (I) and (ii) one or more anti-HIV drugs, wherein the amounts of the Compound of Formula (I) and the anti-HIV drug(s) are together effective to treat HIV infection.

(h) The method of (h), wherein the anti-HIV drug(s) are an selected from the group consisting of HIV protease inhibitors, HIV integrase inhibitors, nucleoside reverse transcriptase inhibitors and non-nucleoside reverse-transcriptase inhibitors.

(i) A method of inhibiting HIV replication in a subject in need thereof which comprises administering to the subject the pharmaceutical composition of (c) or the combination of (d) or (e).

(j) A method of treating HIV infection and/or reducing the likelihood or severity of symptoms of HIV infection in a subject in need thereof which comprises administering to the subject the pharmaceutical composition of (b) or (c) or the combination of (d) or (e).

Additional embodiments of the invention include the pharmaceutical compositions, combinations and methods set forth in (a)-(j) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate. It is understood that references to compounds would include the compound in its present form as well as in different forms, such as polymorphs, solvates and hydrates, as applicable.

It is further to be understood that the embodiments of compositions and methods provided as (a) through (j) above are understood to include all embodiments of the compounds, including such embodiments as result from combinations of embodiments.

The Compounds of Formula (I) may be referred to herein by chemical structure and/or by chemical name. In the instance that both the structure and the name of a Compound of Formula (I) are provided and a discrepancy is found to exist between the chemical structure and the corresponding chemical name, it is understood that the chemical structure will predominate.

Non-limiting examples of the Compounds of Formula (I) include compounds 1-72 as set forth below, and pharmaceutically acceptable salts thereof.

DEFINITIONS AND ABBREVIATIONS

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc. . . .

As used herein, and throughout this disclosure, the following terms, unless otherwise indicated, shall be understood to have the following meanings:

A "subject" is a human or non-human mammal. In one embodiment, a subject is a human. In another embodiment, a subject is a primate. In another embodiment, a subject is a monkey. In still another embodiment, the subject is a dog, cat, horse, pig, hamster or other companion animal.

The term "effective amount" as used herein, refers to: (i) an amount administered of a Compound of Formula (I), or pharmaceutically acceptable salt thereof, that is effective for inhibiting CYP3A4 in a subject, (ii) the amounts administered of each of a combination of: (A) a Compound of Formula (I), or pharmaceutically acceptable salt thereof, and (B) a therapeutic compound metabolized by CYP3A4 wherein the amounts administered are together effective in producing the desired therapeutic, ameliorative, inhibitory or preventative effect when administered to a subject. In one embodiment the patient is suffering from HIV infection or AIDS and the therapeutic compound is an anti-HIV agent. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HIV viral infection or AIDS, refers to reducing the likelihood or severity of HIV infection or AIDS.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)— alkyl, —O—C(O)-aryl, —O—C(O)-cycloalkyl, —C(O)OH and —C(O)O-alkyl. The term "$C_2$-$C_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —$CH_2$—, —$CH_2CH_2$—, —$CH_2CH_2CH_2$—, —$CH_2CH_2CH_2CH_2$—, —CH($CH_3$)$CH_2CH_2$—, —CH($CH_3$)— and —$CH_2$CH($CH_3$)$CH_2$—. In one embodiment, an alkylene group has from 1 to about 6 carbon atoms. In another embodiment, an alkylene group has from about 3 to about 5 carbon atoms. In another embodiment, an alkylene group is branched. In another embodiment, an alkylene group is linear. In one embodiment, an alkylene group is —$CH_2$—. The term "$C_1$-$C_6$ alkylene" refers to an alkylene group having from 1 to 6 carbon atoms. The term "$C_3$-$C_5$ alkylene" refers to an alkylene group having from 3 to 5 carbon atoms.

The term "alkenylene," as used herein, refers to an alkenyl group, as defined above, wherein one of the alkenyl group's hydrogen atoms has been replaced with a bond. Non-limiting examples of alkenylene groups include —CH=CH—, —CH=CHCH$_2$—, —CH$_2$CH=CH—, —CH$_2$CH=CHCH$_2$—, —CH=CHCH$_2$CH$_2$—, —CH$_2$CH$_2$CH=CH— and —CH(CH$_3$)CH=CH—. In one embodiment, an alkenylene group has from 2 to about 6 carbon atoms. In another embodiment, an alkenylene group has from about 3 to about 5 carbon atoms. In another embodiment, an alkenylene group is branched. In another embodiment, an alkenylene group is linear. The term "$C_2$-$C_6$ alkylene" refers to an alkenylene group having from 2 to 6 carbon atoms. The term "$C_3$-$C_5$ alkenylene" refers to an alkenylene group having from 3 to 5 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein. In one embodiment, a cycloalkyl group is unsubstituted. The term "3 to 6-membered cycloalkyl" refers to a cycloalkyl group having from 3 to 6 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

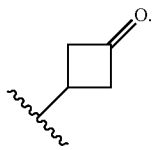 [SMILES: *C1CC(=O)C1]

The term "CYP3A," as used herein, refers to the all the known members of the 3A subfamily of the cytochrome P450 superfamily of genes. CYP3A includes, but is not limited to CYP3A4, CYP3A5, CYP3A7 and CYP3A43. In one embodiment, the CYP3A gene is CYP3A4.

The term "halo," as used herein, means —F, —Cl, —Br or —I. In one embodiment, the halo group is F.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —$CH_2F$, —$CHF_2$, —$CF_3$, —$CH_2Cl$ and —$CCl_3$. The term "$C_1$-$C_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms have been replaced with an —OH group. In one embodiment, a hydroxyalkyl group has from 1 to 6 carbon atoms. Non-limiting examples of hydroxyalkyl groups include —$CH_2OH$, —$CH_2CH_2OH$, —$CH_2CH_2CH_2OH$ and —$CH_2CH(OH)CH_3$. The term "$C_1$-$C_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently), N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic. A heteroaryl group can be optionally substituted by one or more "ring system substituents" which may be the same or different, and are as defined herein. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered heteroaryl. In another embodiment, a heteroaryl group comprises a 5- to 6-membered heteroaryl group fused to a benzene ring. Unless otherwise indicated, a heteroaryl group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently), S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from about 3 to about 7 ring atoms. In another embodiment, a heterocycloalkyl group is monocyclic has from about 4 to about 7 ring atoms. In another embodiment, the heterocycloalkyl group is bicyclic and has 9 or 10 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone and the like, and all isomers thereof.

A ring carbon atom of a heterocycloalkyl group may be functionalized as a carbonyl group. An illustrative example of such a heterocycloalkyl group is:

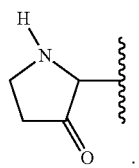 [SMILES: *C1NCCC1=O]

In one embodiment, a heterocycloalkyl group is a 5-membered monocyclic heterocycloalkyl. In another embodiment, a heterocycloalkyl group is a 6-membered monocyclic heterocycloalkyl. The term "3 to 6-membered monocyclic cycloalkyl" refers to a monocyclic heterocycloalkyl group having from 3 to 6 ring atoms. The term "4 to 6-membered monocyclic cycloalkyl" refers to a monocyclic heterocycloalkyl group having from 4 to 6 ring atoms. The term "7 to 11-membered bicyclic heterocycloalkyl" refers to a bicyclic heterocycloalkyl group having from 7 to 11 ring atoms. Unless otherwise indicated, an heterocycloalkyl group is unsubstituted.

The term "HIV," as used herein, refers generically to all known species of the HIV virus, including, but not limited to, HIV-1 and HIV-2.

The term "ring system substituent," as used herein, refers to a substituent group attached to an aromatic or non-aromatic ring system which, for example, replaces an available hydrogen on the ring system. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

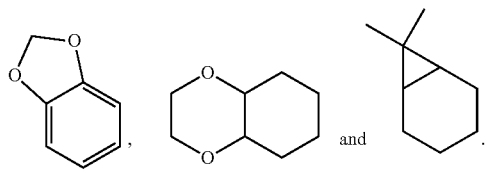

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., C$_1$-C$_6$ alkyl, R$^2$, R$^8$, etc.) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a Compound of Formula (I) or a pharmaceutically acceptable salt of the compound. The transformation may occur by various mechanisms (e.g., by metabolic or chemical processes), such as, for example, through hydrolysis in blood.

For example, if a Compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, (C$_1$-C$_8$)alkyl, (C$_2$-C$_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—(C$_1$-C$_2$)alkylamino(C$_2$-C$_3$)alkyl (such as β-dimethylaminoethyl), carbamoyl-(C$_1$-C$_2$)alkyl, N,N-di (C$_1$-C$_2$)alkylcarbamoyl-(C$_1$-C$_2$)alkyl and piperidino-, pyrrolidino- or morpholino(C$_2$-C$_3$)alkyl, and the like. Similarly, if a Compound of Formula (I) contains an alcohol functional group, a prodrug can be formed by the replacement of one or more of the hydrogen atoms of the alcohol groups with a group such as, for example, (C$_1$-C$_6$)alkanoyloxymethyl, 1-((C$_1$-C$_6$)alkanoyloxy)ethyl, 1-methyl-1-((C$_1$-C$_6$)alkanoyloxy) ethyl, (C$_1$-C$_6$)alkoxycarbonyloxymethyl, N—(C$_1$-C$_6$) alkoxycarbonylaminomethyl, succinoyl, (C$_1$-C$_6$)alkanoyl, α-amino(C$_1$-C$_4$)alkyl, α-amino(C$_1$-C$_4$)alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate) or a phosphate of structure PO$_3$M$_2$ where M is either sodium or potassium.

If a Compound of Formula (I) incorporates an amine functional group, a prodrug can be formed by the replacement of a hydrogen atom in the amine group with a group such as, for example, R-carbonyl-, RO-carbonyl-, NRR'-carbonyl- wherein R and R' are each independently (C$_1$-C$_{10}$) alkyl, (C$_3$-C$_7$) cycloalkyl, benzyl, a natural α-aminoacyl, —C(OH)C(O)OY$^1$ wherein Y$^1$ is H, (C$_1$-C$_6$)alkyl or benzyl, —C(OY$^2$)Y$^3$ wherein Y$^2$ is (C$_1$-C$_4$) alkyl and Y$^3$ is (C$_1$-C$_6$) alkyl; carboxy (C$_1$-C$_6$)alkyl; amino(C$_1$-C$_4$)alkyl or mono-N— or di-N,N—(C$_1$-C$_6$)alkylaminoalkyl; —C(Y$^4$)Y$^5$ wherein Y$^4$ is H or methyl and Y$^5$ is mono-N— or di-N, N—(C$_1$-C$_6$)alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, C$_{1-4}$alkyl, —O—(C$_{1-4}$alkyl) or amino); (2) sulfonate esters, such as alkyl- or aralkylsulfonyl (for example, methanesulfonyl); (3) amino acid esters (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Compounds of Formula (I) can form salts which are also within the scope of this invention. Reference to a Compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a Compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Stereochemically pure compounds may also be prepared by using chiral starting materials or by employing salt resolution techniques. Also, some of the Compounds of Formula (I) may be atropisomers (e.g., substituted biaryls) and are considered as part of this invention. Enantiomers can also be directly separated using chiral chromatographic techniques.

It is also possible that the Compounds of Formula (I) may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a Compound of Formula (I) incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to apply equally to the salt, solvate, ester and prodrug of enantiomers, stereoisomers, rotamers, tautomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

Polymorphic forms of the Compounds of Formula (I), and of the salts, solvates, hydrates, esters and prodrugs of the Compounds of Formula (I), are intended to be included in the present invention.

The following abbreviations are used below and have the following meanings: AcOH is acetic acid; Boc is tert-butyloxycarbonyl, (Boc)$_2$O or Boc$_2$O is Boc anhydride; n-BuLi is n-butyl lithium; t-BuNO$_2$ or t-BuONO is tert-butyl nitrite; Cbz is carboxybenzyl; DCM is dichloromethane; DIEA is N,N-diisopropylethylamine; DMF is dimethylformamide; DMSO is dimethylsulfoxide; EtOAc is ethyl acetate; EtOH is ethanol; Et$_3$N or TEA is triethylamine; HMPA is hexamethylphosphoramide; HOAc is acetic acid; HPLC is high-pressure liquid chromatography; KSCN is potassium thiocyanate; LCMS is liquid chromatography-mass spectrometry; LDA is lithium diisopropylamide; MeCN is acetonitrile; MeI is iodomethane; MeOH is methanol; MS is mass spectroscopy; NaBH(OAc)$_3$ is sodium triacetoxy borohydride; NMR is nuclear magnetic resonance spectroscopy; PCy$_3$ is tricyclohexylphosphine; Pd(OAc)$_2$ is palladium(II) acetate; Pd$_2$(dba)$_3$ is tris dibenzylideneacetone dipalladium; PE is petroleum ether; PG is protecting group; Pd/C is palladium on carbon; Prep is preparative; rt is room temperature; TBAF is n-tetrabutylammonium fluoride; TFA is trifluoroacetic acid; TLC is thin-layer chromatography; TMSCN is trimethylsilyl cyanide; Ts is 4-toluenesulfonyl; THF is tetrahydrofuran; wt % is percentage by weight; and X-phos is 2-dicyclohexylphosphino-2',4',6'-triisopropylbiphenyl.

Uses of the Piperidine or Piperazine Imidazole and Triazole Derivatives

The compounds of the invention are useful in human and veterinary medicine for inhibiting CYP3A4. In addition, the compounds of the invention are useful for improving the pharmacokinetics of a therapeutic compound that is metabolized by CYP3A4.

The present invention provides novel compounds of Formula (I) that inhibit CYP3A. Uses of the compounds of Formula (I) described herein include inhibiting CYP3A, which may be useful for increasing the pharmacokinetics of compounds that are metabolized by CYP3A.

The present invention also encompasses the use of a Compound of Formula (I) for inhibiting CYP3A4 in a subject, said method comprising administering to said subject a Compound of Formula (I), or pharmaceutically acceptable salt thereof, in an amount that is effective to inhibit CYP3A4 in said subject.

The present invention also encompasses the use of a Compound of Formula (I) for the manufacture of a medicament useful for inhibiting CYP3A4 in a subject.

Inhibition of CYP3A4

The present invention provides methods for inhibiting CYP3A4 in a subject, said method comprising administering to said subject a Compound of Formula (I), or pharmaceutically acceptable salt thereof, in an amount that is effective to inhibit CYP3A4 in said subject.

The present invention also provides methods that may be, or are believed to be, useful for inhibiting other members of CYP3A in a subject, said method comprising administering to said subject a Compound of Formula I, or pharmaceutically acceptable salt thereof, in an amount that is effective to inhibit CYP3A in said subject. In one embodiment, the CYP3A being inhibited is CYP3A5. In another embodiment, the CYP3A being inhibited is CYP3A7. In another embodiment, the CYP3A being inhibited is CYP3A4.

Improving the Pharmacokinetics of a Therapeutic Compound that is Metabolized by CYP3A4

The present invention provides methods for improving the pharmacokinetics of a therapeutic compound that is metabolized by CYP3A4, comprising administering to a subject in need of such treatment an effective amount of a combination of said therapeutic compound and a Compound of Formula (I) or pharmaceutically acceptable salt thereof.

The present invention also provides methods that may be, or are believed to be, useful for improving the pharmacokinetics of a therapeutic compound that is metabolized by other members of CYP3A, comprising administering to a subject in need of such treatment an effective amount of a combination of said therapeutic compound and a Compound of Formula (I) or pharmaceutically acceptable salt thereof. In one embodiment, the therapeutic compound is metabolized by CYP3A5. In another embodiment, the therapeutic compound is metabolized by CYP3A7. In another embodiment, the therapeutic compound is metabolized by CYP3A43.

In one embodiment, the therapeutic compound whose pharmacokinetics are being improved is an anti-HIV drug.

In another embodiment, the therapeutic compound whose pharmacokinetics are being improved is an HIV protease inhibitor.

In still another embodiment, the therapeutic compound whose pharmacokinetics are being improved is an HIV integrase inhibitor.

In another embodiment, the therapeutic compound whose pharmacokinetics are being improved is a nucleoside reverse transcriptase inhibitor (nRTI).

In yet another embodiment, the therapeutic compound whose pharmacokinetics are being improved is a non-nucleoside reverse transcriptase inhibitor (nnRTI).

Treatment or Prevention of HIV Infection

The present invention provides methods for treating or preventing HIV infection in a subject comprising administering to the subject: (i) a Compound of Formula (I) or a pharmaceutically acceptable salt thereof and (ii) one or more anti-HIV drugs, wherein the amounts administered are together effective to treat or prevent HIV infection in said subject. In one embodiment, the present invention also provides methods for treating AIDS in a subject comprising administering to the subject: (i) a Compound of Formula (I) or a pharmaceutically acceptable salt thereof and (ii) one or more anti-HIV drugs, wherein the amounts administered are together effective to treat AIDS in said subject.

The compositions and combinations of the present invention can be useful for treating a subject suffering from infection related to any HIV genotype.

In one embodiment, the HIV infection being treated is HIV-1.

In another embodiment, the HIV infection being treated is HIV-2.

In another embodiment, the HIV infection being treated has transformed into AIDS.

Combination Therapy

When administering a combination of a Compound of Formula (I) and one or more anti-HIV drugs to a subject, the Compound of Formula (I) and anti-HIV drug may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Compound of Formula (I) and the anti-HIV drug(s) may be present in fixed amounts (dosage amounts) in a single dosage unit (e.g., a capsule, a tablet, and the like).

In one embodiment, the Compound of Formula (I) is administered during a time when the anti-HIV drug(s) exert their prophylactic or therapeutic effect, or vice versa.

In another embodiment, when administered in combination with a Compound of Formula (I), the anti-HIV drug(s) are administered in doses lower than the doses commonly employed when such agents are used as monotherapy for treating HIV infection. A lower dosage or less frequent administration of the anti-HIV drug(s) may reduce the toxicity of therapy without reducing the efficacy of therapy.

In one embodiment, the at least one Compound of Formula (I) and the anti-HIV drug(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

In one embodiment, the administration of a Compound of Formula (I) and the anti-HIV drug(s) may inhibit the resistance of the HIV infection to one or more of the agents being administered.

Anti-HIV Drugs

An "anti-HIV drug," as defined herein, is any agent which is directly or indirectly effective in the inhibition of HIV reverse transcriptase or another enzyme required for HIV replication or infection, the treatment or prophylaxis of HIV infection, and/or the treatment, prophylaxis or delay in the onset or progression of AIDS. It is understood that an anti-HIV drug is effective in treating, preventing, or delaying the onset or progression of HIV infection or AIDS and/or diseases or conditions arising therefrom or associated therewith. For example, the Compounds of Formula (I) can be effectively administered, whether at periods of pre-exposure and/or post-exposure, in combination with effective amounts of one or more anti-HIV drugs selected from anti-HIV drugs, immunomodulators, antiinfectives, useful for treating HIV infection or AIDS. HIV antivirals are listed in Table A below.

TABLE A

| Name | Type |
|---|---|
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| CMX-157 | nRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| Dolutegravir | PI |
| efavirenz, EFV, Sustiva ®, Stocrin ® | nnRTI |
| efavirenz + emtricitabine + tenofovir DF, Atripla ® | nnRTI + nRTI |
| Elvitegravir | InI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| raltegravir, MK-0518, Isentress ® | InI |
| rilpivirine, TMC-278 | nnRTI |
| Rilpivirine + emtricitabine + tenofovir, Complera | nnRTI + nRTI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| tipranavir, Aptivus ® | PI |

EI = entry inhibitor; FI = fusion inhibitor; InI = integrase inhibitor; PI = protease inhibitor; nRTI = nucleoside reverse transcriptase inhibitor; nnRTI = non-nucleoside reverse transcriptase inhibitor. Some of the drugs listed in the table are used in a salt form; e.g., abacavir sulfate, indinavir sulfate, atazanavir sulfate, nelfinavir mesylate.

In one embodiment, the one or more anti-HIV drugs are selected from raltegravir, lamivudine, abacavir, ritonavir, dolutegravir, atazanavir, elvitegravir and lopinavir.

In still another embodiment, the compound of formula (I) is used in combination with an anti-HIV drug which is atazanavir, and optionally one or more additional anti-HIV drugs.

In another embodiment, the compound of formula (I) is used in combination with an anti-HIV drug which is darunavir, and optionally one or more additional anti-HIV drugs.

In another embodiment, the compound of formula (I) is used in combination with at least two anti-HIV drugs which are darunavir and raltegravir.

In another embodiment, the compound of formula (I) is used in combination with at least two anti-HIV drugs which are atazanavir and raltegravir.

In still another embodiment, the compound of formula (I) is used in combination with at least two anti-HIV drugs which are ritonavir and lopinavir.

In another embodiment, the compound of formula (I) is used in combination with at least three anti-HIV drug which are lopinavir, ritonavir and raltegravir.

In one embodiment, the present invention provides pharmaceutical compositions comprising (i) a compound of formula (I) or a pharmaceutically acceptable salt thereof; (ii) a pharmaceutically acceptable carrier; and (iii) one or more additional anti-HIV drugs selected from lamivudine, abacavir, ritonavir and lopinavir, or a pharmaceutically acceptable salt thereof, wherein the amounts present of components (i) and (iii) are together effective for the treatment or prophylaxis of infection by HIV or for the treatment, prophylaxis, or delay in the onset or progression of AIDS in the subject in need thereof.

In another embodiment, the present invention provides a method for the treatment or prophylaxis of infection by HIV or for the treatment, prophylaxis, or delay in the onset or progression of AIDS in a subject in need thereof, which comprises administering to the subject (i) a compound of formula (I) or a pharmaceutically acceptable salt thereof and (ii) one or more additional anti-HIV drugs selected from raltegravir, lamivudine, abacavir, atazanavir, darunavir, ritonavir and lopinavir, or a pharmaceutically acceptable salt thereof, wherein the amounts administered of components (i) and (ii) are together effective for the treatment or prophylaxis of infection by HIV or for the treatment, prophylaxis, or delay in the onset or progression of AIDS in the subject in need thereof.

It is understood that the scope of combinations of the compounds of this invention with anti-HIV drugs is not limited to the HIV antivirals listed in Table A, but includes in principle any combination with any drug or pharmaceutical composition useful for the treatment or prophylaxis of AIDS. The anti-HIV drugs and other agents will typically be employed in these combinations in their conventional dosage ranges and regimens as reported in the art, including, for example, the dosages described in the *Physicians' Desk Reference*, Thomson PDR, Thomson PDR, 57$^{th}$ edition (2003), the 58$^{th}$ edition (2004), the 59$^{th}$ edition (2005), and the like. The dosage ranges for a compound of the invention in these combinations are the same as those set forth above.

The doses and dosage regimen of the other agents used in the combination therapies of the present invention for the treatment or prevention of HIV infection can be determined by the attending clinician, taking into consideration the approved doses and dosage regimen in the package insert; the age, sex and general health of the subject; and the type and severity of the viral infection or related disease or disorder. When administered in combination, the Compound(s) of Formula (I) and the other agent(s) can be administered simultaneously (i.e., in the same composition or in separate compositions one right after the other) or sequentially. This particularly useful when the components of the combination are given on different dosing schedules, e.g., one component is administered once daily and another component is administered every six hours, or when the preferred pharmaceutical compositions are different, e.g., one is a tablet and one is a capsule. A kit comprising the separate dosage forms is therefore advantageous.

Compositions and Administration

Due to their activity, the Compounds of Formula (I) are useful in veterinary and human medicine. As described above, the Compounds of Formula (I) are useful for inhibiting CYP3A4; improving the pharmacokinetics of a therapeutic compound that is metabolized by CYP3A4; and in combination with one or more anti-HIV agents for treating or preventing HIV infection in a subject in need thereof.

When administered to a subject, the Compounds of Formula (I) can be administered as a component of a composition that comprises a pharmaceutically acceptable carrier or vehicle. The present invention provides pharmaceutical compositions comprising an effective amount of at least one Compound of Formula (I) and a pharmaceutically acceptable carrier. In the pharmaceutical compositions and methods of the present invention, the active ingredients will typically be administered in admixture with suitable carrier materials suitably selected with respect to the intended form of administration, e.g., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, e.g., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the Compounds of Formula (I) are administered orally.

In another embodiment, the Compounds of Formula (I) are administered intravenously.

In one embodiment, the present invention provides compositions comprising a Compound of Formula (I) or a pharmaceutically acceptable salt thereof, and a pharmaceutically acceptable carrier.

In one embodiment, a pharmaceutical preparation comprising at least one Compounds of Formula (I) is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Compound(s) of Formula (I) by weight or volume. In various embodiments, the present compositions can contain, in one embodiment, from about 1% to about 70% or from about 5% to about 60% of the Compound(s) of Formula (I) by weight or volume.

The Compounds of Formula (I) can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the subject to be treated. The specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the Compounds of Formula (I) will be regulated according to the judgment of the attending clinician considering such factors as age, condition and size of the subject as well as severity of the symptoms being treated. The compositions of the invention can further comprise one or more additional therapeutic agents, selected from those listed above herein. Accordingly, in one embodiment, the present invention provides compositions comprising: (i) a Compound of Formula (I) or a pharmaceutically acceptable salt thereof; (ii) a therapeutic compound that is metabolized by CYP3A4; and (iii) a pharmaceutically acceptable carrier. In another embodiment, the present invention provides compositions comprising: (i) a Compound of Formula (I) or a pharmaceutically acceptable salt thereof; (ii) one or more anti-HIV drugs; and (iii) a pharmaceutically acceptable carrier, wherein the amounts in the composition are together effective to treat HIV infection.

In another embodiment, the present invention provides compositions comprising a Compound of Formula (I) or a pharmaceutically acceptable salt thereof, a pharmaceutically acceptable carrier, and one or more anti-HIV drugs, wherein said anti-HIV drugs are selected from raltegravir, lamivudine, abacavir, atazanavir, darunavir, lopinavir and ritonavir.

In still embodiment, the present invention provides compositions comprising a Compound of Formula (I) or a pharmaceutically acceptable salt thereof, a pharmaceutically acceptable carrier, and raltegravir.

Kits

In one aspect, the present invention provides a kit comprising a therapeutically effective amount of at least one Compound of Formula (I), or a pharmaceutically acceptable salt, solvate, ester or prodrug of said compound and a pharmaceutically acceptable carrier, vehicle or diluent.

In another aspect the present invention provides a kit comprising an amount of at least one Compound of Formula (I), or a pharmaceutically acceptable salt, solvate, ester or prodrug of said compound and a therapeutic compound that is metabolized by CYP3A4. In one embodiment, the Compounds of Formula (I) and the therapeutic compound that is metabolized by CYP3A4 are provided in the same container. In one embodiment, the Compounds of Formula (I) and the therapeutic compound that is metabolized by CYP3A4 are provided in separate containers.

In another aspect the present invention provides a kit comprising an amount of at least one Compound of Formula (I), or a pharmaceutically acceptable salt, solvate, ester or prodrug of said compound and an amount of at least one anti-HIV drug listed above, wherein the amounts of the two or more active ingredients result in a desired therapeutic effect. In one embodiment, the Compounds of Formula (I) and the one or more anti-HIV drugs are provided in the same container. In one embodiment, the Compounds of Formula (I) and the one or more anti-HIV drugs are provided in separate containers.

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below. Alternative synthetic pathways and analogous structures will be apparent to those skilled in the art of organic synthesis.

One skilled in the art of organic synthesis will recognize that the synthesis of the Compounds of Formula (I) may require protection of certain functional groups (i.e., derivatization for the purpose of chemical compatibility with a particular reaction condition). Suitable protecting groups for the various functional groups of these compounds and methods for their installation and removal are well known in the art of organic chemistry. A summary of many of these methods can be found in Greene et al., *Protective Groups in Organic Synthesis*, Wiley-Interscience, New York, (1999).

One skilled in the art of organic synthesis will also recognize that one route for the synthesis of the Compounds of Formula (I) may be more desirable depending on the choice of appendage substituents. Additionally, one skilled in the art will recognize that in some cases the order of reactions may differ from that presented herein to avoid functional group incompatibilities and thus adjust the synthetic route accordingly.

The preparation of some intermediates useful for making the Compounds of Formula (I) have been described in the literature and in compendia such as "Comprehensive Heterocyclic Chemistry" editions I, II and III, published by Elsevier and edited by A. R. Katritzky & R. J K Taylor. Manipulation of the required substitution patterns have also been described in the available chemical literature as summarized in compendia such as "Comprehensive Organic Chemistry" published by Elsevier and edited by DH R. Barton and W. D. Ollis; "Comprehensive Organic Functional Group Transformations" edited by edited by A. R. Katritzky & R. J K Taylor and "Comprehensive Organic Transformation" published by Wily-CVH and edited by R. C. Larock.

The Compounds Formula (I) may contain one or more silicon atoms. The compounds contemplated in this invention in general can be prepared using the carba-analog methodology unless otherwise noted. A recent review of the synthesis of silicon containing compounds can be found in "Silicon Chemistry: from Atom to Extended Systems", Ed P. Jutzi & U. Schubet; ISBN 978-3-527-30647-3. Preparation of silyl containing amino acids has been described. See Bolm et al., *Angew. Chem. Int Ed.*, 39:2289 (2000). Descriptions of improved cellular update (Giralt, *J. Am. Chem. Soc.*, 128:8479 (2006)) and reduced metabolic processing of silyl containing compounds have been described (Johansson et al., *Drug Metabolism & Disposition*, 38:73 (2009)).

The starting materials used and the intermediates prepared using the methods set forth in Schemes A-L may be isolated and purified if desired using conventional techniques, including but not limited to filtration, distillation, crystallization, chromatography and alike. Such materials can be characterized using conventional means, including physical constants and spectral data.

EXAMPLES

General Methods

Solvents, reagents, and intermediates that are commercially available were used as received. Reagents and intermediates that are not commercially available were prepared in the manner as described below. $^1$H NMR spectra were obtained on a Varian VNMR System 400 (400 MHz) and are reported as ppm downfield from Me$_4$Si with number of protons, multiplicities, and coupling constants in Hertz indicated parenthetically. Where LC/MS data are presented, analyses was performed using an Agilent 6110A MSD or an Applied Biosystems API-100 mass spectrometer and Shimadzu SCL-10A LC column. Altech platinum C18, 3 micron, 33 mm×7 mm ID; gradient flow: 0 minutes—10% CH$_3$CN, 5 minutes—95% CH$_3$CN, 5-7 minutes—95% CH$_3$CN, 7 minutes—stop. The retention time and observed parent ion are given. Flash column chromatography was performed using pre-packed normal phase silica from Biotage, Inc. or bulk silica from Fisher Scientific. Unless otherwise indicated, column chromatography was performed using a gradient elution of hexanes/ethyl acetate, from 100% hexanes to 100% ethyl acetate.

Example 1

(R)-4-Ethyl-1-((1-(1-(4-fluorophenyl)ethyl)-1H-imidazol-5-yl)methyl)piperidine-4-carbonitrile (Compound 1)

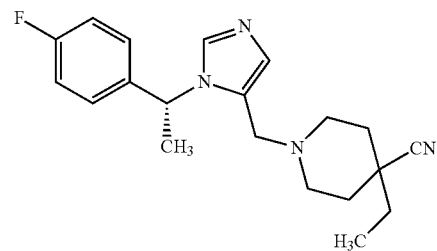 [SMILES: CCC1(C#N)CCN(Cc2cncn2[C@H](C)c2ccc(F)cc2)CC1]

Step A—Preparation of Int 1-3

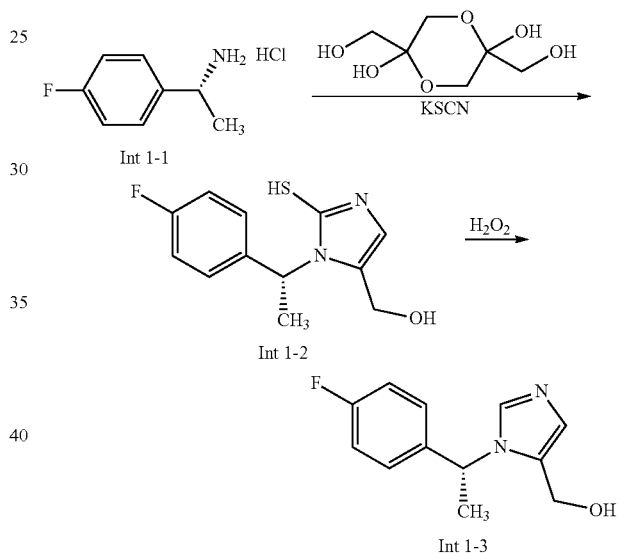

To a solution of compound Int 1-1 (200 g, 1.14 mol) in 2 L of 50% aqueous acetonitrile was added K$_2$CO$_3$ to adjust the solution to pH 8. Acetic acid (50 mL) was then added and the reaction was allowed to stir for 20 min before 1,3-dihydroxyacetone dimer (205 g, 1.14 mol) and KSCN (111 g, 1.14 mol) was added. The reaction mixture was allowed to stir at 9° C. for 5 hours when TLC (petroleum ether: EtOAc=1:2) showed the reaction to be complete. The reaction mixture was then cooled to 0° C. and H$_2$O$_2$ (388 mL, 30%, 3.42 mol) was added dropwise. The mixture was allowed to stir at 0° C. for 1 hour, then the reaction mixture was quenched with saturated Na$_2$SO$_3$ at 0° C. Solid Na$_2$CO$_3$ was added to the mixture to adjust to pH 8-10 and the solid was filtered off. The remained aqueous filtrate was extracted with ethyl acetate and the combined organic extracts were dried over Na$_2$SO$_4$, filtered and concentrated in vacuo to provide compound Int 1-3 (90 g), which was used in next step without further purification.

Step B—Preparation of Int 1-2

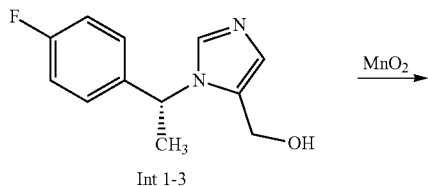

Int 1-3

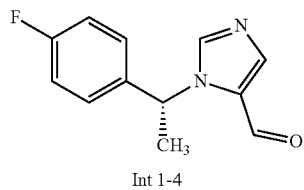

Int 1-4

To a solution of compound Int 1-3 (90 g, 0.41 mmol) in dioxane (1 L) was added MnO₂ (107 g, 1.23 mol) and the mixture was allowed to stir at 80° C. for 5 hours. The reaction mixture was filtered through Celite and the filtrate was concentrated in vacuo. The resulting residue was purified using column chromatography (1:1 petroleum ether/EtOAc) to provide 70 g (79%) of compound Int-1-4 as yellow oil.

Step C—Preparation of Int 1-5

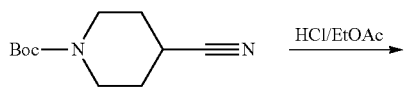

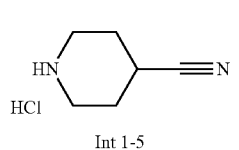

Int 1-5

To a solution of N-Boc-4-cyanopiperidine (2.62 g, 12.4 mmol) in EtOAc (10 mL) was carefully added 10 mL HCl/EtOAc. The mixture was stirred at room temperature for 1 h. The solvent was removed by reducing pressure to afford 2.12 g white solid. The filtrate was concentrated to dryness which was used directly in the next step directly. $^1$H NMR (CD$_3$OD) δ 3.4~03.32 (m, 2H), 3.23~3.17 (m, 3H), 2.26~2.21 (m, 2H), 2.10~2.01 (m, 2H).

Step D—Preparation of Int 1-6

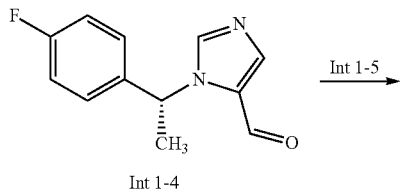

Int 1-4

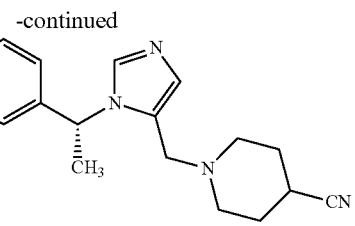

Int 1-6

To a stirred suspension of compound Int 1-5 (2.12 g) in 30 mL of dry THF was added compound Int 1-4 (2.7 g, 12.4 mmol), excess Ti(OPr)$_4$, MgSO$_4$ and Na$_2$CO$_3$. The mixture was stirred at 70° C. oil bath for 4 h. The mixture was cooled to room temperature, then to the stirring mixture suspension was added excess NaBH(OAc)$_3$ and stirred for 2 h. The mixture was filtrated and concentrated. The residue was purified by column to afford 3.3 g yellow solid. $^1$H NMR (CDCl$_3$) δ 7.65 (s, 1H), 7.01~6.98 (m, 4H), 6.89 (s, 1H), 5.62 (q, J=6.8 Hz, 1H), 2.57~2.49 (m, 4H), 2.23~2.08 (m, 2H), 1.83 (d, J=8.4 Hz, 2H), 1.79 (d, J=7.2 Hz, 3H), 1.76~1.70 (m, 3H). MS (ESI) m/z (M+1): 313.

Step E—Preparation of Compound 1

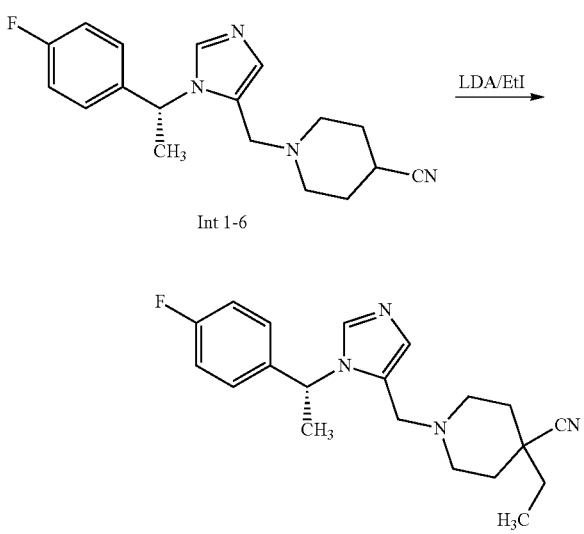

Compound 1

Compound Int 1-6 (0.322 g, 1.03 mmol) was dissolved in anhydrous THF (10 mL) and N$_2$ degassed for 5 times. The solution was cooled to −70° C. then 0.9 mL LDA (1.5M in THF) was carefully injected to the solution. The mixture was stirred at this temperature for 0.5 h, then iodoethane (0.2162 g, 1.38 mmol) was injected. The mixture was stirred at this temperature for another 0.5 h, methanol was added to quench the reaction and the solvent was removed by reducing pressure. The residue was re-dissolved in 5 mL MeOH, filtrated and purified by pre-HPLC to afford 198 mg white solid. $^1$H NMR (CD$_3$OD) δ 9.39 (s, 1H), 7.93 (s, 1H), 7.32 (s, 2H), 7.14 (s, 2H), 6.00 (s, 1H), 4.41~4.35 (m, 1H), 4.24 (d, J=13.6 Hz, 1H), 3.55 (s, 1H), 3.45 (s, 1H), 3.11 (d, J=10.4 Hz, 1H), 2.93 (d, J=9.2 Hz, 1H), 2.14 (t, J=15.6 Hz, 2H), 1.95~1.86 (m, 5H), 1.66 (d, J=6.4 Hz, 2H), 1.05 (s, 3H). MS (ESI) m/z (M+1): 341.

Example 2

(R)-1-((1-(1-(4-fluorophenyl)ethyl)-1H-imidazol-5-yl)methyl)-4-isopropylpiperidine-4-carbonitrile (Compound 2)

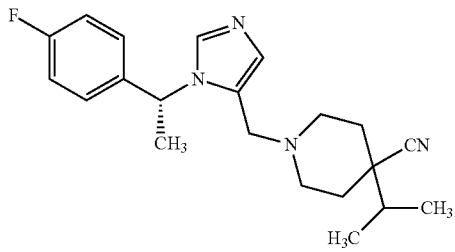 [SMILES: CC(C)C1(C#N)CCN(Cc2cncn2[C@H](C)c2ccc(F)cc2)CC1]

Step A—Preparation of Int 2-1

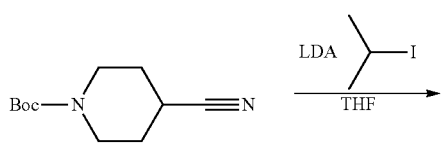

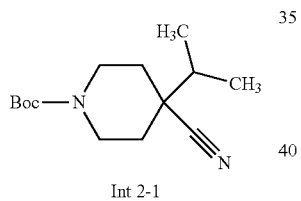

N-Boc-4-cyanopiperazine (1.46 g, 66.9 mmol) was dissolved in anhydrous THF (15 mL) and N₂ degassed for 5 times. The solution was cooled to −70° C. then 5.5 mL LDA (1.5M in THF, 1.2 eq) was carefully injected to the solution. The mixture was stirred at this temperature for 0.5 h, then 2-iodopropane (1.36 g, 80.3 mmol) was injected. The mixture was stirred at this temperature for another 0.5 h, methanol was added to quench the reaction and the solvent was removed by reducing pressure. The residue was purified by column to afford 2.11 g of a white solid. ¹H NMR (CDCl₃) δ 4.20~4.02 (m, 2H), 2.98~2.76 (m, 2H), 1.88 (d, J=12.8 Hz, 2H), 1.58 (q, J=6.8 Hz, 1H), 1.39 (s, 9H), 1.32 (d, J=4.0 Hz, 1H), 1.29 (d, J=4.4 Hz, 1H), 1.01 (d, J=6.8 Hz, 6H).

Step B—Preparation of Int 2-2

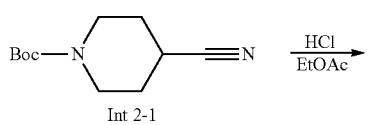

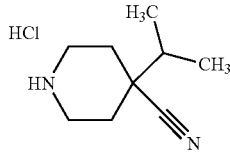

To a solution of compound Int 2-1 (0.52 g, 2.47 mmol) in EtOAc (5 mL) was carefully added 10 mL HCl/EtOAc. The mixture was stirred at room temperature for 1 h. The solvent was removed by reducing pressure to afford 0.50 g white solid. The filtrate was concentrated to dryness which was used directly in the next step directly. (Yield: 100%). ¹H-NMR (CD₃OD) δ 3.50 (d, J=13.2 Hz, 2H), 3.14 (dt, J₁=13.6 Hz, J₂=2.8 Hz, 2H), 2.25 (d, J=12.8 Hz, 2H), 1.85~1.75 (m, 3H), 1.09 (d, J=6.8 Hz, 6H).

Step C—Preparation of Compound 2

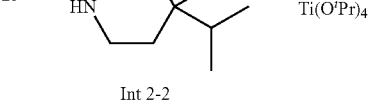

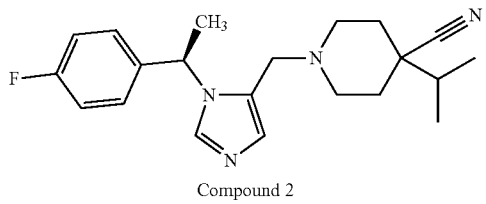

To a stirred suspension of compound Int 2-2 (0.5 g) in 15 mL of dry THF was added compound Int 1-4 (0.37 g, 1.69 mmol), excess Ti(OPr)₄, MgSO₄ and Na₂CO₃. The mixture was stirred at 70° C. oil bath for 4 h. The mixture was cooled to room temperature, then to the stirring mixture suspension was added excess NaBH(OAc)₃ and stirred for 2 h. The mixture was filtrated and concentrated. The residue was re-dissolved in 5 mL methanol filtrated and purified by pre-HPLC to afford white solid 357 mg. Yield: 54.2%. MS (ESI) m/z (M+1): 355. ¹H-NMR (CD₃OD) δ 9.36 (s, 1H), 7.88 (s, 2H), 7.32 (dd, J₁=5.2 Hz, J₂=3.2 Hz, 2H), 7.14 (t, J=8.4 Hz, 2H), 5.99 (dd, J₁=6.0 Hz, J₂=7.2 Hz, 1H), 4.28 (d, J=15.2 Hz, 1H), 4.12 (d, J=15.2 Hz, 1H), 3.48 (d, J=11.6 Hz, 1H), 3.40 (d, J=12.0 Hz, 1H), 2.99 (t, J=12.8 Hz, 1H), 2.82 (t, J=12.4 Hz, 1H), 2.14 (t, J=12.8 Hz, 2H), 1.94 (d, J=6.8 Hz, 3H), 1.82 (t, J=13.2 Hz, 2H), 1.78~1.68 (m, 1H), 1.04 (d, J=6.4 Hz, 6H).

The following compounds 3-8 were prepared using a protocol similar to that described in Examples 1 and 2 above.

| Cmpd | Structure | IUPAC name | M + 1 | ¹H NMR |
|---|---|---|---|---|
| 3 | 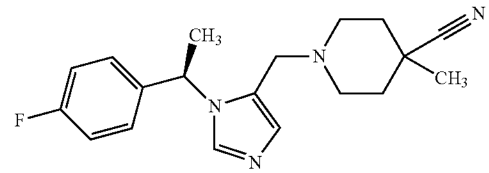 [SMILES: C[C@H](c1ccc(F)cc1)n1cncc1CN1CCC(C)(C#N)CC1] | (R)-1-((1-(1-(4-fluorophenyl)ethyl)-1H-imidazol-5-yl)methyl)-4-methylpiperidine-4-carbonitrile | 327 | CD$_3$OD: δ 9.22 (s, 1H), 7.62 (s, 1H), 7.30~7.27 (m, 2H), 7.16~7.12 (m, 2H), 6.98 (q, J = 6.8 Hz, 1H), 3.76~3.73 (m, 1H), 3.59~3.55 (m, 1H), 2.95~2.83 (m, 2H), 2.46~2.36 (m, 2H), 1.91 (d, J = 6.8 Hz, 5H), 1.60~1.41 (m, 2H), 1.34 (s, 3H). |
| 4 | 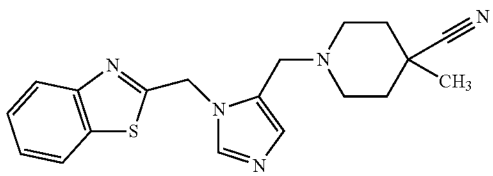 [SMILES: CC1(C#N)CCN(Cc2cncn2Cc2nc3ccccc3s2)CC1] | 1-((1-(benzo[d]thiazol-2-ylmethyl)-1H-imidazol-5-yl)methyl)-4-methylpiperidine-4-carbonitrile | 352 | CD$_3$OD: δ 9.22 (s, 1H), 8.01 (d, J = 7.6 Hz, 1H), 7.90 (d, J = 8.0 Hz, 1H), 7.68 (s, 1H), 7.52 (t, J = 7.6 Hz, 1H), 7.45 (t, J = 7.6 Hz, 1H), 6.02 (m, 2H), 3.89 (m, 2H), 2.91~2.89 (m, 2H), 2.42~2.36 (m, 2H), 1.69 (d, J = 13.2 Hz, 2H), 1.03 (m, 5H). |
| 5 | 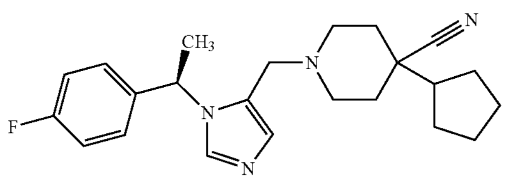 [SMILES: C[C@H](c1ccc(F)cc1)n1cncc1CN1CCC(C#N)(C2CCCC2)CC1] | (R)-4-cyclopentyl-1-((1-(1-(4-fluorophenyl)ethyl)-1H-imidazol-5-yl)methyl)piperidine-4-carbonitrile | 380 | CD$_3$OD: δ 9.24 (d, J = 14.0 Hz, 1H), 7.75~7.62 (m, 1H), 7.30~7.27 (m, 2H), 7.14 (t, J = 8.8 Hz, 2H), 5.97 (q, J = 6.8 Hz, 1H), 3.87~3.71 (m, 2H), 3.17~2.92 (m, 2H), 2.58~2.41 (m, 2H), 2.00~1.68 (m, 8H), 1.61~1.58 (m, 6H), 1.39 (s, 2H). |
| 6 | 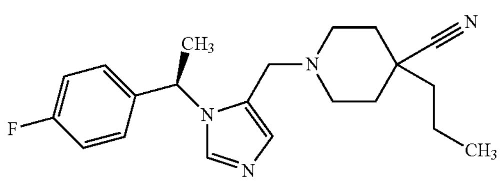 [SMILES: CCCC1(C#N)CCN(Cc2cncn2[C@H](C)c2ccc(F)cc2)CC1] | (R)-1-((1-(1-(4-fluorophenyl)ethyl)-1H-imidazol-5-yl)methyl)-4-propylpiperidine-4-carbonitrile | 355 | CD$_3$OD: δ 9.28 (s, 1H), 7.74 (s, 1H), 7.30 (dd, J$_1$ = 5.2 Hz, J$_2$ = 2.4 Hz, 2H), 7.14 (t, J = 8.4 Hz, 2H), 5.97 (q, J = 6.8 Hz, 1H), 3.99 (d, J = 14.8 Hz, 1H), 3.82 (d, J = 14.8 Hz, 1H), 3.13 (s, 2H), 2.68 (t, J = 12.0 Hz, 1H), 2.59 (t, J = 12.0 Hz, 1H), 2.00 (d, J = 7.2 Hz, 2H), 1.92 (d, J = 7.2 Hz, 3H), 1.69~1.46 (m, 6H), 0.97 (t, J = 6.8 Hz, 3H). |
| 7 | 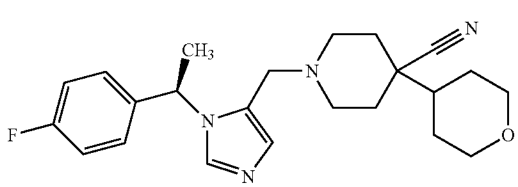 [SMILES: C[C@H](c1ccc(F)cc1)n1cncc1CN1CCC(C#N)(C2CCOCC2)CC1] | (R)-1-((1-(1-(4-fluorophenyl)ethyl)-1H-imidazol-5-yl)methyl)-4-(tetrahydro-2H-pyran-4-yl)piperidine-4-carbonitrile | 397 | CD$_3$OD: δ 9.26 (s, 1H), 7.69 (s, 1H), 7.29 (s, 2H), 7.15 (t, J = 8.0 Hz, 2H), 5.97 (d, J = 6.8 Hz, 1H), 3.99 (d, J = 8.4 Hz, 2H), 3.90 (d, J = 14.8 Hz, 1H), 3.72 (d, J = 14.8 Hz, 1H), 3.38 (t, J = 12.0 Hz, 2H), 3.09 (dd, J$_1$ = 12.0 Hz, J$_2$ = 8.8 Hz, 2H), 2.53 (qu, J = 13.6 Hz, 2H), 2.02 (d, J = 12.8 Hz, 2H), 1.92 (d, J = 6.8 Hz, 3H), 1.71 (d, J = 12.4 Hz, 2H), 1.62 (t, J = 11.2 Hz, 2H), 1.48 (t, J = 12.8 Hz, 2H). |

| Cmpd | Structure | IUPAC name | M + 1 | ¹H NMR |
|---|---|---|---|---|
| 8 | (structure) | (R)-1-((1-(1-(4-fluorophenyl)ethyl)-1H-imidazol-5-yl)methyl)-4-isobutylpiperidine-4-carbonitrile | 369 | CD$_3$OD: δ 9.22 (d, J = 9.6 Hz, 1H), 7.64~7.59 (m, 1H), 7.27 (dd, J$_1$ = 4.8 Hz, J$_2$ = 3.2 Hz, 2H), 7.14 (t, J = 8.4 Hz, 2H), 5.98 (q, J = 7.2 Hz, 1H), 3.81~3.45 (m, 2H), 2.99~2.82 (m, 2H), 2.54~2.35 (m, 2H), 1.92~1.81 (m, 6H), 1.59~1.30 (m, 4H), 1.00 (d, J = 6.8 Hz, 6H). |

Example 9

(R)-3-ethyl-5-(1-((1-(1-(4-fluorophenyl)ethyl)-1H-imidazol-5-yl)methyl)-4-methylpiperidin-4-yl)-1,2,4-oxadiazole (Compound 9)

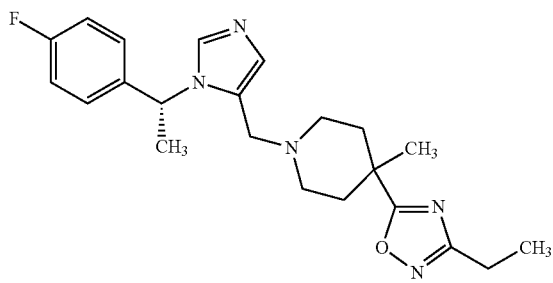 [SMILES: CCc1noc(C2(C)CCN(Cc3cncn3[C@H](C)c3ccc(F)cc3)CC2)n1]

Step A—Preparation of Int 9-1

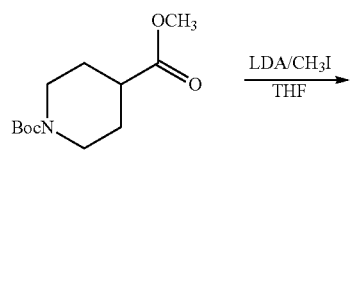

To the solution of 2M LDA (39 mL, 77.12 mmol) in THF (150 mL) was added 1-tert-butyl 4-methyl piperidine-1,4-dicarboxylate (15 g, 61.73 mmol) at −70° C. The reaction mixture was stirred at −70° C. for 2 hours, then a solution of MeI (17 g, 122.2 mmol) in DMF (30 mL) was added. The mixture was allowed to warm to room temperature and stirred overnight. The mixture was poured into H$_2$O (100 mL) and extracted with EtOAc (100 mL×3), the combined organic layer was washed with aqueous saturated sodium bicarbonate (100 mL) and brine (100 mL), dried over sodium sulfate and concentrated. The crude mixture was purified with column chromatography (PE:EA=10:1) to give Int 9-1 (10 g, 63%). ¹H NMR (CDCl$_3$): δ 3.69-3.73 (m, 2H), 3.68 (s, 3H), 2.94-2.99 (m, 2H), 2.02-2.06 (m, 2H), 1.43 (s, 9H) 1.32-1.36 (m, 2H), 1.18 (s, 3H). MS (APCI): M/Z (M+1) 258.2.

Step B—Preparation of Int 9-2

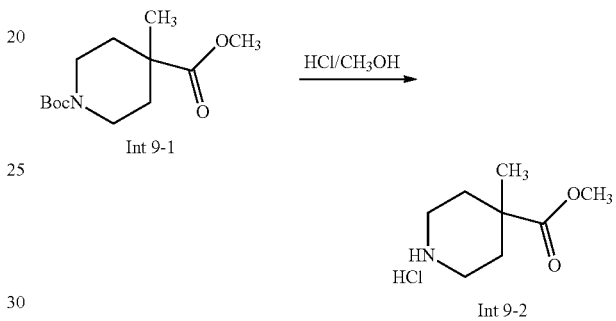

To the solution of Int 9-1 (7.0 g, 27.24 mmol) in 4M HCl/MeOH (20 mL) was heated to 60° C. overnight. The mixture was concentrated in vacuum to give Int 9-2 (4.6 g, 88%). ¹H NMR (CD$_3$OD): δ 3.74 (s, 3H), 3.25-3.36 (m, 2H), 2.94-3.02 (m, 2H), 2.52-2.60 (m, 2H), 1.61-1.70 (m, 2H) 1.27 (s, 3H). MS (APCI): M/Z (M+1) 158.2.

Step C—Preparation of Int 9-3

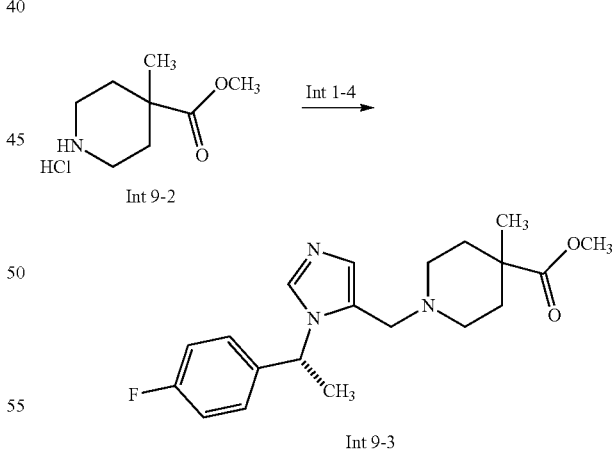

To the solution of Int 9-2 (1.0 g, 5.59 mmol) in THF (20 mL) was added NaHCO$_3$ (570 mg, 6.89 mmol), Int 1-4 (885 mg, 5.59 mmol) and Ti(EtO)$_4$ (3.14 g, 13.78 mmol). The reaction mixture was heated to 80° C. overnight, NaBH(AcO)$_3$ (1.95 g, 9.18 mmol) was added at room temperature and stirred for 4 hours. The mixture was poured into H$_2$O (200 mL) and extracted with EtOAc (200 mL×3), the combined organic layer washed with aqueous saturated sodium bicarbonate (100 mL) and brine (100 mL), dried over sodium sulfate and concentrated. The crude mixture purified by column chromatography (PE:EA=10:1) to give Int 9-3 (1.0 g, 62%). $^1$H NMR (CDCl$_3$): δ 7.58 (s, 1H), 6.91-7.01 (m, 4H), 6.81 (s, 1H), 6.65-6.67 (m, 1H), 4.93-4.96 (m, 1H) 3.61 (s, 1H), 3.11 (q, J=13.2 Hz, 2H), 2.35-2.45 (m, 2H), 1.91-2.00 (m, 4H) 1.74 (d, J=7.6 Hz, 3H) 1.14 (s, 3H) 1.06 (s, 3H). MS (APCI): M/Z (M+1) 360.2.

Step D—Preparation of Compound 9

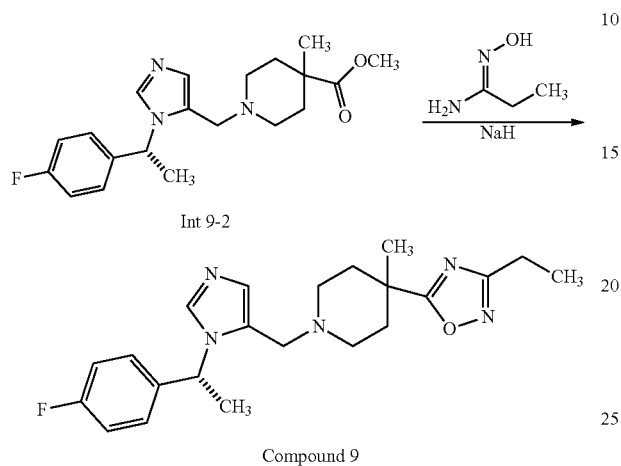

Compound 9

To a mixture of NaH (34 mg, 0.84 mmol) in THF (3 mL) was added N'-hydroxypropionimidamide (74 mg, 0.84 mmol), the mixture was stirred at room temperature for 1 hour, and Int 9-2 (300 mg, 0.84 mmol) was added, the mixture was stirred at 100° C. for 12 hours. The mixture was concentrated and purified by p-HPLC to give compound 9 (60 mg, yield 18%). $^1$H NMR (CD$_3$OD): δ 9.28 (s, 1H), 7.78 (s, 1H), 7.27-7.31 (m, 2H), 7.12-7.16 (m, 2H), 5.94 (q, J=7.0 Hz, 1H), 4.10 (d, J=15.2 Hz, 1H), 3.96 (d, J=14.8 Hz, 1H), 3.18-3.19 (m, 2H), 2.72-2.77 (m, 4H), 2.35-2.42 (m, 2H), 1.92-1.98 (m, 5H), 1.39 (s, 3H), 1.30 (t, J=7.4 Hz, 3H). MS (APCI): M/Z (M+1) 398.2

The following compounds 10-11 were prepared using a protocol similar to that described in Example 9 above.

Example 12

1-((1-(1-(4-cyanophenyl)cyclopropyl)-1H-imidazol-5-yl)methyl)-4-(4-fluorophenyl)piperidine-4-carbonitrile (Compound 12)

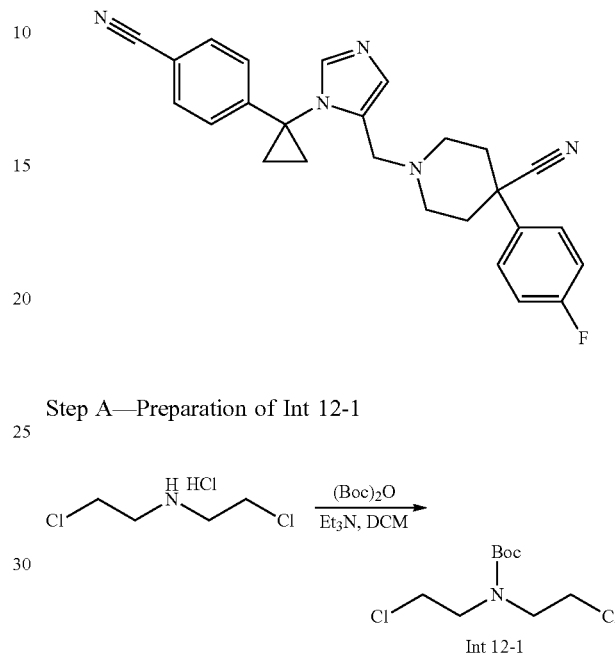

Step A—Preparation of Int 12-1

Bis(2-chloroethyl)amine hydrochloride (8.72 g, 48.8 mmol, 1 eq) was dispersed in 150 mL DCM, then 3 eq Et$_3$N (about 15 mL) was added to the stirring mixture. Excess (Boc)$_2$O was added to the stirring mixture in ice bath and then the mixture was stirred at room temperature for 1.5 h. The mixture was washed by water, dilute citric acid solution, saturated Na$_2$CO$_3$ solution in turn. The organic layer was

| Cmpd | Structure | IUPAC name | M + 1 | $^1$H NMR |
|---|---|---|---|---|
| 10 | 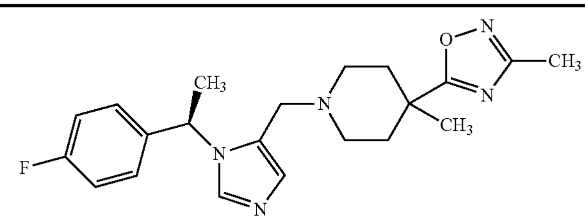 | (R)-5-(1-((1-(1-(4-fluorophenyl)ethyl)-1H-imidazol-5-yl)methyl)-4-methylpiperidin-4-yl)-3-methyl-1,2,4-oxadiazole | 384 | CD$_3$OD: δ 9.21 (s, 1H), 7.73 (s, 1H), 7.19-7.22 (m, 2H), 7.05 (t, J = 8.8 Hz, 2H), 5.85 (q, J = 6.8 Hz, 1H), 4.00-4.02 (m, 2H), 3.14-3.21 (m, 2H), 2.79-2.84 (m, 1H), 2.65-2.67 (m, 1H), 2.28-2.35 (m, 5H), 1.83-1.93 (m, 5H), 1.38 (s, 3H). |
| 11 | | (R)-5-(1-((1-(1-(4-fluorophenyl)ethyl)-1H-imidazol-5-yl)methyl)-4-methylpiperidin-4-yl)-3-isopropyl-1,2,4-oxadiazole | 412 | CD$_3$OD: δ 9.18 (s, 1H), 7.63 (s, 1H), 7.27-7.30 (m, 2H), 7.14 (t, J = 8.8 Hz, 2H), 5.96 (q, J = 7.0 Hz, 1H), 3.83 (d, J = 15.2 Hz, 1H), 3.67 (d, J = 15.2 Hz, 1H), 3.01-3.08 (m, 1H), 2.92-2.94 (m, 1H), 2.30-2.52 (m, 4H), 1.92 (d, J = 7.2 Hz, 3H), 1.74-1.84 (m, 2H), 1.35 (s, 3H), 1.31 (t, J = 7.2 Hz, 6H). | dried over Na₂SO₄, filtrated and purified by column to afford 8.3 g oil residue. ¹H NMR (CDCl₃) δ 3.67~3.58 (m, 8H), 1.46 (s, 9H).

Step B—Preparation of Int 12-2

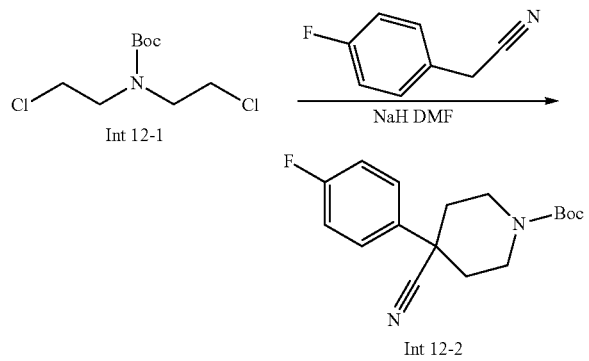

To a mixture solution of compound Int 12-1 (1.21 g, 5 mmol, 1 eq) and 4-fluorophenyl acetonitrile (675 mg, 5 mmol, 1 eq) in anhydrous DMF was added NaH (400 mg, 60% in mineral oil, 10 mmol, 2 eq) in portions in ice bath. Then the mixture was stirred in ice bath for 2 h. The mixture was quenched by saturated NH₄Cl solution, extracted by EtOAc. The organic layer was dried, filtrated and concentrated. The residue was purified by column to afford 1.01 g white solid. ¹H NMR (CDCl₃) δ 7.4~47.41 (m, 2H), 7.11~7.06 (m, 2H), 4.26 (br, 2H), 3.16 (br, 2H), 2.07 (d, J=12.8 Hz, 2H), 1.89 (dt, J₁=4.0 Hz, J₁=9.2 Hz, 2H), 1.46 (s, 9H).

Step C—Preparation of Int 12-3

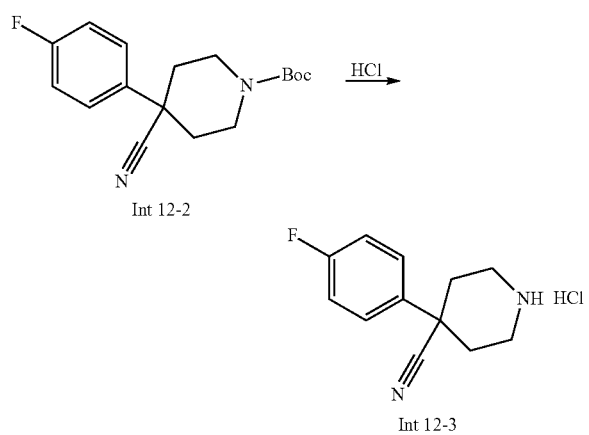

To a solution of Int 12-2 (0.35 g, 1.16 mmol) in EtOAc (5 mL) was carefully added 10 mL HCl/EtOAc. The mixture was stirred at room temperature for 1 h. The solvent was removed by reducing pressure to afford 0.28 g white solid. The filtrate was concentrated to dryness which was used directly in the next step directly. (Yield: 100%).

Step D—Preparation of Compound 12

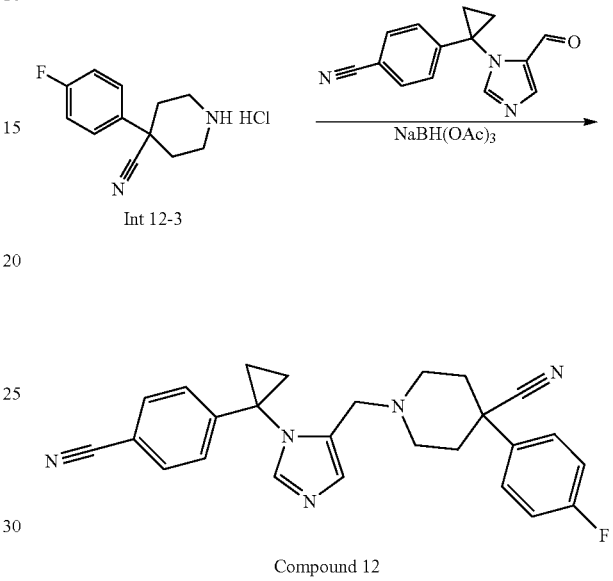

To a stirred suspension of Int 12-3 (the residue of step C, 0.28 g) in 30 mL of dry THF was added compound 6 (0.2886 g, 1.21 mmol), excess Ti(OPr)₄, MgSO₄ and Na₂CO₃. The mixture was stirred at 70° C. for 4 h then the mixture was cooled to room temperature, then to the stirring mixture suspension was added excess NaBH(OAc)₃ and stirred for 2 h. The mixture was filtrated and concentrated. The residue was re-dissolved in 5 mL methanol and purified by pre-HPLC to afford white solid 302.5 mg. MS (ESI) m/z (M+1): 426.0. ¹H NMR (CD₃OD) δ 9.37 (s, 1H), 7.71 (d, J=8.4 Hz, 1H), 7.66 (s, 1H), 7.32 (t, J=6.4 Hz, 2H), 7.14 (t, J=8.4 Hz, 2H), 7.09 (d, J=8.8 Hz, 2H), 3.71~3.66 (m, 2H), 2.88 (s, 2H), 2.43 (s, 2H), 2.00 (s, 2H), 1.87 (s, 4H), 1.35 (s, 2H).

The following compounds 13-15 were prepared using a protocol similar to that described in Example 12 above.

| Cmpd | Structure | IUPAC name | M + 1 | ¹H NMR |
|---|---|---|---|---|
| 13 | 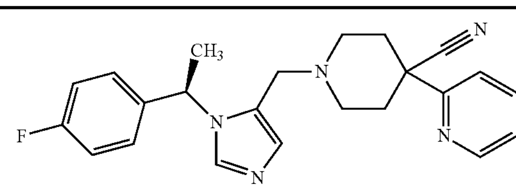 | (R)-1-((1-(1-(4-fluorophenyl)ethyl)-1H-imidazol-5-yl)methyl)-4-(pyridin-2-yl)piperidine-4-carbonitrile | 390 | CD₃OD: δ 9.32 (s, 1H), 8.59 (s, 1H), 7.88 (t, J = 7.6 Hz, 1H), 7.81 (s, 1H), 7.62 (d, J = 8.0 Hz, 1H), 7.40~7.32 (m, 3H), 7.16 (t, J = 8.4 Hz, 2H), 6.04 (d, J = 6.0 Hz, 1H), 4.14~3.93 (m, 2H), 3.38~3.26 (m, 2H), 2.95~2.75 (m, 2H), 2.41~2.26 (m, 4H), 1.95 (d, J = 7.6 Hz, 3H). |

| Cmpd | Structure | IUPAC name | M + 1 | $^1$H NMR |
|---|---|---|---|---|
| 14 | 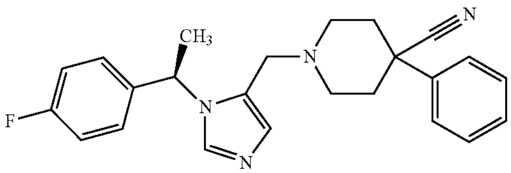 [SMILES: C[C@H](c1ccc(F)cc1)n1cncc1CN1CCC(C#N)(c2ccccn2)CC1] | (R)-1-((1-(1-(4-fluorophenyl)ethyl)-1H-imidazol-5-yl)methyl)-4-phenylpiperidine-4-carbonitrile | 389 | CD$_3$OD: δ 9.28 (d, J = 0.8 Hz, 1H), 7.67 (s, 1H), 7.47~7.39 (m, 4H), 7.36~7.28 (m, 3H), 7.14 (t, J = 8.8 Hz, 2H), 6.01 (d, J = 6.8 Hz, 1H), 3.83 (d, J = 14.4 Hz, 1H), 3.61 (d, J = 14.8 Hz, 1H), 3.09 (d, J = 11.6 Hz, 1H), 2.95 (d, J = 12.4 Hz, 1H), 2.61~2.55 (m, 2H), 2.14~2.03 (m, 3H), 1.93 (d, J = 6.8 Hz, 3H), 1.89~1.84 (m, 1H). |
| 15 | 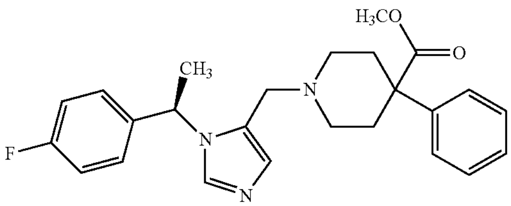 [SMILES: COC(=O)C1(c2ccccc2)CCN(Cc2cncn2[C@H](C)c2ccc(F)cc2)CC1] | (R)-methyl 1-((1-(1-(4-fluorophenyl)ethyl)-1H-imidazol-5-yl)methyl)-4-phenylpiperidine-4-carboxylate | 422 | CDCl$_3$: δ 8.60 (s, 1H), 7.73~7.67 (m, 1H), 7.29 (d, J = 6.8 Hz, 2H), 7.20~7.19 (m, 2H), 7.10 (d, J = 7.2 Hz, 4H), 5.94 (m, 1H), 3.85~3.81 (m, 2H), 3.64~3.63 (m, 2H), 3.25 (m, 2H), 2.82~2.59 (m, 4H), 2.19 (m, 2H), 1.82 (d, J = 6.8 Hz, 3H). |

Example 16

5-((3,3-difluoropyrrolidin-1-yl)methyl)-1-(1-(4'-fluoro-[1,1'-biphenyl]-2-yl)ethyl)-1H-imidazole (Compound 16)

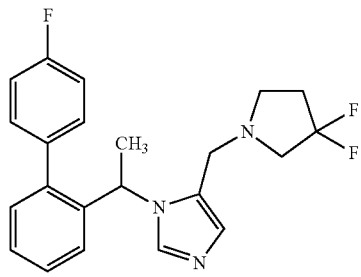 [SMILES: CC(c1ccccc1-c1ccc(F)cc1)n1cncc1CN1CCC(F)(F)C1]

Step A—Preparation of Int 16-1

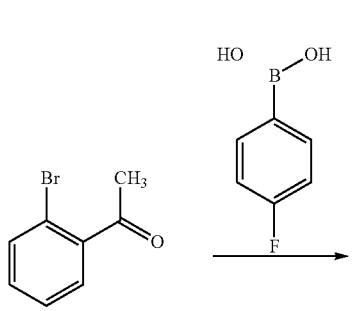

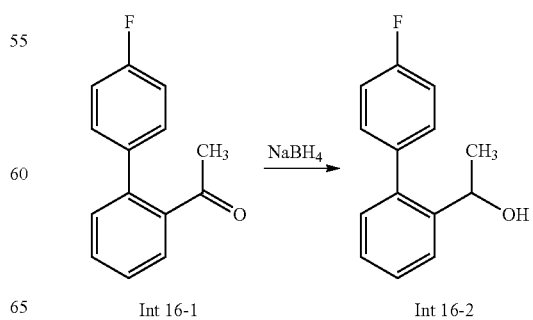

A degassed mixture of 2-bromoacetophenone (11 g, 54.9 mmol), phenylboronic acid (8.0 g, 65.9 mmol), Pd(dppf)Cl$_2$ (4 g, 5.49 mmol) and sodium carbonate (11.6 mg, 110 mmol) was added to DME (100 mL) and water (20 mL) and the mixture was heated to 80° C. overnight. The reaction mixture was cooled and filtered and the filtrate was evaporated. The residue was purified by column chromatography (PE:EtOAc=100:1) to give Int 16-1 (8.0 g). $^1$H NMR (CDCl$_3$): 7.47-7.54 (m, 2H), 7.38-7.42 (m, 1H), 7.24-7.34 (m, 3H), 7.08-7.12 (m, 2H), 2.03 (s, 1H). MS (APCI): M/Z (M+1) 215.1.

Step B—Preparation of Int 16-2

To a solution of Int 16-1 (4 g, 18.6 mmol) in MeOH (40 mL) was added NaBH$_4$ (0.825 g, 22.4 mmol) at 0° C. The mixture was stirred at room temperature for 30 mins and quenched with sat. NH$_4$Cl solution (20 mL), extracted with EtOAc (3×). The organic extracts were washed with water (2×) and brine (1×), then dried over Na$_2$SO$_4$. The solids were removed by filtration and the filtrate was concentrated to give Int 16-2 (3.5 g). $^1$H NMR (CDCl$_3$): δ 7.64-7.66 (m, 1H), 7.38-7.42 (m, 1H), 7.24-7.31 (m, 3H), 7.15-7.17 (m, 1H), 7.06-7.11 (m, 2H), 4.09-4.94 (m, 1H), 1.39 (d, J=6 Hz, 3H). MS (APCI): M/Z (M+1) 217.1.

Step C—Preparation of Int 16-3

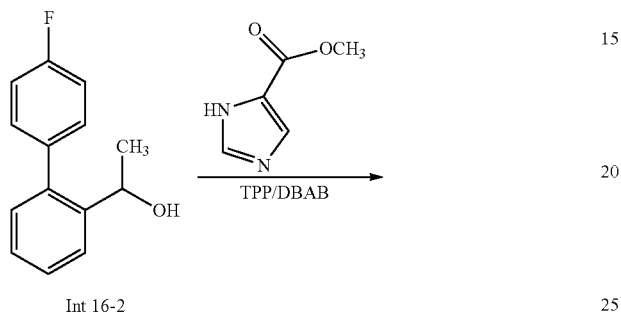

Int 16-2

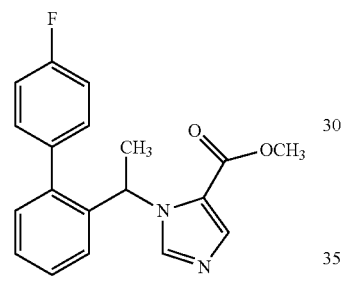

Int 16-3

To a solution of methyl 1H-imidazole-5-carboxylate (3.79 g, 30.09 mmol) and PPh$_3$ (9.46 g, 36.11 mmol) in THF (60 mL) was added Int 16-2 (6.5 g, 30.09 mmol) at −20° C., then a solution of DBAD (8.3 g, 36.11 mmol) in THF (10 mL) was added. The mixture was stirred at this temperature for 2 hours. Water (30 mL) was added to the solution and extracted with EtOAc (3×). The combined organic phase was dried over MgSO$_4$ and concentrated. The residue was purified column chromatographic on silica gel (EtOAc) to give Int 16-3 (2 g, 20%). $^1$H NMR (CDCl$_3$): δ 7.60 (s, 1H), 7.43 (s, 1H), 7.34-7.39 (m, 2H), 7.17-7.24 (m, 2H), 6.95-7.06 (m, 4H), 6.67-6.32 (m, 1H), 3.70 (s, 3H), 1.39 (d, J=6.4 Hz, 3H). MS (APCI): M/Z (M+1) 325.1.

Step D—Preparation of Int 16-4

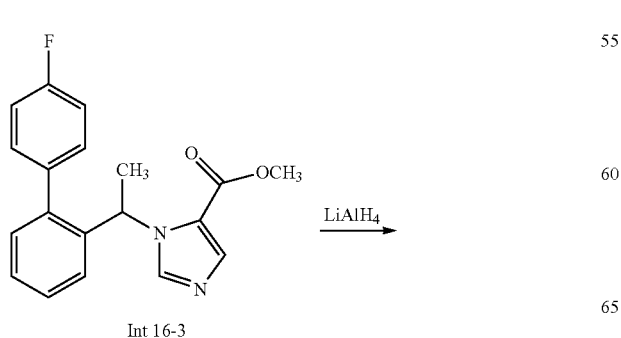

Int 16-3

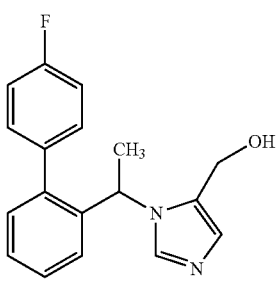

Int 16-4

To a suspension of LiAlH$_4$ (117 mg, 3.088 mmol) in dry THF (15 mL) at 0° C. was added a solution of Int 16-3 (500 mg, 1.54 mmol) in (5 mL) THF dropwise. The mixture was stirred at −78° C. for 2 hours then quenched with water (0.3 mL), 15% NaOH solution (0.3 mL) and water (2 mL). The mixture was diluted with EtOAc (20 mL) and the organic phase was separated and dried over MgSO$_4$. The filtrate was concentrated and the residue was purified by HPLC to give Int 16-4 (400 mg). $^1$H NMR (CD$_3$OD): δ 8.80 (s, 1H), 7.34-7.48 (m, 9H), 5.80-5.86 (m, 1H), 4.18 (d, J=14 Hz, 1H), 3.88 (d, J=14 Hz, 1H), 1.88 (d, J=7.2 Hz, 3H). MS (APCI): M/Z (M+1) 297.1.

Step E—Preparation of Int 16-5

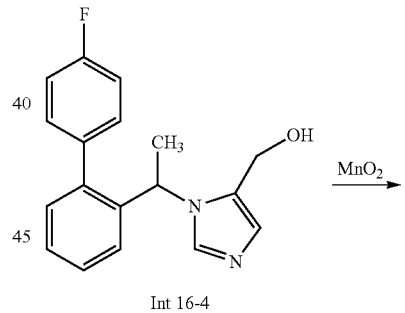

Int 16-4

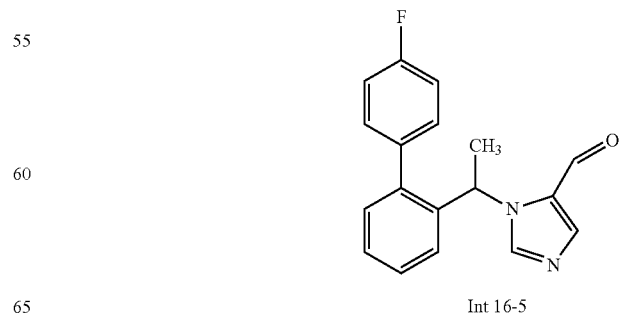

Int 16-5

To a solution of Int 16-4 (500 mg, 1.68 mmol) in dioxane (10 mL) was added MnO₂ (1.46 mg, 16.83 mmol). The mixture was heated to reflux overnight then cooled and filtered. The filtrate was dried over MgSO₄ and concentrated to give Int 16-5 (400 mg) which was used into the next step without further purification. MS (APCI): M/Z (M+1) 295.1.

Step F—Preparation of Compound 16

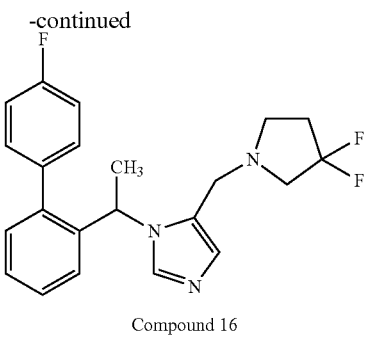

Compound 16

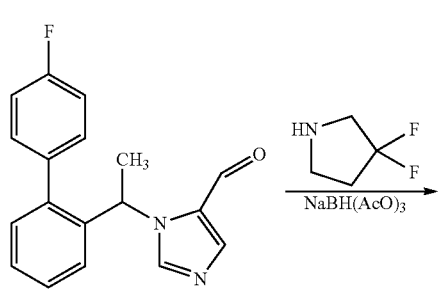

A mixture of Int 16-5 (150 mg, 0.51 mmol), NaBH(OAc)₃ (216 mg, 1.02 mmol), DIEA (130 mg, 1.02 mmol), and 3,3-difluoropyrrolidine (60 mg, 0.56 mmol) in DCM (5 mL) was stirred at room temperature overnight, the reaction mixture was concentrated and purified by HPLC to give Compound 16 (99 mg, 55.8%). ¹H NMR (CD₃OD) δ: 8.94 (s, 1H), 7.44~7.54 (m, 4H), 7.21-7.32 (m, 5H), 6.00 (q, J=6.8 Hz, 1H), 3.31~3.34 (m, 2H), 2.52~2.80 (m, 4H), 2.14~2.25 (m, 2H), 1.84 (d, J=6.8 Hz, 3H). MS (APCI): M/Z (M+1) 386.1.

The following compounds 17-22 were prepared using a protocol similar to that described in Example 16 above using a substituted cyclic amine and an appropriately substituted imidazole carboxaldehyde.

| Cmpd | Structure | IUPAC name | M + 1 | ¹H NMR |
|---|---|---|---|---|
| 17 | 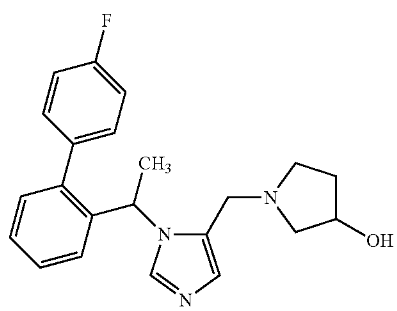 [SMILES: CC(c1ccccc1-c1ccc(F)cc1)n1cncc1CN1CCC(O)C1] | 1-((1-(1-(4'-fluoro-[1,1'-biphenyl]-2-yl)ethyl)-1H-imidazol-5-yl)methyl)pyrrolidin-3-ol | 366 | CD₃OD δ: 9.19 (d, J = 5.2 Hz, 1H), 7.78 (s, 1H), 7.38~7.46 (m, 4H), 7.25-7.32 (m, 4H), 5.78 (q, J = 3.6 Hz, 1H), 4.46 (s, 1H), 4.04~4.09 (m, 1H), 3.86~3.91 (m, 1H), 3.15~3.23 (m, 3H), 3.02~3.06 (m, 1H), 2.08~2.17 (m, 1H), 1.96~2.02 (m, 4H). |
| 18 | 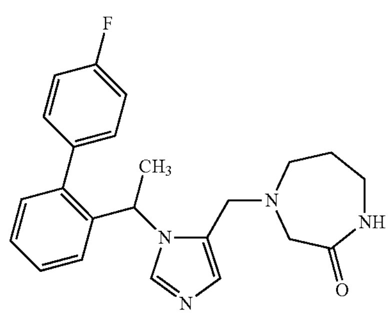 [SMILES: CC(c1ccccc1-c1ccc(F)cc1)n1cncc1CN1CCCNC(=O)C1] | 4-((1-(1-(4'-fluoro-[1,1'-biphenyl]-2-yl)ethyl)-1H-imidazol-5-yl)methyl)-1,4-diazepan-2-one | 393 | CD₃OD δ 8.85 (s, 1H), 7.44~7.48 (m, 6H), 7.34 (s, 1H), 7.17~7.25 (m, 5H), 5.84 (q, J = 6.8 Hz, 1H), 3.20~3.33 (m, 5H), 2.97 (d, J = 14.8 Hz, 1H), 2.64~2.76 (m, 2H), 1.92 (d, J = 6.8 Hz, 3H), 1.58~1.61 (m, 2H). |

| Cmpd | Structure | IUPAC name | M + 1 | ¹H NMR |
|---|---|---|---|---|
| 19 | 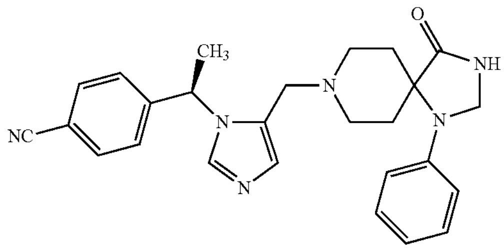 [SMILES: C[C@H](c1ccc(C#N)cc1)n1cncc1CN1CCC2(CC1)C(=O)NCN2c1ccccc1] | (R)-4-(1-(5-((4-oxo-1-phenyl-1,3,8-triazaspiro[4.5]decan-8-yl)methyl)-1H-imidazol-1-yl)ethyl)benzonitrile | | |
| 20 | 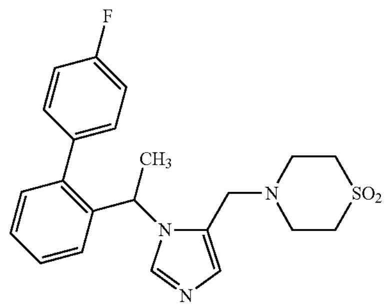 [SMILES: CC(c1ccccc1-c1ccc(F)cc1)n1cncc1CN1CCS(=O)(=O)CC1] | 4-((1-(1-(4'-fluoro-[1,1'-biphenyl]-2-yl)ethyl)-1H-imidazol-5-yl)methyl)thiomorpholin 1,1-dioxide | 414 | CD₃OD δ: 7.46 (t, J = 3.2 Hz, 4H), 7.19~7.28 (m, 5H), 5.92 (q, J = 6.8 Hz, 1H), 3.29 (t, J = 6.8 Hz, 3H), 2.88~3.04 (m, 5H), 2.62~2.78 (m, 4H), 1.96 (d, J = 6.8 Hz, 3H). |
| 21 | 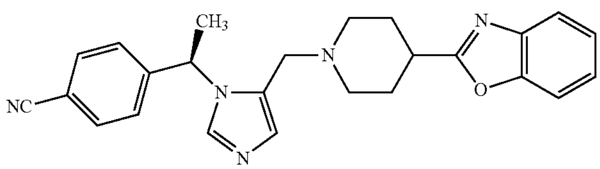 | (R)-4-(1-(5-((4-(benzo[d]oxazol-2-yl)piperidin-1-yl)methyl)-1H-imidazol-1-yl)ethyl)benzonitrile | 412 | CD₃OD δ 8.10 (s, 1H), 7.72 (d, J = 8.0 Hz, 2H), 7.63~7.58 (m, 2H), 7.34~7.30 (m, 4H), 6.97 (s, 1H), 5.87 (q, J = 7.2 Hz, 1H), 3.50 (d, J = 13.7 Hz, 1H), 3.25~3.22 (m, 1H), 2.90~2.87 (m, 2H), 2.67~2.63 (m, 1H), 2.11~1.93 (m, 3H), 1.89~1.87 (m, 4H), 1.77~1.64 (m, 1H), 1.41~1.38 (m, 1H). |
| 22 | 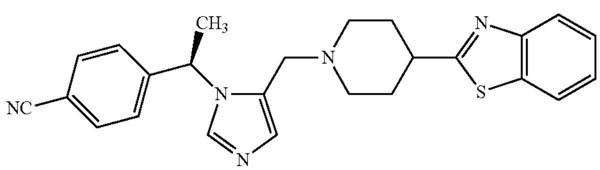 [SMILES: C[C@H](c1ccc(C#N)cc1)n1cncc1CN1CCC(c2nc3ccccc3o2)CC1] | (R)-4-(1-(5-((4-(benzo[d]thiazol-2-yl)piperidin-1-yl)methyl)-1H-imidazol-1-yl)ethyl)benzonitrile | 428 | CD₃OD δ: 9.40 (s, 1H), 7.95 (t, J = 7.2 Hz, 2H), 7.92 (s, 1H), 7.78 (d, J = 8.4 Hz, 2H), 7.51 (t, J = 8.4 Hz, 1H), 7.45~7.40 (m, 3H), 6.07 (q, J = 6.8 Hz, 1H), 4.30 (d, J = 14.4 Hz, 1H), 4.07 (d, J = 14.4 Hz, 1H), 3.52~3.39 (m, 3H), 3.05~3.00 (m, 2H), 2.36~2.31 (m, 2H), 2.12~2.00 (m, 2H), 1.98 (d, J = 8.4 Hz, 3H). |

Example 23

(R)-2-(4-((1-(1-(4-fluorophenyl)ethyl)-1H-imidazol-5-yl)methyl)piperazin-1-yl)benzo[d]oxazole (Compound 23)

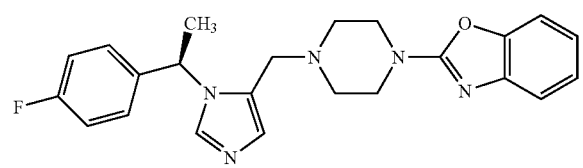 [SMILES: C[C@H](c1ccc(F)cc1)n1cncc1CN1CCN(c2nc3ccccc3o2)CC1]

Step A—Preparation of Compound 23

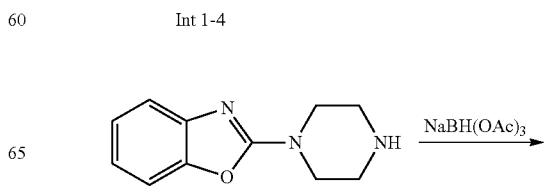

-continued

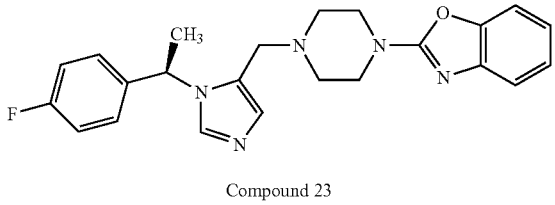

Compound 23

A mixture compound of compound Int 1-4 (100 mg, 0.49 mmol), and 2-(piperazin-1-yl)benzo[d]oxazole (107 mg, 0.49 mmol) in 1,2-dichloromethane was stirred at room temperature for 3 h. NaBH(OAc)$_3$ (311 mg, 1047 mmol) was added and the mixture was stirred for 16 hours, diluted with H$_2$O and extracted with CH$_2$Cl$_2$ (3×5 mL). The combined organic extracts were washed with H$_2$O (3×5 mL) and brine, dried (Na$_2$SO$_4$) and concentrated. The residue was purified by HPLC to afford 50 mg of Compound 23. $^1$H NMR (CD$_3$OD) δ 9 9.23 (s, 1H), 7.60 (s, 1H), 7.35~7.29 (m, 4H), 7.24~7.21 (m, 1H), 7.20~7.10 (m, 3H), 6.06 (d, J=6.8 Hz, 1H), 3.67~3.59 (m, 5H), 3.48 (d, J=14.8 Hz, 1H), 2.64~2.55 (m, 4H), 1.94 (d, J=6.8 Hz, 3H). MS (ESI) m/z (M+1): 406.

The following compounds 24-39 were prepared using a protocol similar to that described in Example 23 using a substituted piperazine and an appropriately substituted imidazole carboxaldehyde (prepared as illustrated in Example 1).

| | | | | |
|---|---|---|---|---|
| 24 | 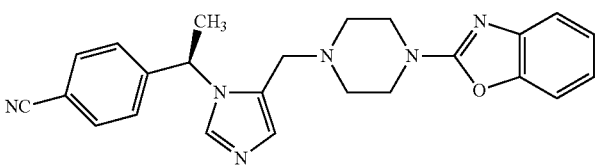 [SMILES: C[C@H](c1ccc(C#N)cc1)n1cncc1CN1CCN(c2nc3ccccc3o2)CC1] | (R)-4-(1-(5-((4-(benzo[d]oxazol-2-yl)piperazin-1-yl)methyl)-1H-imidazol-1-yl)ethyl)benzonitrile | 413 | CD$_3$OD δ: 9.34 (s, 1H), 7.74 (d, J = 8.4 Hz, 2H), 7.67 (s, 1H), 7.43 (d, J = 8.4 Hz, 2H), 7.36 (d, J = 8.0 Hz, 1H), 7.24 (d, J = 7.6 Hz, H), 7.17 (t, J = 7.6 Hz, 1H), 7.12 (t, J = 7.2 Hz, 1H), 6.12 (q, J = 7.2 Hz, 1H), 3.76 (d, J = 14.8 Hz, 1H), 3.78~3.62 (m, 2H), 3.53 (d, J = 14.4 Hz, 1H), 1.97 (d, J = 8.0 Hz, 3H). |
| 25 | 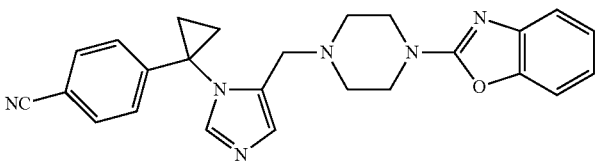 [SMILES: N#Cc1ccc(C2(n3cncc3CN3CCN(c4nc5ccccc5o4)CC3)CC2)cc1] | 4-(1-(5-((4-(benzo[d]oxazol-2-yl)piperazin-1-yl)methyl)-1H-imidazol-1-yl)cyclopropyl)benzonitrile | 425 | CD$_3$OD δ 9.38 (s, 1H), 7.71 (d, J = 8.4 Hz, 2H), 7.66 (s, 1H), 7.31 (d, J = 8.0 Hz, 1H), 7.28 (d, J = 7.2 Hz, 1H), 7.20 (t, J = 7.6 Hz, 1H), 7.18~7.08 (m, 3H), 3.59 (s, 2H), 3.42~3.39 (m, 4H), 2.54~2.52 (m, 4H), 2.03 (s, 2H), 1.88~1.87 (s, 2H). |
| 26 | 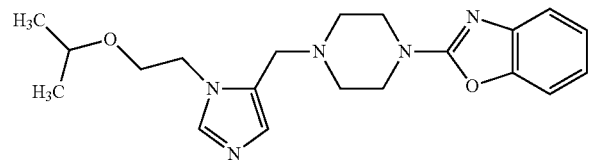 [SMILES: CC(C)OCCn1cncc1CN1CCN(c2nc3ccccc3o2)CC1] | 2-(4-((1-(2-isopropoxyethyl)-1H-imidazol-5-yl)methyl)piperazin-1-yl)benzo[d]oxazole | 370 | CD$_3$OD δ 8.96 (s, 1H), 7.63 (s, 1H), 7.39 (d, J = 8.0 Hz, 1H), 7.33 (d, J = 7.2 Hz, 1H), 7.24 (t, J = 7.6 Hz, 1H), 7.14 (t, J = 8.0 Hz, 1H), 4.52 (t, J = 5.2 Hz, 2H), 4.04 (s, 2H), 3.82~3.78 (m, 6H), 3.59~3.55 (m, 1H), 2.91 (t, J = 5.2 Hz, 4H), 1.09 (d, J = 6.0 Hz, 6H). |
| 27 | 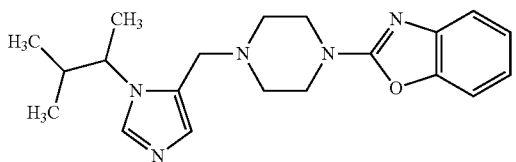 [SMILES: CC(C)C(C)n1cncc1CN1CCN(c2nc3ccccc3o2)CC1] | 2-(4-((1-(3-methylbutan-2-yl)-1H-imidazol-5-yl)methyl)piperazin-1-yl)benzo[d]oxazole | 354 | CD$_3$OD δ 9.17 (s, 1H), 7.61 (s, 1H), 7.38 (d, J = 8.0 Hz, 1H), 7.32 (d, J = 7.6 Hz, 1H), 7.24 (t, J = 7.6 Hz, 1H), 7.14 (t, J = 7.6 Hz, 1H), 4.41~4.44 (m, 1H), 3.90 (s, 2H), 3.78 (t, J = 8.4 Hz, 4H), 2.84~2.83 (m, 4H), 2.20~2.11 (m, 1H), 1.56 (d, J = 6.8 Hz, 3H), 1.04 (d, J = 6.8 Hz, 3H), 0.86 (d, J = 6.8 Hz, 3H). |
| 28 | 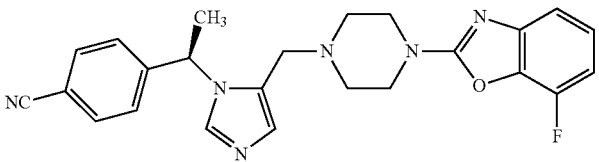 [SMILES: C[C@H](c1ccc(C#N)cc1)n1cncc1CN1CCN(c2nc3cccc(F)c3o2)CC1] | (R)-4-(1-(5-((4-(7-fluorobenzo[d]oxazol-2-yl)piperazin-1-yl)methyl)-1H-imidazol-1-yl)ethyl)benzonitrile | 431 | CD$_3$OD δ 9.31 (s, 1H), 7.79 (d, J = 8.4 Hz, 2H), 7.62 (s, 1H), 7.44 (d, J = 8.0 Hz, 2H), 7.23~7.15 (m, 2H), 6.97~6.92 (m, 1H), 6.13 (q, J = 7.2 Hz, 1H), 3.64 (d, J = 14.4 Hz, 1H), 3.55~3.42 (m, 4H), 3.38 (d, J = 14.8 Hz, 1H), 2.54~2.44 (m, 4H), 2.37 |

| | | | | |
|---|---|---|---|---|
| | | | | (s, 3H), 1.96 (d, J = 7.2 Hz, 3H). |
| 29 | | (R)-4-(1-(5-((4-(7-methylbenzo[d]oxazol-2-yl)piperazin-1-yl)methyl)-1H-imidazol-1-yl)ethyl)benzonitrile | 427 | CD₃OD δ 9.30 (s, 1H), 7.84 (s, 2H), 7.62~7.61 (m, 1H), 7.44 (s, 2H), 7.10~6.93 (m, 3H), 6.13 (m, 1H), 3.66 (d, J = 14.8 Hz, 1H), 3.57~3.50 (m, 2H), 3.40 (d, J = 14.8 Hz, 1H), 3.12 (m, 2H), 2.57~2.49 (m, 4H), 2.40~2.38 (m, 3H), 1.96 (m, 3H). |
| 30 | | (R)-4-(1-(5-((4-(6-fluorobenzo[d]oxazol-2-yl)piperazin-1-yl)methyl)-1H-imidazol-1-yl)ethyl)benzonitrile | 431 | CD₃OD δ 9.31 (s, 1H), 7.79 (d, J = 8.0 Hz, 2H), 7.62 (s, 1H), 7.45 (d, J = 8.4 Hz, 2H), 7.22~7.14 (m, 2H), 6.97~6.92 (m, 1H), 6.14 (q, J = 7.2 Hz, 1H), 3.63 (d, J = 14.4 Hz, 1H), 3.54~3.35 (m, 5H), 2.52~2.43 (m, 4H), 1.96 (d, J = 7.2 Hz, 3H). |
| 31 | | (R)-4-(1-(5-((4-(6,7-difluorobenzo[d]oxazol-2-yl)piperazin-1-yl)methyl)-1H-imidazol-1-yl)ethyl)benzonitrile | 449 | CD₃OD δ 9.31 (s, 1H), 7.79 (d, J = 8.4 Hz, 2H), 7.61 (s, 1H), 7.45 (d, J = 8.4 Hz, 2H), 7.10~6.97 (m, 2H), 6.15 (q, J = 7.2 Hz, 1H), 3.63 (d, J = 14.4 Hz, 1H), 3.57~3.43 (m, 4H), 3.37 (d, J = 14.4 Hz, 1H), 2.56~2.40 (m, 4H), 1.96 (d, J = 7.2 Hz, 3H). |
| 32 | | 2-(4-((1-(1-(tetrahydro-2H-pyran-4-yl)ethyl)-1H-imidazol-5-yl)methyl)piperazin-1-yl)benzo[d]oxazole | 396 | CD₃OD δ 9.16 (s, 1H), 7.56 (s, 1H), 7.34 (d, J = 8.0 Hz, 1H), 7.29 (d, J = 7.6 Hz, 1H), 7.20 (t, J = 7.6 Hz, 1H), 7.11~7.07 (m, 1H), 4.57~4.49 (m, 1H), 4.01 (dd, J1 = 3.6 Hz, J2 = 11.2 Hz, 1H), 3.92 (dd, J1 = 3.6 Hz, J2 = 7.2 Hz, 1H), 3.74~3.71 (m, 6H), 3.44~3.33 (m, 2H), 2.68 (m, 4H), 2.17~2.09 (m, 1H), 1.77 (d, J = 12.8 Hz, 1H), 1.56 (d, J = 6.8 Hz, 3H), 1.50~1.40 (m, 2H), 1.35 (d, J = 12.8 Hz, 1H). |
| 33 | | 2-(4-((1-(2-(pyridin-2-yl)ethyl)-1H-imidazol-5-yl)methyl)piperazin-1-yl)benzo[d]oxazole | 389 | CD₃OD δ 8.82 (s, 1H), 8.58 (s, 1H), 8.14~8.12 (m, 1H), 7.60 (d, J = 7.2 Hz, 2H), 7.48 (s, 1H), 7.25 (d, J = 8.0 Hz, 1H), 7.19 (d, J = 8.0 Hz, 1H), 7.10 (t, J = 7.6 Hz, 1H), 7.03~6.98 (m, 1H), 4.67 (t, J = 7.2 Hz, 2H), 3.77 (s, 2H), 3.66 (s, 4H), 3.52~3.50 (m, 2H), 2.72 (s, 4H). |
| 34 | | 2-(4-((1-(1-(4-(methylsulfonyl)phenyl)ethyl)-1H-imidazol-5-yl)methyl)piperazin-1-yl)benzo[d]oxazole | 466 | CD₃OD δ 9.25 (s, 1H), 7.88 (d, J = 8.4 Hz, 2H), 7.55 (s, 1H), 7.42 (d, J = 8.4 Hz, 2H), 7.27 (d, J = 8.0 Hz, 1H), 7.21 (d, J = 7.6 Hz, 1H), 7.13 (t, J = 7.6 Hz, 1H), 7.06~7.02 (m, 1H), 6.06 (q, J = 6.8 Hz, 1H), 3.62 (d, J = 14.4 Hz, 1H), |

-continued

| | | | | | |
|---|---|---|---|---|---|
| | | | | | 3.50~3.47 (m, 2H), 3.46~3.33 (m, 3H), 2.98 (s, 3H), 2.53~2.39 (m, 4H), 1.89 (d, J = 6.8 Hz, 3H). |
| 35 | | 6,7-difluoro-2-(4-((1-(1-(tetrahydro-2H-pyran-4-yl)ethyl)-1H-imidazol-5-yl)methyl)piperazin-1-yl)benzo[d]oxazole | 432 | | δ 9.28 (s, 1H), 7.75 (s, 1H), 7.30~7.29 (m, 2H), 7.17~7.12 (m, 2H), 5.98~5.96 (m, 1H), 4.05~3.69 (m, 2H), 2.94~2.64 (m, 5H), 2.01~1.91 (m, 7H). |
| 36 | | 2-(4-((1-(3,3,3-trifluoro-2-methylpropyl)-1H-imidazol-5-yl)methyl)piperazin-1-yl)benzo[d]oxazole | 394 | | CD$_3$OD δ 9.13 (s, 1H), 7.64 (s, 1H), 7.39 (d, J = 8.0 Hz, 1H), 7.33 (d, J = 7.2 Hz, 1H), 7.25 (t, J = 7.2 Hz, 1H), 7.16 (t, J = 7.2 Hz, 1H), 4.73 (dd, J1 = 2.8 Hz, J2 = 14.4 Hz, 1H), 4.42 (dd, J1 = 3.6 Hz, J2 = 14.4 Hz, 1H), 3.97 (s, 2H), 3.78~3.75 (m, 4H), 3.38~3.32 (m, 1H), 2.80~2.77 (m, 4H), 1.21 (d, J = 6.8 Hz, 3H). |
| 37 | | 2-(4-((1-(4-fluorophenethyl)-1H-imidazol-5-yl)methyl)piperazin-1-yl)benzo[d]oxazole | 406 | | CD$_3$OD δ 8.78 (s, 1H), 7.59 (s, 1H), 7.41~7.39 (m, 1H), 7.35~7.33 (m, 1H), 7.27~7.24 (m, 1H), 7.20~7.16 (m, 3H), 7.03 (t, J = 8.4 Hz, 2H), 4.58 (t, J = 8.4 Hz, 2H), 3.81 (s, 6H), 3.22 (t, J = 7.2 Hz, 2H), 2.87 (m, 4H). |
| 38 | | (R)-4-(1-(5-((4-(6-methoxybenzo[d]thiazol-2-yl)piperazin-1-yl)methyl)-1H-imidazol-1-yl)ethyl)benzonitrile | 459 | | CD$_3$OD δ 9.32 (s, 1H), 7.78 (d, J = 8.0 Hz, 2H), 7.63 (s, 1H), 7.44 (d, J = 8.0 Hz, 2H), 7.39 (d, J = 7.2 Hz, 1H), 7.33~7.32 (m, 1H), 7.00 (dd, J1 = 2.4 Hz, J2 = 4.8 Hz, 1H), 6.13 (q, J = 6.8 Hz, 1H), 3.80 (s, 3H), 3.68 (d, J = 14.8 Hz, 1H), 3.56~3.40 (m, 5H), 2.63~2.49 (m, 4H), 1.96 (d, J = 6.8 Hz, 3H). |
| 39 | | (R)-4-(1-(5-((4-(1H-benzo[d]imidazol-2-yl)piperazin-1-yl)methyl)-1H-imidazol-1-yl)ethyl)benzonitrile | 412 | | CD$_3$OD δ 9.32 (s, 1H), 7.79 (d, J = 8.0 Hz, 2H), 7.63 (s, 1H), 7.46 (d, J = 8.0 Hz, 2H), 7.37 (dd, J1 = 3.2 Hz, J2 = 6.0 Hz, 2H), 7.29 (dd, J1 = 3.2 Hz, J2 = 6.0 Hz, 2H), 6.12 (q, J = 7.2 Hz, 1H), 3.67 (d, J = 14.4 Hz, 1H), 3.56~3.40 (m, 5H), 2.64~2.50 (m, 4H), 1.97 (d, J = 7.2 Hz, 3H). |

Example 40

(R)-5-(ethylsulfonyl)-2-(4-((1-(1-(4-fluorophenyl)propan-2-yl)-1H-imidazol-5-yl)methyl)piperazin-1-yl)thiazole (Compound 40)

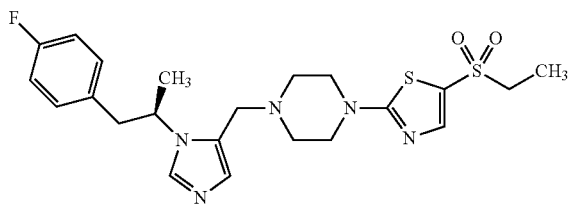 [SMILES: CCS(=O)(=O)c1cnc(N2CCN(Cc3cncn3[C@H](C)Cc3ccc(F)cc3)CC2)s1]

Step A—Preparation of Int 40-1

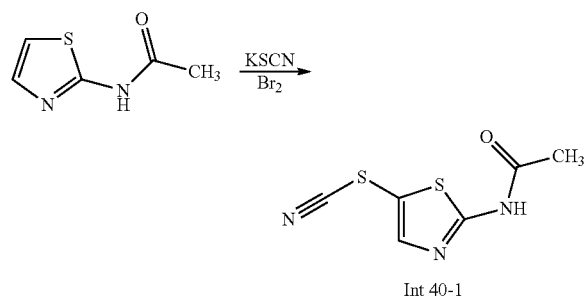

To a stirred solution of compound N-acetyl-2-aminothiazole (10.0 g, 0.07 mol) and KSCN (12.3 g, 0.13 mol) in 100 mL of ethanol was added Br$_2$ (18 mL, 0.35 mol) at 0° C. The mixture was stirred at room temperature for 16 h. The resulting mixture was diluted with ethanol and filtered to afford 5 grams of the crude compound Int 40-1 as yellow solid. MS (ESI) m/z (M+1): 200.

Step B—Preparation of Int 40-2

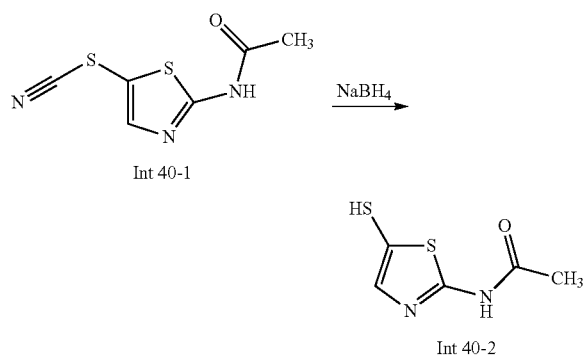

To a stirred solution of compound Int 40-1 (3.5 g, 0.017 mol) in 40 mL of methanol was added NaBH$_4$ (0.97 g, 0.025 mol) at 0° C. and the mixture was stirred at room temperature for 16 h. The result mixture was concentrated to afford 3.0 g of the crude compound Int 40-2 as yellow solid. MS (ESI) m/z (M+1): 175.

Step C—Preparation of Int 40-3

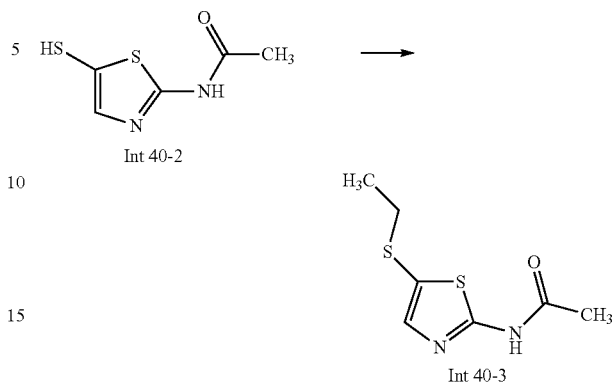

Compound Int 40-2 (3.0 g, 0.017 mol), iodoethane (2.9 g, 0.018 mol), KF (1.28 g, 0.022 mol), CuI (716 mg, 5.1 mmol), Al$_2$O$_3$ (520 mg, 5.1 mmol) and 15 mL of DMF were combined in a 30 mL three-necked round bottom flask. The mixture was degassed with nitrogen and stirred at 110° C. for 16 h. The reaction mixture was cooled to room temperature and filtered. The filtrate was concentrated to give crude product which was purified by column chromatography on silica gel with petroleum ether/ethyl acetate (1:1) to afford 2.0 g of compound Int 40-3 as a brown solid. MS (ESI) m/z (M+1): 203.

Step D—Preparation of Int 40-4

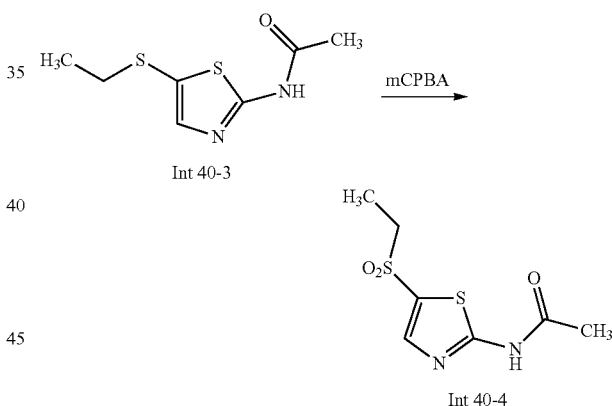

To a solution of compound Int 40-3 (1.5 g, 7.4 mmol) in dichloromethane (20 mL) was added mCPBA (3.84 g, 22.3 mmol). The mixture was stirred at room temperature overnight. The mixture was quenched by saturated aqueous Na$_2$S$_2$O$_3$ and washed with DCM×3. The combined organic extracts were dried over MgSO$_4$, filtered and concentrated to give crude product which was purified by preparative TLC to afford 1.4 g of compound Int 40-4 as a white solid. MS (ESI) m/z (M+1): 235.

Step E—Preparation of Int 40-5

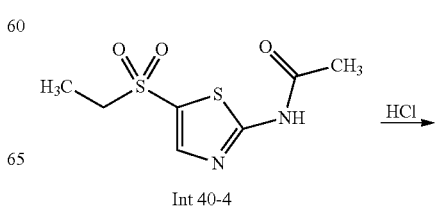

-continued

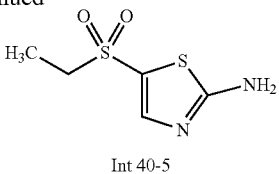

Int 40-5

To a stirred solution of compound Int 40-4 (1.4 g, 5.98 mmol) in 6 mL of ethanol was added 6M HCl (2 mL). The mixture was heated to 80° C. for 12 h. The reaction was concentrated and the residue was basified with saturated NaHCO₃ and washed with EtOAc. The organic extracts were dried and concentrated to afford the crude aminothiazole which was used in the next step without further purification. MS (ESI) m/z (M+1): 193.

Step F—Preparation of Int 40-6

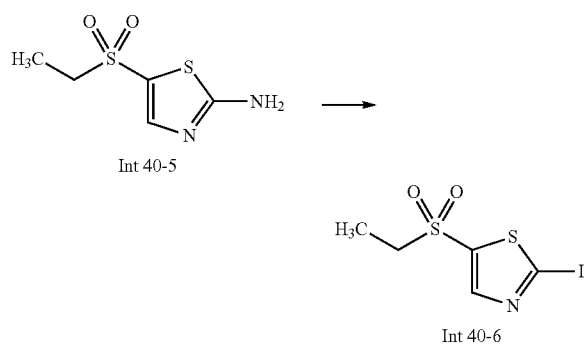

Compound Int 40-5 (560 mg, 2.90 mmol) was dissolved in CH₂I₂ (5 mL). The mixture was heated to 70° C. for 2 h then concentrated. The residue was purified by column chromatography on silica gel with petroleum ether/ethyl acetate=1:1 to afford 850 mg of compound Int 40-6 as a yellow solid. MS(ESI) m/z (M+1)=304. ¹H NMR (CD₃OD) δ 8.04 (s, 1H), 3.3~3.35 (m, 2H), 1.28 (t, J=7.2 Hz, 3H).

Step G—Preparation of Compound 40

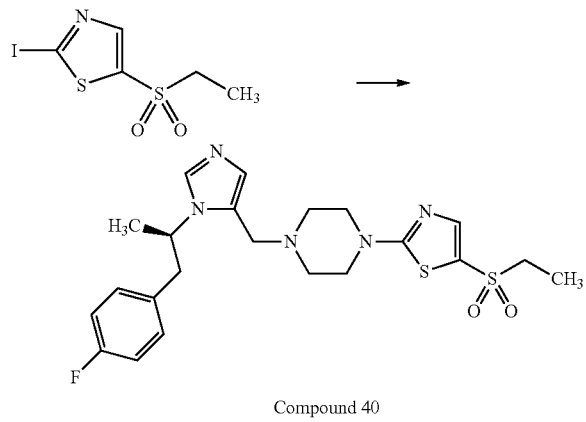

Compound 40

To a stirred solution of compound Int 40-6 (200 mg, 0.66 mmol) in CH₃CN (8 mL) was added K₂CO₃ (1.98 mmol) and 900 mg (9.2 mmol) of the piperazine analog (prepared as described in Example 1 starting from (R)-1-(4-fluorophenyl)propan-2-amine). The mixture was stirred at 105° C. for 2 h. The reaction mixture was cooled and added to water (5 mL) and EtOAc (10 mL). The aqueous layer was extracted with EtOAc (3×5 mL). The combined organic washings were dried over MgSO₄ and concentrated to give crude product which was purified by HPLC to afford 32 mg of Compound 40. ¹H NMR (CD₃OD) δ 9.21 (s, 1H), 7.67 (s, 1H), 7.48 (s, 1H), 7.17~7.14 (m, 2H), 7.05~7.01 (m, 2H), 5.06 (q, J=6.8 Hz, 1H), 3.61~3.57 (m, 5H), 3.43 (d, J=14.4 Hz, 1H), 3.25~3.14 (m, 4H), 2.65~2.63 (m, 4H), 1.65 (d, J=6.8 Hz, 3H), 1.29 (t, J=7.2 Hz, 3H). MS(ESI) m/z (M+1): 478.

Example 41

(R)-5-(2-(ethylsulfonyl)ethyl)-2-(4-((1-(1-(4-fluorophenyl)propan-2-yl)-1H-imidazol-5-yl)methyl)piperazin-1-yl)thiazole (Compound 41)

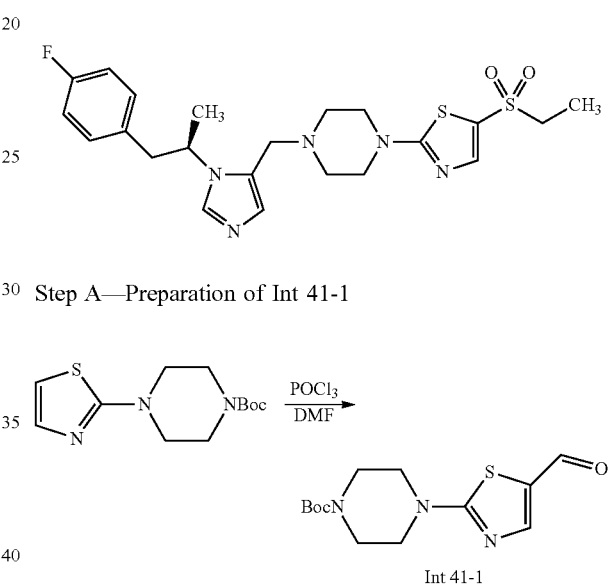

Step A—Preparation of Int 41-1

To a solution of tert-butyl 4-(thiazol-2-yl)piperazine-1-carboxylate (2 g, 0.74 mmol) in DMF (20 mL) was added POCl₃ (17.08 g, 11.2 mmol). The mixture was stirred at 50° C. for 3 h. The resulting mixture was poured into cold water and filtered. The filter cake was washed with water and collected to afforded 2 g of white solid. MS-ESI (m/z): 242 (M-55)⁺. ¹H NMR (CDCl₃) δ: 9.68 (s, 1H), 7.84 (s, 1H), 3.61 (br, 4H), 3.56 (br, 4H).

Step B—Preparation of Int 41-2

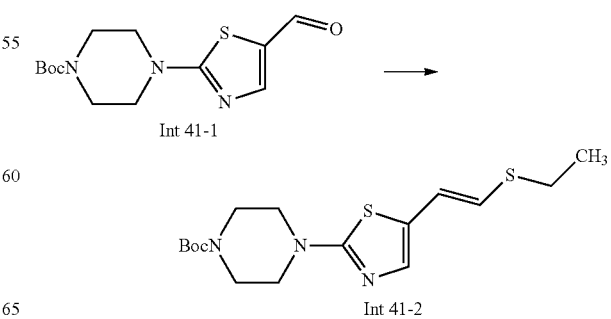

To a solution of compound diethyl ((ethylthio)methyl) phosphonate (71.4 mg, 0.34 mmol) in THF (2 mL) was added NaH (9.7 mg, 0.4 mmol). The mixture was stirred at room temperature for 1 h then compound 1 was added. The resulting mixture was stirred for 16 h then quenched with water and extracted with DCM (3×). The combined organic washings were dried over MgSO$_4$ and concentrated. The crude residue was purified by preparative TLC to give 58 mg of white solid. MS-ESI (m/z): 300 (M-55)$^+$. $^1$H NMR (CDCl$_3$) δ: 6.88 (s, 2H), 6.43 (d, J=15.2 Hz, 1H), 6.07 (d, J=15.2 Hz, 1H), 3.47 (br, 4H), 3.39 (br, 4H), 2.69 (q, J=7.6, 2H), 1.41 (s, 9H), 1.26 (t, J=7.6, 3H).

Step C—Preparation of Int 41-3

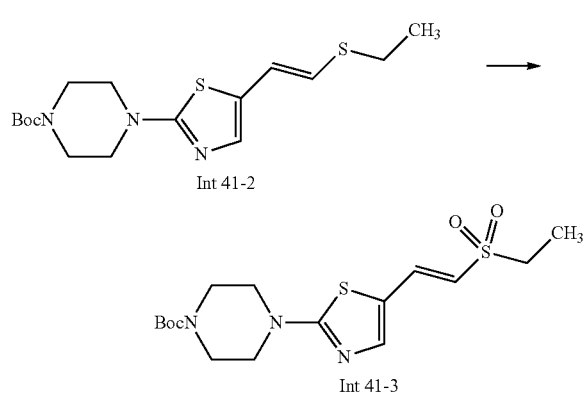

Int 41-2

Int 41-3

To a solution of compound Int 41-2 (0.5 g, 1.4 mmol) in CH$_2$Cl$_2$ (10 mL) was added mCPBA (0.49 g, 2.8 mmol). The mixture was stirred at room temperature for 40 min. The reaction mixture was quenched with saturated Na$_2$SO$_3$ and extracted with CH$_2$Cl$_2$ (3×10 mL). The combined organic extracts were dried over MgSO$_4$ and concentrated to afforded 0.4 g of yellow solid. MS-ESI (m/z): 332 (M-55)$^+$.

Step D—Preparation of Int 41-4

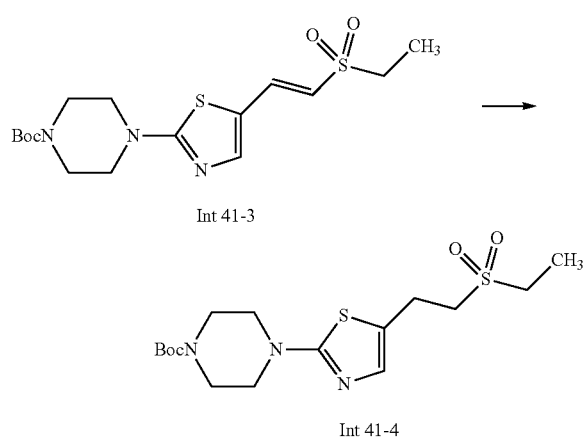

Int 41-3

Int 41-4

To a solution of Int 41-3 (0.4 g, 1.03 mmol) in methanol (1 mL) was added Pd/C (0.05 g). The mixture was charged with H$_2$ (50 psi) and the mixture was stirred at 40° C. for 16 h. The mixture was then filtered through Celite and the filtrate was concentrated to dryness. The crude material was used in next step directly. MS-ESI (m/z): 334 (M-55)$^+$.

Step E—Preparation of Int 41-5

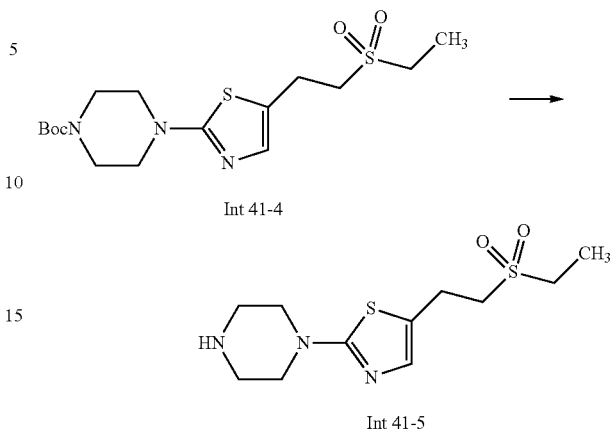

Int 41-4

Int 41-5

Compound Int 41-4 (1 g, 2.57 mmol) was dissolved in HCl/EtOAc (10 mL) and the mixture was stirred at room temperature for 30 min. The mixture was concentrated to dryness and used in next step directly. MS-ESI (m/z): 290 (M+1)$^+$.

Step F—Preparation of Compound 41

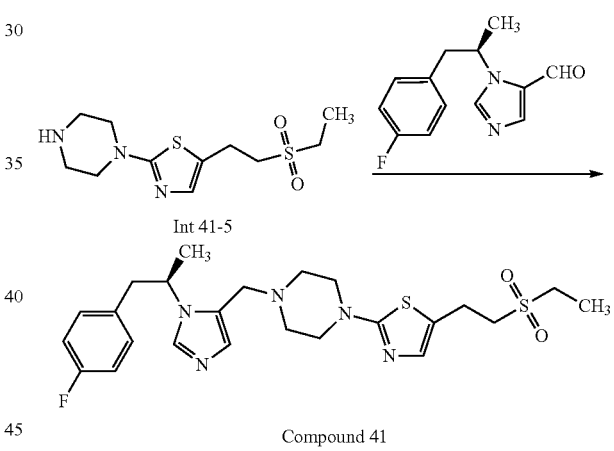

Int 41-5

Compound 41

To a solution of compound Int 41-5 (100 mg, 0.44 mmol) in CH$_2$Cl$_2$ (2 mL) was added Et3N (0.1 mL) followed by 128 mg (0.44 mmol) of the aldehyde analog (prepared as described in Example 1 starting from (R)-1-(4-fluorophenyl) propan-2-amine). The mixture was stirred for 1 h then NaBH(OAc)$_3$ (282 mg, 1.33 mmol) was added. The resulting mixture was stirred at room temperature for 16 h. The reaction mixture was quenched with water and extracted with CH$_2$Cl$_2$ (3×). The combined organic layer was dried over MgSO$_4$ and concentrated. The crude was purified by HPLC to give 30 mg of white solid. MS-ESI (m/z): 506 (M+1)$^+$. $^1$H NMR (CD$_3$OD) δ 9.17 (s, 1H), 7.45 (s, 1H), 7.18-7.11 (m, 3H), 7.00 (t, J=8.8 Hz, 2H), 5.10-4.98 (m, 1H), 3.70-3.50 (m, 5H), 3.43-3.33 (m, 3H), 3.28-3.09 (m, 5H), 2.52-2.50 (br, 4H), 1.62 (d, J=6.8 Hz, 3H), 1.40-1.28 (m, 4H).

The following compounds 42-43 were prepared using a protocol similar to that described in Example 41 and an appropriately substituted imidazole carboxaldehyde (prepared as illustrated in Example 1).

| Cmpd | Structure | IUPAC name | M+1 | $^1$H NMR |
|---|---|---|---|---|
| 42 | 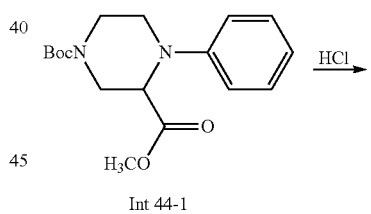 | (R)-2-(4-((1-(1-(4-chlorophenyl)ethyl)-1H-imidazol-5-yl)methyl)piperazin-1-yl)-5-(2-(ethylsulfonyl)ethyl)thiazole | 508 | CD$_3$OD δ 9.25 (s, 1H), 7.60 (s, 1H), 7.42 (d, J = 8.4 Hz, 2H), 7.27 (d, J = 8.4 Hz, 2H), 7.18 (s, 1H), 6.03 (s, 1H), 3.65 (d, J = 14.4 Hz, 1H), 3.55-3.38 (m, 7H), 3.19 (t, J = 7.6 Hz, 2H), 3.10 (q, J = 7.2, 2H), 2.68-2.49 (m, 4H), 1.93 (d, J = 6.8 Hz, 3H), 1.33 (t, J = 7.6 Hz, 3H). |
| 43 | 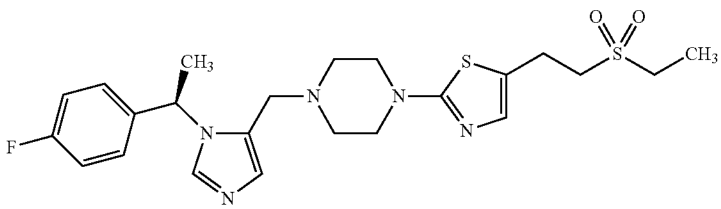 [SMILES: CCS(=O)(=O)CCc1cnc(N2CCN(Cc3cncn3[C@H](C)c3ccc(F)cc3)CC2)s1] | (R)-2-(4-((1-(1-(4-fluorophenyl)ethyl)-1H-imidazol-5-yl)methyl)piperazin-1-yl)-5-(2-(ethylsulfonyl)ethyl)thiazole | 492 | CD$_3$OD δ 9.23 (s, 1H), 7.60 (s, 1H), 7.38-7.30 (m, 2H), 7.19 (s, 1H), 7.13 (t, J = 6.8 Hz, 2H), 6.03 (q, J = 6.8 Hz, 1H), 4.26-4.00 (m, 1H), 3.68 (d, J = 14.4 Hz, 1H), 3.55-3.38 (m, 7H), 3.19 (t, J = 7.6 Hz, 2H), 3.10 (q, J = 7.2, 2H), 2.68-2.49 (m, 4H), 1.93 (d, J = 6.8 Hz, 3H), 1.33 (t, J = 7.6 Hz, 3H). |

Example 44

N-(tert-butyl)-4-((1-((R)-1-(4-cyanophenyl)ethyl)-1H-imidazol-5-yl)methyl)-1-phenylpiperazine-2-carboxamide (Compound 44)

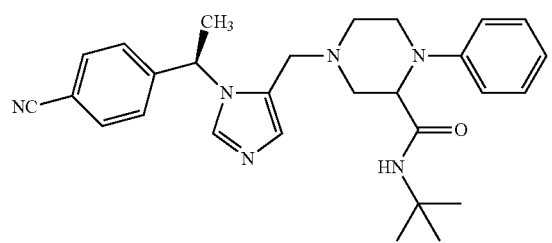 [SMILES: C[C@H](c1ccc(C#N)cc1)n1cncc1CN1CCN(c2ccccc2)C(C(=O)NC(C)(C)C)C1]

Step A—Preparation of Int 44-1

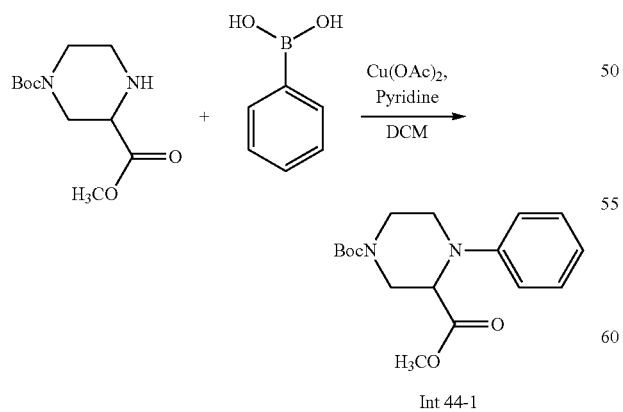

To a solution of 1-tert-butyl 3-methyl piperazine-1,3-dicarboxylate (2.44 g, 10 mmol) in DCM (50 mL) was added phenylboronic acid (2.35 g, 20 mmol), Cu(OAc)$_2$ (1.82 g, 10 mmol) and pyridine (1.58 g, 20 mmol) in turns with stirring. The reaction mixture was stirred at ambient temperature for 24 hrs under an oxygen atmosphere. The reaction mixture was filtered and filtrate was concentrated. The residue was purified by column chromatography on silica gel (petroleum ether:EtOAc=3:1) to afford compound Int 44-1 (2.74 g). MS-ESI (m/z): 321 (M+1)$^+$ R$_f$: 0.3 (PE:EtOAc=3:1).

Step B—Preparation of Int 44-2

HCl gas was bubbled into an ice cold solution of compound Int 44-1 (2.73 g, 8.5 mmol) in 20 mL of EtOAc for 10 minutes. The reaction mixture was stirred to room temperature over an hour then concentrated to afford Int 44-2 (1.38 g). MS-ESI (m/z): 221 (M+1)$^+$.

Step C—Preparation of Int 44-3

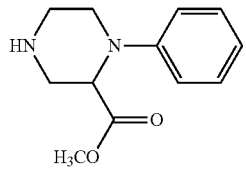

Int 44-2

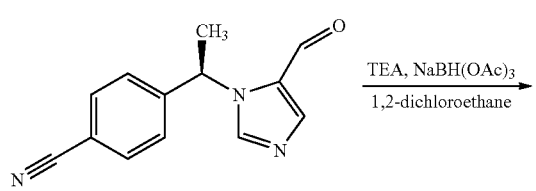

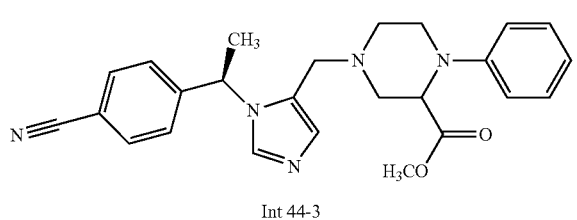

Int 44-3

To a solution of compound Int 44-2 (1.38 g, 5.1 mmol) in 1,2-dichloroethane (20 mL) was added the imidazole carboxaldehyde (1.14 g, 5.1 mmol) and TEA (0.71 mL, 10.2 mmol) with stirring under $N_2$. The reaction mixture was stirred at ambient temperature for 2 h before NaBH(OAc)$_3$ was added. The reaction mixture was stirred another 16 h before being quenched with saturated NH$_4$Cl. The mixture was extracted with EtOAc and the organic washings were dried, filtered and concentrated. The residue was purified by column chromatography on silica gel (petroleum ether:EtOAc=1:1) to afford compound Int 44-3 (1.77 g). MS-ESI (m/z): 430 (M+1)$^+$ R$_f$: 0.3 (PE:EtOAc=1:1).

Step D—Preparation of Int 44-4

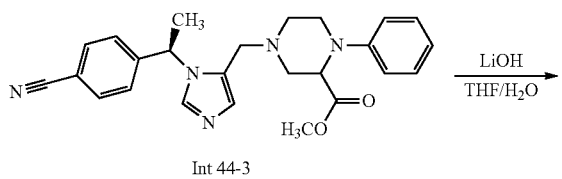

Int 44-3

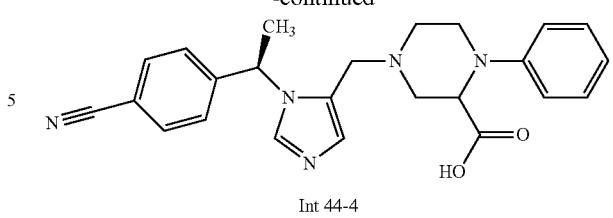

Int 44-4

To a solution of compound Int 44-3 (478.4 mg, 1.1 mmol) in THF (6 mL) and water (3 mL) was added LiOH.H$_2$O (59.4 mg, 1.45 mmol) with stirring. The reaction mixture was stirred at 25° C. for 15 h. The reaction mixture was extracted with EtOAc and then the aqueous layer was adjusted pH to 5 by conc. HCl. The result solution was extracted with EtOAc, the organic layers were combined and dried, filtered and concentrated to afford compound Int 44-4 (370 mg). MS-ESI (m/z): 416 (M+1)$^+$.

Step E—Preparation of Int 44-5

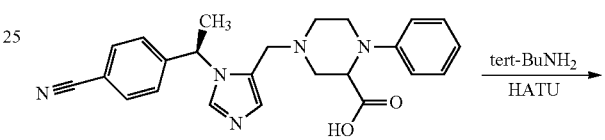

Int 44-4

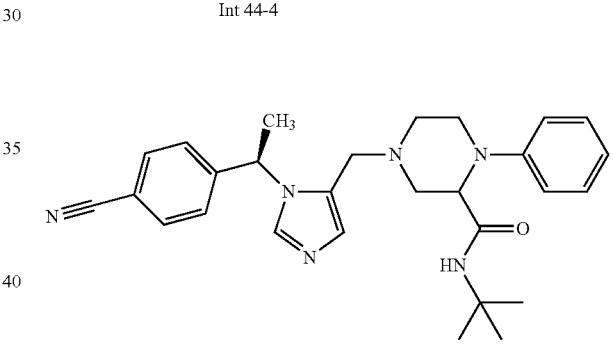

Compound 44

To a solution of compound Int 44-4 (99.1 mg, 0.24 mmol) in DCM (1 mL) was added DIPEA (93.1 mg, 0.72 mmol) and HATU (98.8 mg, 0.26 mmol) in turns with stirring. After being stirred at 25° C. for 30 min, the reaction mixture was treated with tert-butylamine (0.26 mmol), and stirring continued for another 10 h. The reaction mixture was concentrated and purified by HPLC to afford Compound 44. $^1$H NMR (CD$_3$OD) δ: 9.33 (d, J=46.8 Hz, 1H), 7.74 (q, J=8.4 Hz, 2H), 7.59 (t, J$_1$=31.2 Hz, J$_2$=23.2 Hz, 2H), 7.44 (d, J=8.4 Hz, 1H), 7.43~7.26 (m, 2H), 7.05 (d, J=8.0 Hz, 1H), 6.98~6.94 (m, 2H), 6.52 (t, J$_1$=1.2 Hz, J$_2$=6.8 Hz, 1H), 3.84 (q, J=14.4 Hz, 1H), 3.68 (t, J$_1$=26.8 Hz, J$_2$=14.4 Hz, 1H), 3.49~3.42 (m, 2H), 3.29~3.09 (m, 2H), 2.90 (t, J$_1$=11.6 Hz, J$_2$=9.6 Hz, 1H), 2.69 (d, J=12 Hz, 1H), 2.34 (t, J$_1$=50.8 Hz, J$_2$=1.6 Hz, 1H), 1.96 (q, J=7.2 Hz, 3H), 1.31 (d, J=9.6 Hz, 9H). MS-ESI (m/z): 471 (M+1)$^+$.

The following compounds 45-47 were prepared as described in Example 44 starting from carboxylic acid intermediate Int 44-4 and an amine coupling partner.

| Cmpd | Structure | IUPAC name | M + 1 | ¹H NMR |
|---|---|---|---|---|
| 45a | 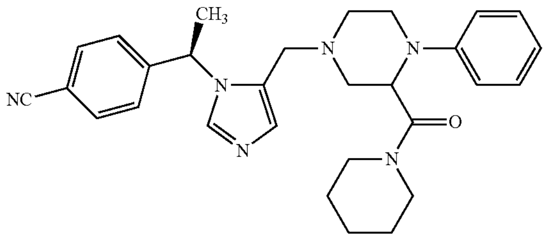 [SMILES: C[C@H](c1ccc(C#N)cc1)n1cncc1CN1CCN(c2ccccc2)C(C(=O)N2CCCCC2)C1] | 4-((1R)-1-(5-((4-phenyl-3-(piperidine-1-carbonyl)piperazin-1-yl)methyl)-1H-imidazol-1-yl)ethyl)benzonitrile: diastereomer A | 483 | CD$_3$OD δ: 9.35 (s, 1H), 7.76 (t, J1 = 12.8 Hz, J2 = 4.8 Hz, 3H), 7.44 (d, J = 8.4 Hz, 2H), 7.27 (q, J = 7.2 Hz, 2H), 7.00 (d, J = 4.0 Hz, 2H), 6.91 (t, J1 = 14.8 Hz, J2 = 7.2 Hz, 1H), 6.55 (q, J = 6.8 Hz, 1H), 4.12 (q, J = 2.8 Hz, 1H), 3.72 (q, J = 10 Hz, 4H), 3.68~3.52 (m, 4H), 3.30~3.24 (m, 1H), 3.06~2.93 (m, 2H), 2.80~2.73 (m, 1H), 1.98 (d, J = 7.2 Hz, 3H), 1.68 (t, J1 = 10 Hz, J2 = 5.2 Hz, 5H), 1.62 (s, 1H). |
| 45b | 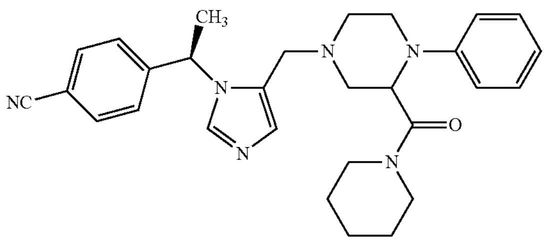 [SMILES: C[C@H](c1ccc(C#N)cc1)n1cncc1CN1CCN(c2ccccc2)C(C(=O)N2CCCCC2)C1] | 4-((1R)-1-(5-((4-phenyl-3-(piperidine-1-carbonyl)piperazin-1-yl)methyl)-1H-imidazol-1-yl)ethyl)benzonitrile: diastereomer B | 483 | CD$_3$OD δ: 9.30 (s, 1H), 7.74 (d, J = 8.0 Hz, 2H), 7.61 (s, 1H), 7.54 (d, J = 8.4 Hz, 2H), 7.24 (d, J1 = 15.2 Hz, J2 = 7.6 Hz, 2H), 6.921 (s, 3H), 6.70 (d, J = 7.2 Hz, 1H), 3.95 (d, J = 14 Hz, 1H), 3.73 (d, J = 10.4 Hz, 1H), 3.61 (s, 3H), 3.51 (d, J = 11.2 Hz, 2H), 3.36 (d, J = 14.4 Hz, 1H), 3.26 (t, J1 = 17.6 Hz, J2 = 1.2 Hz, 1H), 2.76~2.65 (m, 2H), 2.38 (t, J1 = 22.4 Hz, J2 = 10.8 Hz, 1H), 2.03 (d, J = 11.6 Hz, 1H), 1.93 (d, J = 7.2 Hz, 3H), 1.70 (d, J = 4.8 Hz, 2H), 1.62 (s, 2H), 1.55 (d, J = 3.2 Hz, 2H). |
| 46 | 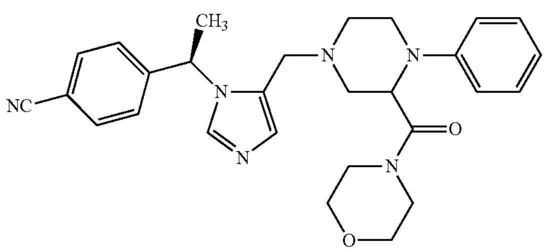 [SMILES: C[C@H](c1ccc(C#N)cc1)n1cncc1CN1CCN(c2ccccc2)C(C(=O)N2CCOCC2)C1] | 4-((1R)-1-(5-((3-(morpholine-4-carbonyl)-4-phenylpiperazin-1-yl)methyl)-1H-imidazol-1-yl)ethyl)benzonitrile | 485 | δ: 9.33 (d, J = 0.8 Hz, 1H), 7.75 (d, J = 8.4 Hz, 2H), 7.64 (s, 1H), 7.54 (d, J = 8.4 Hz, 2H), 7.30 (t, J1 = 16 Hz, J2 = 7.6 Hz, 2H), 6.99 (t, J1 = 8.8 Hz, J2 = 6.0 Hz, 3H), 6.64 (q, J = 6.8 Hz, 1H), 4.01 (d, J = 14 Hz, 1H), 3.87~3.83 (m, 1H), 3.68~3.28 (m, 11H), 2.82 (q, J = 10.4 Hz, 1H), 2.72 (d, J = 12 Hz, 1H), 2.52~2.45 (m, 1H), 2.10 (q, J = 9.2 Hz, 1H), 1.93 (d, J = 7.2 Hz, 3H). |
| 47 | 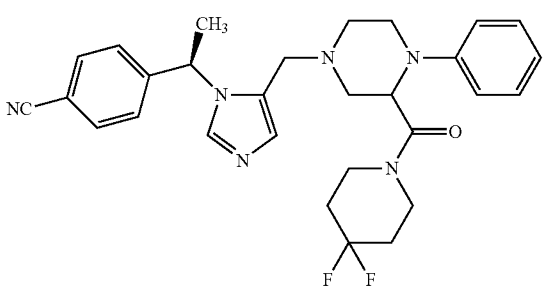 [SMILES: C[C@H](c1ccc(C#N)cc1)n1cncc1CN1CCN(c2ccccc2)C(C(=O)N2CCC(F)(F)CC2)C1] | 4-((1R)-1-(5-((3-(4,4-difluoropiperidine-1-carbonyl)-4-phenylpiperazin-1-yl)methyl)-1H-imidazol-1-yl)ethyl)benzonitrile | 519 | δ: 9.32 (s, 1H), 7.73 (d, J = 8.4 Hz, 2H), 7.61 (s, 1H), 7.55 (d, J = 8.4 Hz, 2H), 7.26 (q, J = 7.2 Hz, 2H), 6.94 (d, J = 8.0 Hz, 3H), 6.70 (q, J = 7.2 Hz, 1H), 3.98 (d, J = 14 Hz, 1H), 3.84~3.72 (m, 4H), 3.66~3.48 (m, 4H), 3.37 (d, J = 14 Hz, 1H), 3.29~3.22 (m, 1H), 2.73 (t, J1 = 22 Hz, J2 = 11.6 Hz, 1H), 2.62 (d, J = 11.6 Hz, 1H), 2.38 (t, J1 = 22.4 Hz, J2 = 11.2 Hz, 1H), 2.00 (q, J = 41.6 Hz, 3H), 1.93 (d, J = 7.2 Hz, 3H). |

Example 48

(S)-4-((1-((R)-1-(4-fluorophenyl)ethyl)-1H-imidazol-5-yl)methyl)-1-phenylpiperazin-2-yl)(piperidin-1-yl)methanone (Compound 48

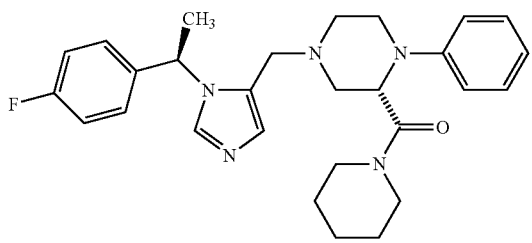 [SMILES: C[C@H](c1ccc(F)cc1)n1cncc1CN1CCN(c2ccccc2)[C@H](C(=O)N2CCCCC2)C1]

Step A—Preparation of Int 48-1

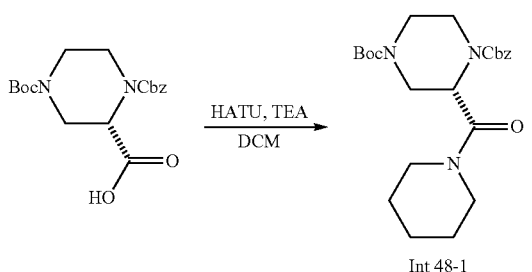

To a solution of piperazine carboxylic acid (10 g, 27 mmol) in DCM (50 mL) was added TEA (2.39 mL, 54 mmol) and HATU (11.4 g, 30 mmol) with stirring. The reaction mixture was stirred at room temperature for 30 mins then treated with piperidine (2.57 g, 30 mmol). The reaction solution was stirred for 48 hrs then concentrated. The residue was purified by column chromatography on silica gel eluted with petroleum ether/EtOAc (3:1) to afford compound Int 48-1 as yellow oil (10.7 g). MS-ESI (m/z): 432 (M+1)$^+$ R$_f$: 0.6 (PE:EtOAc=1:1)$^1$H NMR (CDCl$_3$) δ: 7.30~7.24 (m, 5H), 5.25 (s, 1H), 5.14 (d, J=12.3 Hz, 1H), 5.06~4.98 (m, 1H), 4.18~3.80 (m, 5H), 3.41 (s, 2H), 3.21 (d, J=13 Hz, 3H), 1.61 (s, 2H), 1.52 (t, J$_1$=16.6 Hz, J$_2$=14.7 Hz, 3H), 1.39 (s, 10H).

Step B—Preparation of Int 48-2

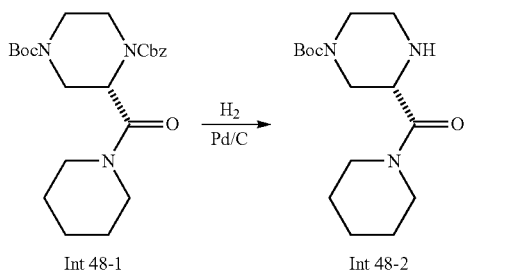

A mixture of compound Int 48-1 (10.75 g, 25 mmol) and Pd/C (1.0 g) in MeOH (25 mL) was stirred under 50 Psi of H$_2$ at room temperature for 10 hrs. The mixture was filtered through Celite and the filter cake was washed with MeOH. The combined organic layers were concentrated to afford compound Int 48-2 as yellow oil (6.97 g). MS-ESI (m/z): 298 (M+1)$^+$.

Step C—Preparation of Int 48-3

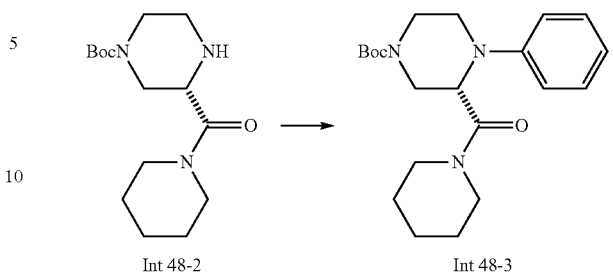

To a solution of compound Int 48-2 (6.97 g, 23 mmol) in DCM (70 mL) was added phenylboronic acid (5.72 g, 46 mmol), Cu(OAc)$_2$ (4.17 g, 23 mmol) and pyridine (3.64 g, 46 mmol) in turns with stirring. The reaction mixture was stirred at room temperature for 16 hrs under an atmosphere of oxygen. The reaction mixture was filtered and the filter cake was washed with DCM. The combined organic layers were concentrated and the residue was purified by column chromatography on silica gel (Petroleum ether:EtOAc=10:1) to afford compound Int 48-3 as yellow oil (6.08 g). MS-ESI (m/z): 374 (M+1)$^+$ R$_f$: 0.5 (PE:EtOAc=3:1) $^1$H NMR (CDCl$_3$) δ: 7.24~7.16 (m, 2H), 7.08 (t, J$_1$=14.8 Hz, J$_2$=7.5 Hz, 1H), 6.99 (d, J=8.6 Hz, 2H), 5.17 (d, J=12.2 Hz, 1H), 4.12 (q, J=7.2 Hz, 1H), 4.02~3.92 (m, 1H), 3.82 (d, J=5.2 Hz, 2H), 3.45 (s, 4H), 3.25 (d, J=8.3 Hz, 2H), 1.58 (t, J$_1$=6.2 Hz, J$_2$=1.3 Hz, 3H), 1.51 (t, J$_1$=19.2 Hz, J$_2$=12.2 Hz, 2H), 1.43 (d, J=9.8 Hz, 10H).

Step D—Preparation of Int 48-4

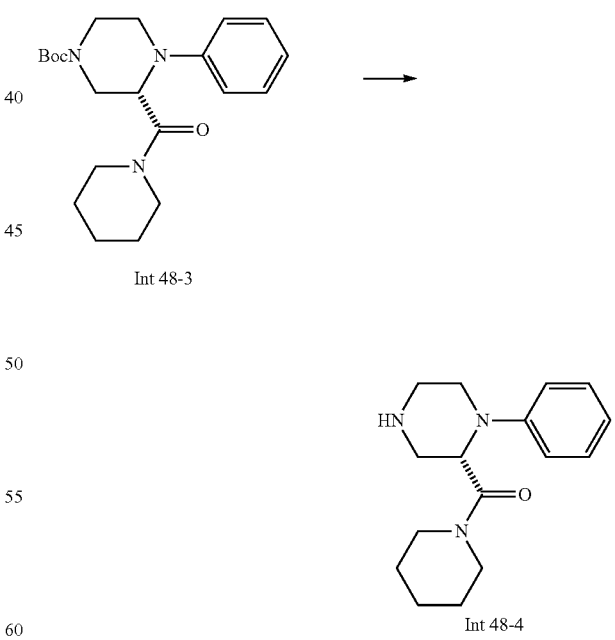

A solution of compound Int 48-3 (6.08 g, 16 mmol) in EtOAc (30 mL) saturated with HCl(g) was stirred at room temperature for 15 mins. The reaction mixture was concentrated to afford compound Int 48-4 as brown solid (5 g). MS-ESI (m/z): 274 (M+1)$^+$ R$_f$: 0.01 (PE:EtOAc=3:1).

Step E—Preparation of Compound 48

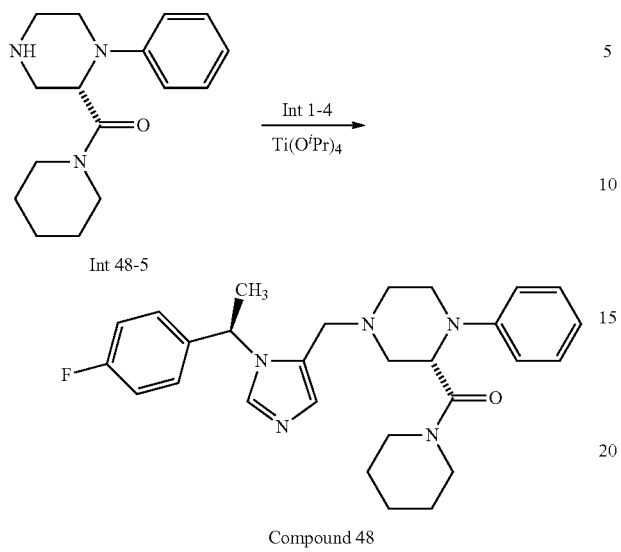

Int 48-5

Compound 48

To a solution of compound Int 48-5 (0.5 mmol) in anhydrous THF (3 mL) was added Int 1-4 (97.1 mg, 0.5 mmol), TEA (0.14 mL, 1.0 mmol) and Ti(i-PrO)$_4$ (284.2 mg, 1.0 mmol) with stirring under N$_2$. The reaction mixture was stirred at 60° C. for 2 h. The reaction mixture was cooled to room temperature before NaBH(OAc)$_3$ (317.9 mg, 1.5 mmol) was added. The reaction mixture was stirred at ambient temperature for another 20 mins under N$_2$ before being quenched with water. The mixture was filtered and the filter cake was washed with EtOAc. The combined organic layers were dried over Na$_2$SO$_4$, filtered and concentrated. The residue was purified by HPLC to afford compound 48 as a white solid. $^1$H NMR (CD$_3$OD) δ: 9.25 (d, J=8.0 Hz, 1H), 7.75 (d, J=6.8 Hz, 1H), 7.36 (t, J$_1$=22 Hz, J$_2$=13.2 Hz, 4H), 7.20 (d, J=8.0 Hz, 2H), 7.11 (s, 2H), 7.00 (s, 1H), 6.07 (s, 1H), 3.87 (q, J=13.2 Hz, 2H), 3.70 (t, J$_1$=27.6 Hz, J$_2$=13.2 Hz, 2H), 3.49 (q, J=48.4 Hz, 4H), 3.22 (t, J$_1$=48 Hz, J$_2$=12 Hz, 2H), 3.04 (t, J$_1$=35.2 Hz, J$_2$=12 Hz, 2H), 2.80 (d, J=9.6 Hz, 1H), 1.97 (s, 3H), 1.60 (s, 2H), 1.37 (s, 4H). MS-ESI (m/z): 476 (M+1)$^+$.

Example 49

(4-((1-((R)-1-(4-fluorophenyl)ethyl)-1H-imidazol-5-yl)methyl)-2-phenylpiperazin-1-yl)(5-methylisoxazol-3-yl)methanone (Compound 49)

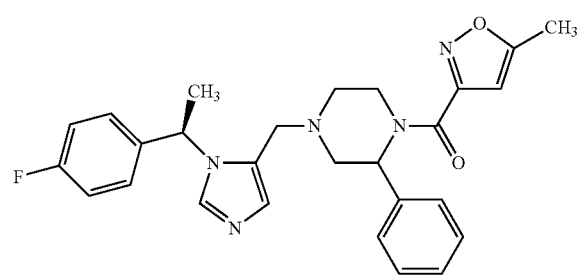 [SMILES: Cc1cc(C(=O)N2CCN(Cc3cncn3[C@H](C)c3ccc(F)cc3)CC2c2ccccc2)no1]

Step A—Preparation of Int 49-1

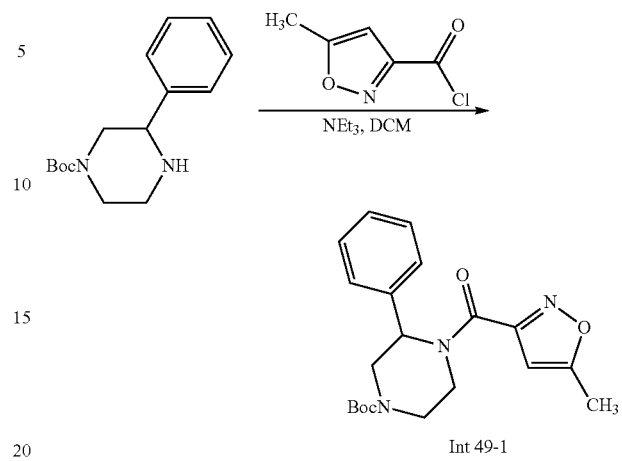

Int 49-1

To a solution of tert-butyl 3-phenylpiperazine-1-carboxylate (300 mg, 1.14 mmol) and NEt$_3$ (230 mg, 2.28 mmol) in CH$_2$Cl$_2$ (5 mL) was added 5-methylisoxazole-3-carbonyl chloride (182 mg, 1.26 mmol). The reaction mixture was stirred 0° C. for 10 min. Water was added and the mixture was extracted with 2×CH$_2$Cl$_2$. The organic layers were dried over Na$_2$SO$_4$ and concentrated. The reside was purified by prep-TLC to afford 350 mg as yellow solid. $^1$H NMR (CD$_3$OD) δ 7.29~7.21 (m, 5H), 5.74 (m, 1H), 4.59~4.56 (m, 1H), 4.10~4.02 (m, 1H), 3.89~3.83 (m, 1H), 3.38~3.29 (m, 2H), 3.03~2.91 (m, 2H), 2.40~2.32 (m, 3H), 1.32 (s, 9H). MS (ESI) m/z (M+1): 372.

Step B—Preparation of Int 49-2

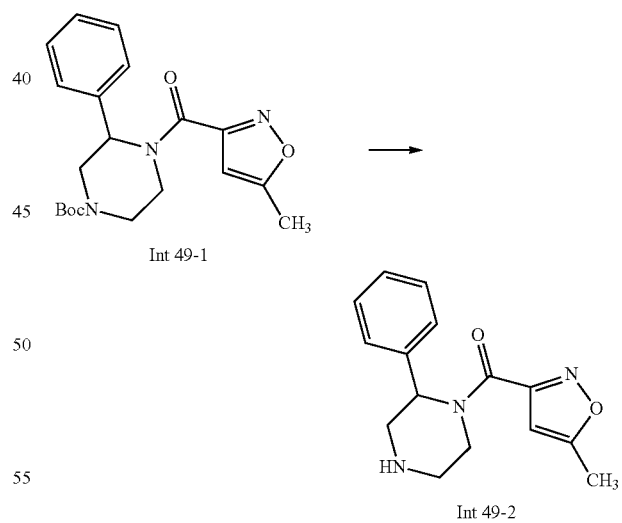

To a solution of compound Int 49-1 (350 mg, 0.94 mmol) in EtOAc (3 mL) was added HCl/EtOAc (10 mL). The mixture was stirred at ambient temperature for 30 min. The resulting white precipitate was filtered and dried to give 250 mg of the HCl salt of Int 49-2 as white solid. $^1$H NMR (CD$_3$OD) δ 9.39 (t, J=8.0 Hz, 2H), 7.31~7.27 (m, 3H), 6.38 (s, 1H), 6.04 (s, 1H), 4.63 (m, 1H), 4.14~4.10 (m, 1H), 3.56~3.51 (m, 1H), 2.39 (s, 3H), 1.91 (s, 1H), 1.89 (m, 2H). MS (ESI) m/z (M+1)=272.

Step B—Preparation of Compound 49

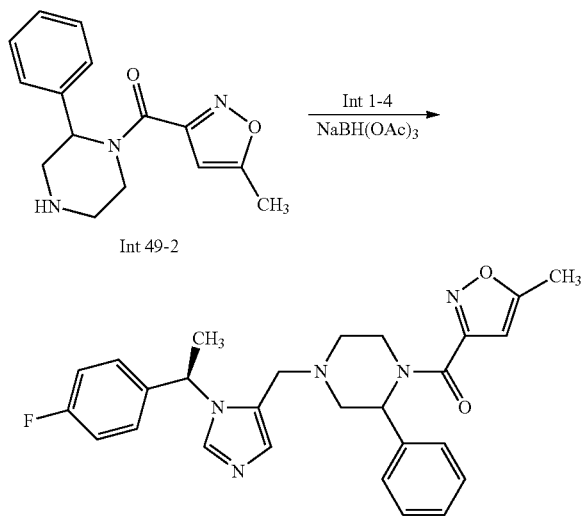

A mixture compound of Int 49-2 (250 mg, 0.94 mmol), Int 1-4 (205 mg, 0.94 mmol) in $CH_2Cl_2$ (4 mL) was stirred at room temperature for 3 h. $NaBH(OAc)_3$ (402 mg, 1.90 mmol) was added and the mixture was stirred for 16 h. Water (2 mL) was added into the reaction solution which was then extracted with $CH_2Cl_2$ (3×). The organic layers was dried over $Na_2SO_4$, concentrated and purified by prep-HPLC to afford Compound 49 as a white solid. $^1$H NMR ($CD_3OD$) δ 9.08~9.06 (s, 1H), 7.54~7.50 (s, 1H), 7.37~7.18 (m, 5H), 7.05~6.97 (m, 4H), 6.41~6.27 (m, 1H), 5.86~5.53 (m, 2H), 4.55~4.52 (m, 0.5H), 4.13~4.10 (m, 0.5H), 3.63~3.40 (m, 3H), 3.26~3.11 (m, 1H), 2.73~2.63 (m, 2H), 2.56~2.53 (m, 3H), 2.47~2.17 (m, 1H), 1.66~1.56 (m, 3H). MS (ESI) m/z (M+1)=474.

The following compounds 50-57 were prepared as described in Example 49.

| Cmpd | Structure | IUPAC name | M + 1 | $^1$H NMR |
|---|---|---|---|---|
| 50a | 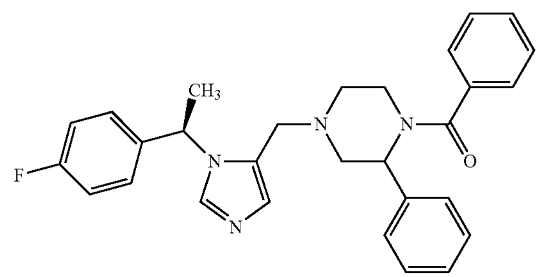 [SMILES: C[C@H](c1ccc(F)cc1)n1cncc1CN1CCN(C(=O)c2ccccc2)C(c2ccccc2)C1] | (4-((1-((R)-1-(4-fluorophenyl)ethyl)-1H-imidazol-5-yl)methyl)-2-phenylpiperazin-1-yl)(phenyl)methanone | 476 | $CD_3OD$: δ 9.14 (s, 1H), 7.52 (q, J = 7.6 Hz, 3H), 7.43~7.33 (m, 7H), 7.21 (t, J = 6.8 Hz, 3H), 7.04 (d, J = 8.0 Hz, 2H), 5.64 (s, 1H), 3.63 (d, J = 14.4 Hz, 1H), 3.52 (s, 1H), 3.24 (t, J = 21.2 Hz, 1H), 3.13 (s, 1H), 2.52 (t, J = 9.2 Hz, 2H), 2.20 (t, J = 11.2 Hz, 1H), 2.33 (s, 3H). |
| 50b | 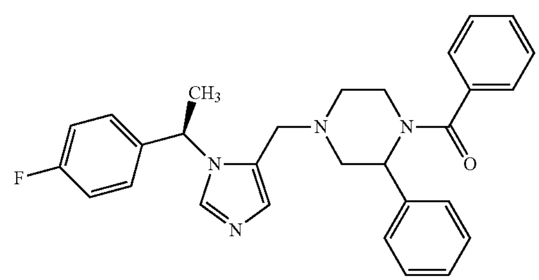 [SMILES: C[C@H](c1ccc(F)cc1)n1cncc1CN1CCN(C(=O)c2ccccc2)C(c2ccccc2)C1] | (4-((1-((R)-1-(4-fluorophenyl)ethyl)-1H-imidazol-5-yl)methyl)-2-phenylpiperazin-1-yl)(phenyl)methanone | 476 | $CD_3OD$: δ 9.14 (s, 1H), 7.63~7.53 (m, 3H), 7.36~7.21 (m, 9H), 7.06 (q, J = 7.6 Hz, 2H), 5.78 (d, J = 5.6 Hz, 1H), 3.63 (d, J = 14.8 Hz, 2H), 3.50~3.20 (m, 1H), 2.65 (dd, J1 = 12.0 Hz, J2 = 4.0 Hz, 2H), 2.15 (t, J = 10.8 Hz, 1H), 1.66~1.57 (m, 3H). |
| 51 | 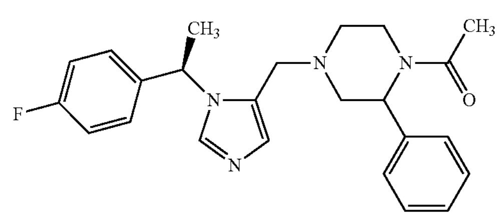 [SMILES: CC(=O)N1CCN(Cc2cncn2[C@H](C)c2ccc(F)cc2)CC1c1ccccc1] | 1-(4-((1-((R)-1-(4-fluorophenyl)ethyl)-1H-imidazol-5-yl)methyl)-2-phenylpiperazin-1-yl)ethanone | 414 | $CD_3OD$: δ: 9.13 (d, J = 13.6 Hz, 1H), 7.58 (d, J = 8.0 Hz, 3H), 7.32~7.06 (m, 7H), 5.70~5.45 (m, 2H), 4.44~4.38 (m, 1H), 3.80 (d, J = 12.4 Hz, 1H), 3.60 (d, J = 14.4 Hz, 1H), 3.48 (d, J = 9.6 Hz, 1H), 3.29~3.20 (m, 1H), 2.88 (s, 1H), 2.57 (t, J = 11.6 Hz, 1H), 2.39 (d, J = 10.4 Hz, 1H), 2.22~1.95 (m, 4H), 1.63 (d, J = 28.0 Hz, 3H). |

| Cmpd | Structure | IUPAC name | M + 1 | ¹H NMR |
|---|---|---|---|---|
| 52a | 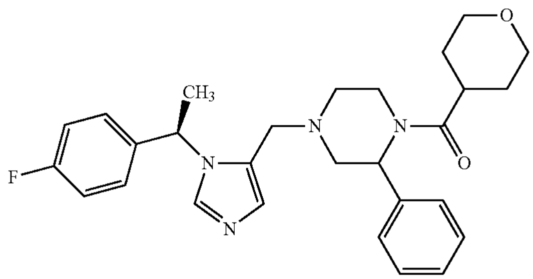 [SMILES: C[C@H](c1ccc(F)cc1)n1cncc1CN1CCN(C(=O)C2CCOCC2)C(c2ccccc2)C1] | (4-((1-((R)-1-(4-fluorophenyl)ethyl)-1H-imidazol-5-yl)methyl)-2-phenylpiperazin-1-yl)(tetrahydro-2H-pyran-4-yl)methanone | 477 | CD$_3$OD: δ 9.09~9.03 (m, 1H), 7.54 (s, 1H), 7.31 (s, 2H), 7.19 (s, 1H), 7.13 (m, 2H), 7.00~6.98 (m, 4H), 5.74~5.63 (m, 1H), 5.57~5.36 (m, 1H), 4.47~4.44 (m, 0.5H), 3.96~3.85 (m, 2.5H), 3.58~3.50 (m, 4H), 3.23 (m, 1H), 3.11~2.97 (m, 1H), 2.83~2.78 (m, 0.5H), 2.68~2.65 (m, 1H), 2.52~2.50 (m, 1H), 2.40~2.38 (m, 1H), 2.21~2.15 (m, 1H), 1.87~1.58 (m, 7H), 1.38~1.35 (m, 0.5H). |
| 52b | 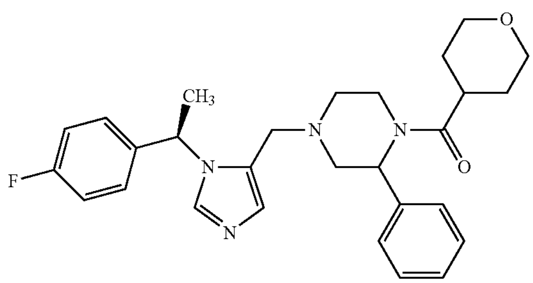 [SMILES: C[C@H](c1ccc(F)cc1)n1cncc1CN1CCN(C(=O)C2CCOCC2)C(c2ccccc2)C1] | (4-((1-((R)-1-(4-fluorophenyl)ethyl)-1H-imidazol-5-yl)methyl)-2-phenylpiperazin-1-yl)(tetrahydro-2H-pyran-4-yl)methanone | 477 | CD$_3$OD: δ 9.06 (s, 1H), 7.49 (s, 1H), 7.36~7.29 (m, 5H), 7.04~6.90 (m, 4H), 5.75 (m, 1.5H), 5.42 (m, 0.5H), 4.43 (m, 0.5H), 3.95~3.82 (m, 2.5H), 3.55~3.46 (m, 5H), 3.06 (m, 1H), 2.84~2.59 (m, 2.5H), 2.12~2.11 (m, 1H), 1.83~1.56 (m, 7H), 1.28~1.27 (m, 0.5H). |
| 53 | 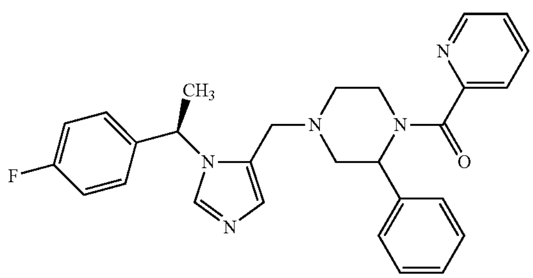 [SMILES: C[C@H](c1ccc(F)cc1)n1cncc1CN1CCN(C(=O)c2ccccn2)C(c2ccccc2)C1] | (4-(1-((R)-1-(4-fluorophenyl)ethyl)-1H-imidazol-5-yl)methyl)-2-phenylpiperazin-1-yl)(pyridin-2-yl)methanone | 470 | CD$_3$OD: δ 9.07~9.04 (m, 1H), 8.60 (m, 1H), 7.96~7.87 (m, 1H), 7.66~7.21 (m, 8H), 7.06~6.97 (m, 4H), 5.90~5.62 (m, 2H), 3.63~3.26 (m, 4H), 2.79~2.59 (m, 2H), 2.30~2.22 (m, 1H), 1.65~1.55 (m, 3H). |
| 54 | 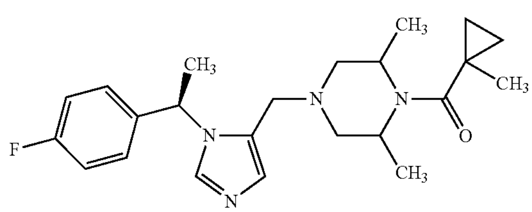 [SMILES: CC1CN(Cc2cncn2[C@H](C)c2ccc(F)cc2)CC(C)N1C(=O)C1(C)CC1] | (4-((1-((R)-1-(4-fluorophenyl)ethyl)-1H-imidazol-5-yl)methyl)-2,6-dimethylpiperazin-1-yl)(1-methylcyclopropyl)methanone | 399 | CD$_3$OD: δ 9.26 (s, 1H), 7.57 (s, 1H), 7.32~7.28 (m, 2H), 7.18 (t, J = 8.4 Hz, 2H), 6.17 (q, J = 7.2 Hz, 1H), 4.56 (m, 2H), 3.42 (s, 2H), 2.76 (d, J = 10.8 Hz, 1H), 2.65 (d, J = 11.6 Hz, 1H), 2.23~2.21 (m, 2H), 1.97 (d, J = 7.2 Hz, 3H), 1.39~1.28 (m, 9H), 0.90 (s, 2H), 0.60 (s, 2H). |
| 55 | 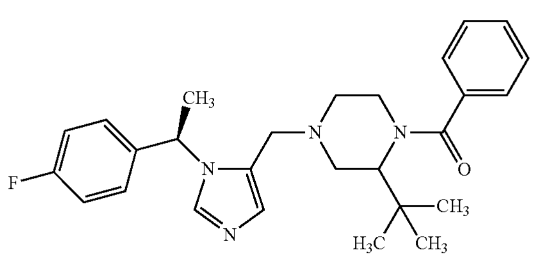 [SMILES: C[C@H](c1ccc(F)cc1)n1cncc1CN1CCN(C(=O)c2ccccc2)C(C(C)(C)C)C1] | (2-(tert-butyl)-4-((1-((R)-1-(4-fluorophenyl)ethyl)-1H-imidazol-5-yl)methyl)piperazin-1-yl)(phenyl)methanone | 449 | CD$_3$OD: δ 9.22~9.19 (m, 1H), 7.59~7.53 (m, 1H), 7.45 (m, 3H), 7.38~7.30 (m, 3H), 7.26~7.23 (m, 1H), 7.18~7.11 (m, 2H), 6.06~5.97 (m, 1H), 4.58~4.53 (m, 1H), 3.63~3.51 (m, 2.5H), 3.42~3.38 (m, 0.5H), 3.32 (s, 1H), 3.24 (m, 0.5H), 3.12~3.09 (m, 0.5H), 2.76~2.73 (m, 0.5H), 2.60~2.57 (m, 0.5H), 2.30~2.22 (m, 0.5H), 2.18~2.13 (m, |

| Cmpd | Structure | IUPAC name | M + 1 | ¹H NMR |
|---|---|---|---|---|
| | | | | 0.5H), 1.93~1.81 (m, 3.5H), 1.13 (m, 3.5H), 1.02~0.79 (m, 6H). |
| 56 | 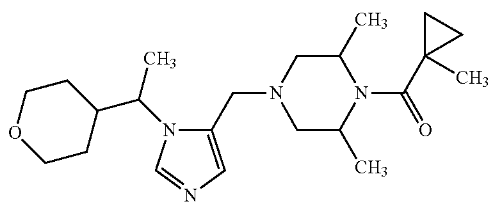 [SMILES: CC1CN(Cc2cncn2C(C)C2CCOCC2)CC(C)N1C(=O)C1(C)CC1] | (2,6-dimethyl-4-((1-(1-(tetrahydro-2H-pyran-4-yl)ethyl)-1H-imidazol-5-yl)methyl)piperazin-1-yl)(1-methylcyclopropyl)methanone | 389 | CD$_3$OD: δ 9.17 (s, 1H), 7.55 (s, 1H), 4.63~4.55 (m, 3H), 3.99 (dd, J1 = 3.6 Hz, J2 = 11.6 Hz, 1H), 3.88 (dd, J1 = 3.2 Hz, J2 = 11.6 Hz, 1H), 3.78 (d, J = 14.8 Hz, 1H), 3.62 (d, J = 14.4 Hz, 1H), 3.42~3.28 (m, 2H), 2.94 (d, J = 11.2 Hz, 1H), 2.78 (d, J = 11.2 Hz, 1H), 2.36~2.34 (m, 1H), 2.24~2.22 (m, 1H), 2.14~2.06 (m, 1H), 1.76~1.73 (m, 1H), 1.60 (d, J = 7.2 Hz, 3H), 1.44~1.18 (m, 12H), 0.90 (s, 2H), 0.60 (s, 2H). |
| 57 | 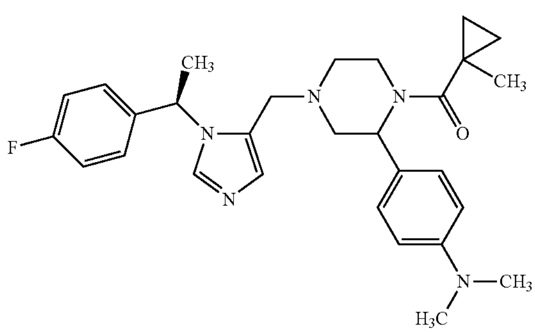 [SMILES: C[C@H](c1ccc(F)cc1)n1cncc1CN1CCN(C(=O)C2(C)CC2)C(c2ccc(N(C)C)cc2)C1] | (2-(4-(dimethylamino)phenyl)-4-((1-((R)-1-(4-fluorophenyl)ethyl)-1H-imidazol-5-yl)methyl)piperazin-1-yl)(1-methylcyclopropyl)methanone | 490 | CD$_3$OD: δ 9.15 (s, 1H), 7.64~7.50 (m, 5H), 7.22~7.12 (m, 4H), 5.76 (m, 2H), 4.38 (d, J = 13.2 Hz, 1H), 3.70~3.62 (m, 2H), 3.53 (d, J = 14.4 Hz, 1H), 3.25~3.16 (m, 7H), 3.81 (d, J = 10.8 Hz, 1H), 2.67 (d, J = 10.8 Hz, 1H), 2.21~2.16 (m, 1H), 1.79~1.69 (m, 3H), 1.35 (s, 3H), 0.99~0.95 (m, 2H), 0.69 (m, 2H). |
| 58 | 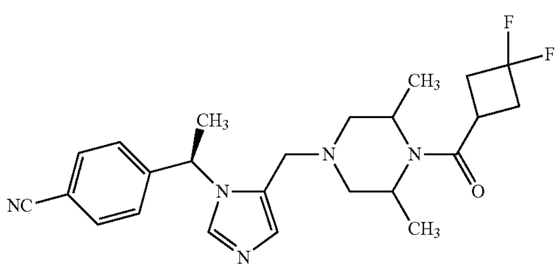 [SMILES: CC1CN(Cc2cncn2[C@H](C)c2ccc(C#N)cc2)CC(C)N1C(=O)C1CC(F)(F)C1] | 4-((1R)-1-(5-((4-(3,3-difluorocyclobutanecarbonyl)-3,5-dimethylpiperazin-1-yl)methyl)-1H-imidazol-1-yl)ethyl)benzonitrile | 442 | CD$_3$OD: δ 9.32 (s, 1H), 7.78 (d, J = 8.4 Hz, 2H), 7.61 (s, 1H), 7.41 (d, J = 8.0 Hz, 2H), 6.23 (q, J = 7.2 Hz, 1H), 4.49~4.48 (m, 1H), 4.00~3.96 (m, 1H), 3.39 (dd, J1 = 14.8 Hz, J2 = 32.8 Hz, 1H), 3.23~3.20 (m, 1H), 2.88~2.84 (m, 6H), 2.18 (m, 1H), 2.06 (m, 1H), 1.99 (d, J = 7.2 Hz, 3H), 1.30~1.23 (m, 6H). |
| 59 | 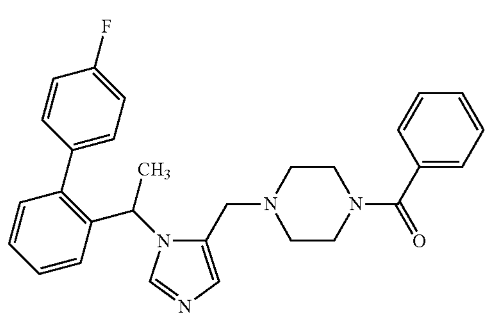 [SMILES: CC(c1ccccc1-c1ccc(F)cc1)n1cncc1CN1CCN(C(=O)c2ccccc2)CC1] | (4-((1-(1-(4'-fluoro-[1,1'-biphenyl]-2-yl)ethyl)-1H-imidazol-5-yl)methyl)piperazin-1-yl)(phenyl)methanone | 469 | CD$_3$OD: δ 8.92 (s, 1H), 7.35-7.48 (m, 9H), 7.18-7.27 (m, 5H), 5.99 (q, J = 6.8 Hz, 1H), 3.61 (s, 2H), 3.12 (d, J = 14.4 Hz, 1H), 2.95 (d, J = 14.4 Hz, 1H), 2.11-2.35 (m, 4H), 1.96 (d, J = 6.8 Hz, 3H). |

| Cmpd | Structure | IUPAC name | M + 1 | ¹H NMR |
|---|---|---|---|---|
| 60 | 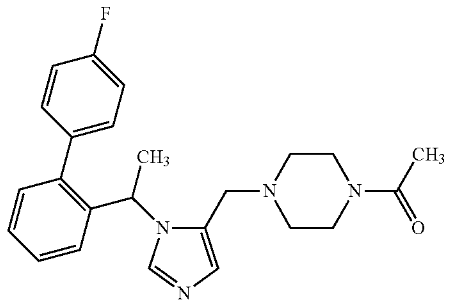 [SMILES: CC(=O)N1CCN(Cc2cncn2C(C)c2ccccc2-c2ccc(F)cc2)CC1] | 1-(4-((1-(1-(4'-fluoro-[1,1'-biphenyl]-2-yl)ethyl)-1H-imidazol-5-yl)methyl)piperazin-1-yl)ethanone | 407 | CD$_3$OD: δ 8.92 (s, 1H), 7.41-7.49 (m, 4H), 7.19-7.27 (m, 5H), 5.98-6.01 (m, 1H), 3.38-4.41 (m, 4H), 3.10 (d, J = 14.4 Hz, 1H), 2.93 (d, J = 14.4 Hz, 1H), 2.09-2.26 (m, 4H), 1.95 (d, J = 6.8 Hz, 3H). |

Example 61

(R)-1-benzyl-4-((1-(1-(4-fluorophenyl)ethyl)-1H-imidazol-5-yl)methyl)piperazin-2-one (Compound 61)

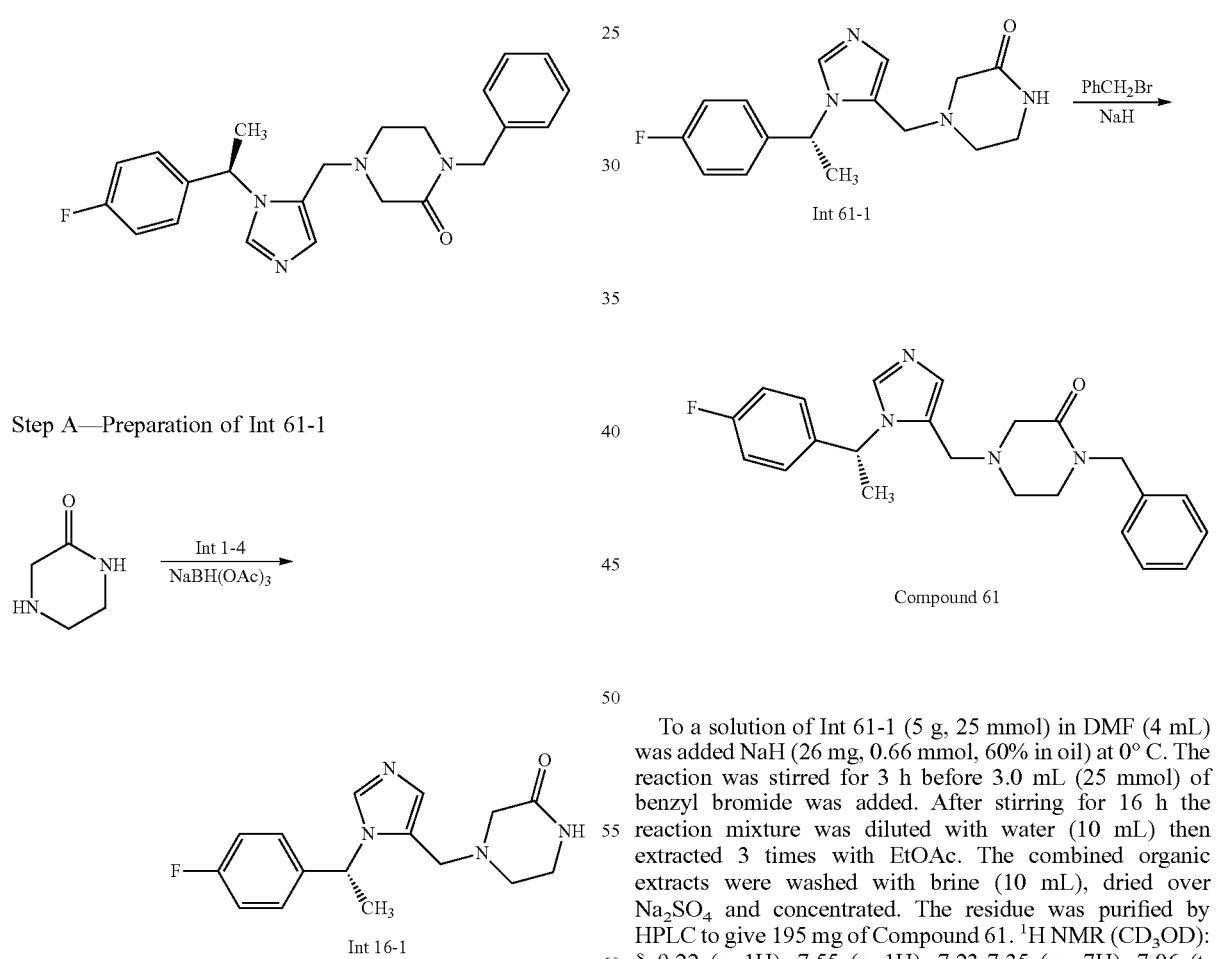

Step A—Preparation of Int 61-1

To a solution of piperazinone (0.917 g, 9.17 mmol) and Int 1-4 (2 g, 9.17 mmol) in DCM (20 mL) was added NaBH(OAc)$_3$ (1.94 mg, 9.17 mmol). The mixture was stirred at room temperature overnight, then water (10 mL) was added to quench the reaction. The reaction mixture was extracted with CH$_2$Cl$_2$ (3×20 mL) and the combined organic extracts were washed with brine (15 mL), dried over Na$_2$SO$_4$ and concentrated to give 2 g of the product Int 16-1 which was used directly for the next step. MS (ESI): m/z (M+H)$^+$ 303.

Step B—Preparation of Compound 61

To a solution of Int 61-1 (5 g, 25 mmol) in DMF (4 mL) was added NaH (26 mg, 0.66 mmol, 60% in oil) at 0° C. The reaction was stirred for 3 h before 3.0 mL (25 mmol) of benzyl bromide was added. After stirring for 16 h the reaction mixture was diluted with water (10 mL) then extracted 3 times with EtOAc. The combined organic extracts were washed with brine (10 mL), dried over Na$_2$SO$_4$ and concentrated. The residue was purified by HPLC to give 195 mg of Compound 61. ¹H NMR (CD$_3$OD): δ 9.22 (s, 1H), 7.55 (s, 1H), 7.23-7.35 (m, 7H), 7.06 (t, J=17.2 Hz, 2H), 5.93-5.98 (m, 1H), 4.49-4.59 (m, 2H), 3.68 (d, J=14.4 Hz, 1H), 3.48 (d, J=14.4 Hz, 1H), 3.03-3.21 (m, 4H), 2.56-2.69 (m, 2H), 1.90 (d, J=7.2 Hz, 3H). MS (ESI): m/z (M+H)$^+$ 393.2.

The following compounds 62-64 were prepared as described in Example 61 from Int 61-1 and an appropriately substituted halide.

| Cmpd | Structure | IUPAC name | M + 1 | 1H NMR |
|---|---|---|---|---|
| 62 | 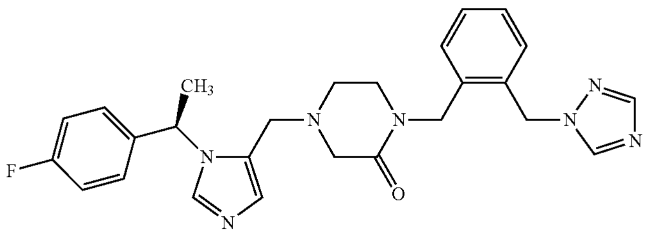 [SMILES: C[C@H](c1ccc(F)cc1)n1cncc1CN1CCN(Cc2ccccc2Cn2cncn2)C(=O)C1] | (R)-1-(2-((1H-1,2,4-triazol-1-yl)methyl)benzyl)-4-((1-(1-(4-fluorophenyl)ethyl)-1H-imidazol-5-yl)methyl)piperazin-2-one | 474 | CD$_3$OD: δ 9.23 (s, 1H), 8.50 (s, 1H), 7.98 (s, 1H), 7.58 (s, 1H), 7.21-7.35 (m, 6H), 7.06-7.10 (m, 2H), 5.94-5.99 (m, 1H), 5.49 (s, 1H), 4.67-4.76 (m, 2H), 3.64 (d, J = 14.4 Hz, 1H), 3.45 (d, J = 14.4 Hz, 1H), 2.97-3.16 (m, 4H), 2.53-2.66 (m, 2H), 1.91 (d, J = 7.2 Hz, 3H). |
| 63 | 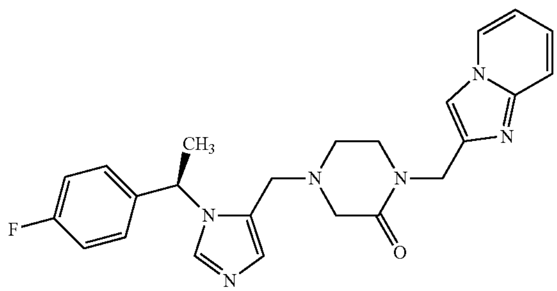 [SMILES: C[C@H](c1ccc(F)cc1)n1cncc1CN1CCN(Cc2cn3ccccc3n2)C(=O)C1] | (R)-4-((1-(1-(4-fluorophenyl)ethyl)-1H-imidazol-5-yl)methyl)-1-(imidazo[1,2-a]pyridin-2-ylmethyl)piperazin-2-one | 433 | CD$_3$OD δ 9.26 (s, 1H), 8.74 (d, J = 6.8 Hz, 1H), 8.15 (s, 1H), 7.87-7.98 (m, 2H), 7.60 (s, 1H), 7.47 (t, J = 14 Hz, 2H), 7.05-7.26 (m, 2H), 7.03 (t, J = 17.2 Hz, 2H), 5.93-5.95 (s, 1H), 4.71-4.80 (m, 2H), 3.68 (d, J = 14.4 Hz, 1H), 3.46 (d, J = 14.4 Hz, 1H), 3.30-3.48 (m, 1H), 3.02-3.22 (m, 3H), 2.60-2.74 (m, 2H), 1.90 (d, J = 7.2 Hz, 3H). |
| 64 | 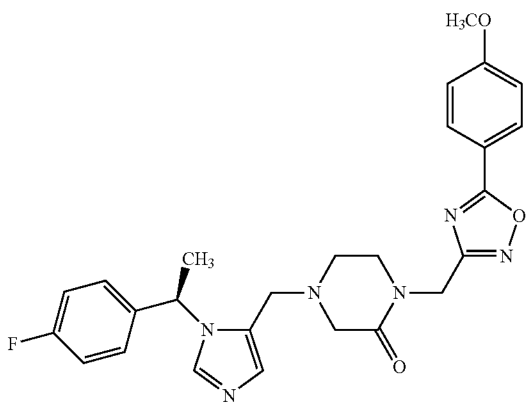 [SMILES: COc1ccc(-c2nc(CN3CCN(Cc4cncn4[C@H](C)c4ccc(F)cc4)CC3=O)no2)cc1] | (R)-4-((1-(1-(4-fluorophenyl)ethyl)-1H-imidazol-5-yl)methyl)-1-((5-(4-methoxyphenyl)-1,2,4-oxadiazol-3-yl)methyl)piperazin-2-one | 491 | CD$_3$OD: δ 9.20 (s, 1H), 8.03 (d, J = 8.8 Hz, 2H), 7.59 (s, 1H), 7.31-7.34 (m, 2H), 7.06-7.22 (m, 4H), 5.98-6.03 (m, 1H), 4.71 (s, 1H), 3.81 (s, 3H), 3.04-3.68 (m, 6H), 2.68-2.80 (m, 2H), 1.92 (d, J = 7.2 Hz, 3H). |

Example 65

(R)-1-((2-((2,4-dimethoxybenzyl)amino)thiazol-5-yl)methyl)-4-((1-(1-(4-fluorophenyl)ethyl)-1H-imidazol-5-yl)methyl)piperazin-2-one (Compound 65)

Step A—Preparation of Int 65-1

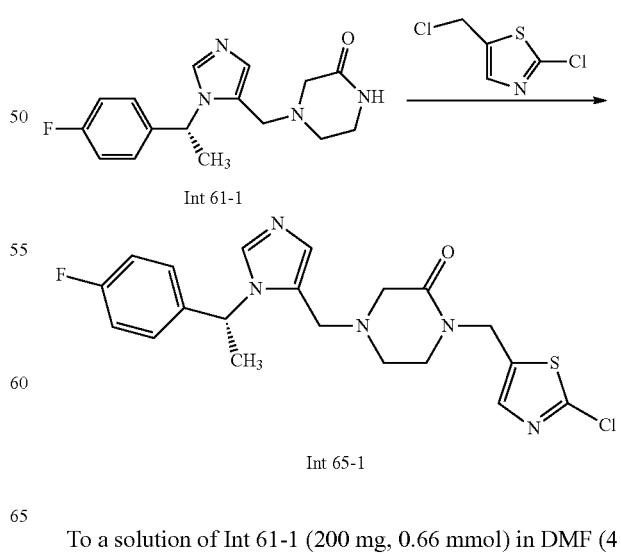

To a solution of Int 61-1 (200 mg, 0.66 mmol) in DMF (4 mL) was added NaH (100 mg, 2.5 mmol, 60% in oil) at 0°

C. and the reaction mixture was stirred at this temperature for 3 h. 2-chloro-5-(chloromethyl)thiazole (110 mg, 0.66 mmol) was added to the reaction and stirring was allowed to continue overnight. The reaction mixture was diluted with water (10 mL) and extracted with EtOAc (3 times). The organic washings were washed with brine (10 mL), dried over $Na_2SO_4$ and concentrated. The residue was purified by column chromatography (Petroleum Ether:EtOAc=10:1) to give Int 65-1 (210 mg) which was used into next step without further purification. $^1$H NMR (CD$_3$OD): δ 9.41 (s, 1H), 7.79 (s, 1H), 7.70 (s, 1H), 7.29-7.33 (m, 2H), 7.11-7.16 (m, 1H), 5.94-6.01 (m, 1H), 5.64 (s, 2H), 3.60 (d, J=16.0 Hz, 1H), 3.42 (d, J=16.0 Hz, 1H), 3.03-3.21 (m, 2H), 3.00 (d, J=16.0 Hz, 1H), 2.90 (d, J=16.0 Hz, 1H), 2.41-2.70 (m, 2H), 1.91 (d, J=7.2 Hz, 3H). MS (ESI): m/z (M+H)$^+$ 433.2, 435.2.

Step B—Preparation of Compound 65

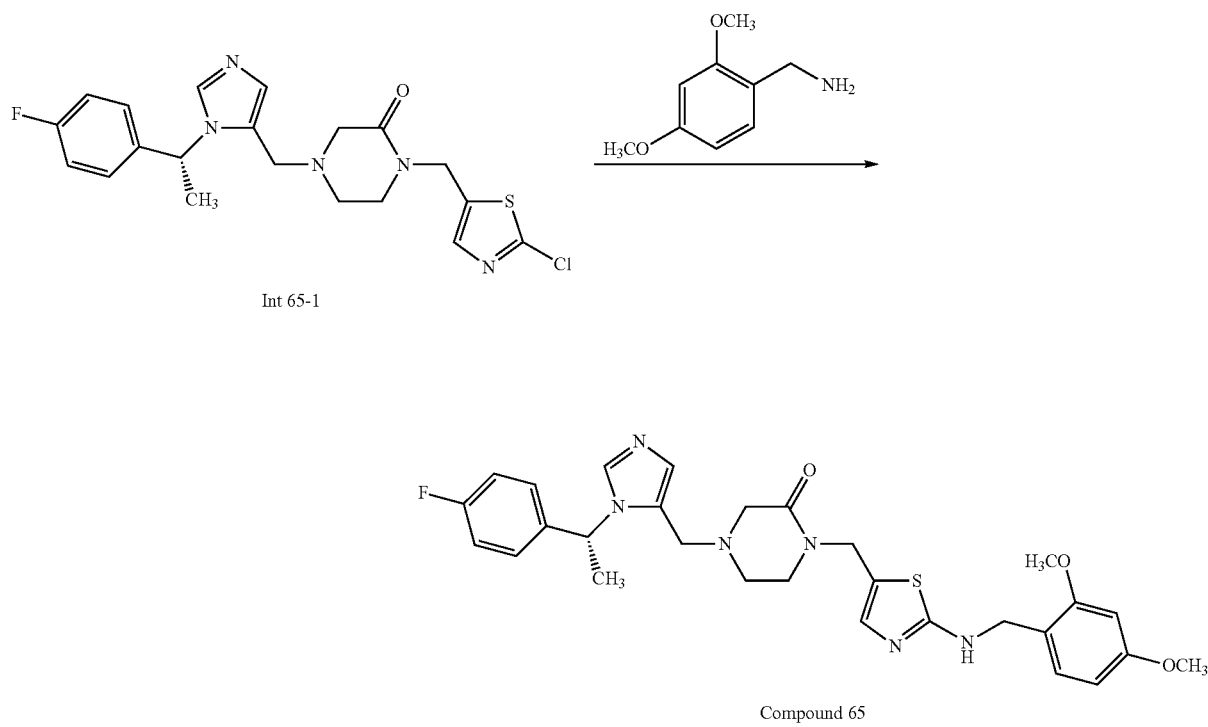

To a solution of compound Int 65-1 (200 mg, 0.46 mmol) in DMF (5 mL) was added $K_2CO_3$ (126 mg, 0.92 mmol) and 2,4-dimethoxybenzylamine piperazine (77 mg, 0.46 mmol). The reaction was stirred at 120° C. overnight before being cooled and filtered. The filtrate was concentrated and the residue was purified by HPLC to give Compound 65. $^1$H NMR (CD3OD): δ 9.27 (s, 1H), 7.59 (s, 1H), 7.36 (m, 2H), 7.20-7.27 (m, 4H), 7.00 (t, J=17.6 Hz, 2H), 6.48-6.57 (m, 2H), 5.88-5.93 (m, 1H), 4.35-4.48 (m, 4H), 3.81 (s, 3H), 3.77 (s, 3H), 3.45-3.70 (m, 1H), 3.42-3.44 (m, 1H), 2.97-3.23 (m, 3H), 2.59-2.65 (m, 2H), 1.90 (d, J=7.2 Hz, 3H). MS (ESI): m/z (M+H)$^+$ 465.2.

The following compounds 66-69 were prepared as described in Example 65.

| Cmpd | Structure | IUPAC name | M + 1 | ¹H NMR |
|---|---|---|---|---|
| 66 | 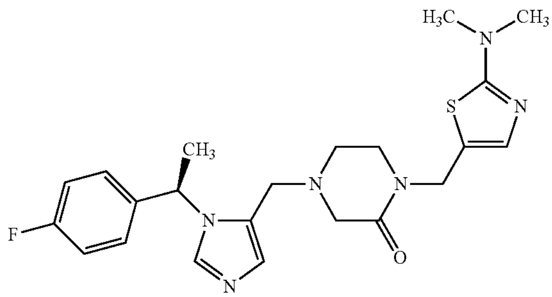 [SMILES: C[C@H](c1ccc(F)cc1)n1cncc1CN1CCN(Cc2cnc(N(C)C)s2)C(=O)C1] | (R)-1-((2-(dimethylamino)thiazol-5-yl)methyl)-4-((1-(1-(4-fluorophenyl)ethyl)-1H-imidazol-5-yl)methyl)piperazin-2-one | 443 | CD$_3$OD: δ 9.27 (s, 1H), 7.59 (s, 1H), 7.36 (m, 2H), 7.23-7.26 (m, 2H), 7.05 (t, J = 17.6 Hz, 2H), 5.89-5.95 (m, 1H), 3.70 (d, J = 14.4 Hz, 1H), 3.45 (d, J = 14.4 Hz, 1H), 2.94-3.26 (m, 9H), 2.59-2.65 (m, 2H), 1.90 (d, J = 7.2 Hz, 3H). |
| 67 | 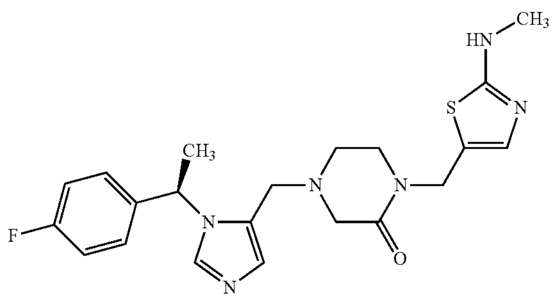 [SMILES: CNc1ncc(CN2CCN(Cc3cncn3[C@H](C)c3ccc(F)cc3)CC2=O)s1] | (R)-4-((1-(1-(4-fluorophenyl)ethyl)-1H-imidazol-5-yl)methyl)-1-((2-(methylamino)thiazol-5-yl)methyl)piperazin-2-one | 429 | CD$_3$OD: δ 9.26 (s, 1H), 7.59 (s, 1H), 7.23-7.29 (m, 3H), 7.02-7.07 (m, 2H), 5.91-5.93 (m, 1H), 4.42-4.44 (m, 2H), 3.68 (d, J = 16.0 Hz, 1H), 3.43 (d, J = 16.0 Hz, 1H), 2.94-3.22 (m, 7H), 2.57-2.67 (m, 2H), 1.91 (d, J = 7.2 Hz, 3H). |
| 68 | 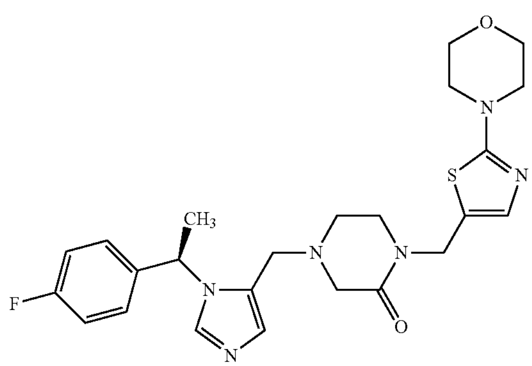 [SMILES: C[C@H](c1ccc(F)cc1)n1cncc1CN1CCN(Cc2cnc(N3CCOCC3)s2)C(=O)C1] | (R)-4-((1-(1-(4-fluorophenyl)ethyl)-1H-imidazol-5-yl)methyl)-1-((2-morpholinothiazol-5-yl)methyl)piperazin-2-one | 485 | CD$_3$OD: δ 9.25 (s, 1H), 7.59 (s, 1H), 7.24-7.27 (m, 3H), 7.03-7.07 (m, 2H), 5.90-5.93 (m, 1H), 4.43-4.51 (m, 2H), 3.43-3.81 (m, 9H), 2.94-3.23 (m, 4H), 2.59-2.66 (m, 2H), 1.91 (d, J = 7.2 Hz, 3H). |
| 69 | 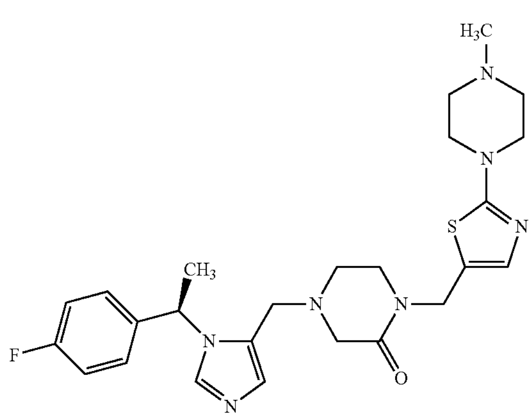 [SMILES: C[C@H](c1ccc(F)cc1)n1cncc1CN1CCN(Cc2cnc(N3CCN(C)CC3)s2)C(=O)C1] | (R)-4-((1-(1-(4-fluorophenyl)ethyl)-1H-imidazol-5-yl)methyl)-1-((2-(4-methylpiperazin-1-yl)thiazol-5-yl)methyl)piperazin-2-one | 498 | CD$_3$OD: δ 9.25 (s, 1H), 7.58 (s, 1H), 7.25-7.28 (m, 2H), 7.19 (s, 1H), 7.04 (t, J = 17.6 Hz, 2H), 5.90-5.95 (m, 1H), 4.45-4.55 (m, 2H), 2.99-3.79 (m, 14H), 3.09 (s, 3H), 2.58-2.66 (m, 2H), 1.89 (d, J = 7.2 Hz, 3H). |

Example 70 ethyl 2-(4-((1-(1-(4'-fluoro-[1,1'-biphenyl]-2-yl)ethyl)-1H-imidazol-5-yl)methyl)piperazin-1-yl)acetate (Compound 70)

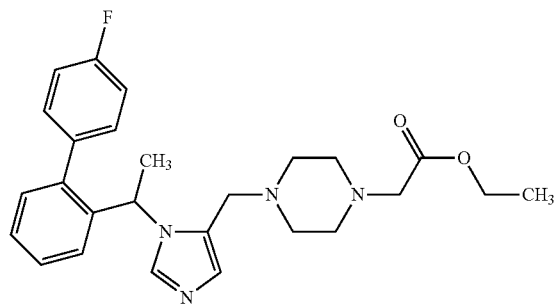 [SMILES: CCOC(=O)CN1CCN(Cc2cncn2C(C)c2ccccc2-c2ccc(F)cc2)CC1]

Step A—Preparation of Int 70-1

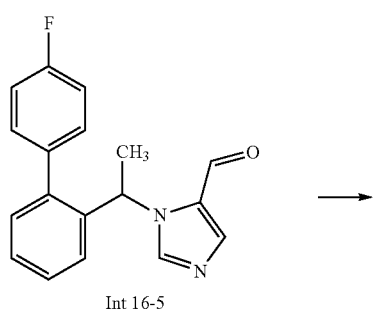

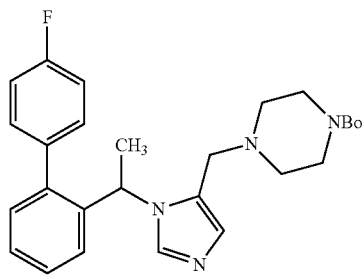

To a solution of Int 16-5 (1.0 g, 3.40 mmol) in DMF (20 mL) was added Et₃N (343 mg, 3.40 mmol), N-Boc-piperazine (200 mg, 0.68 mmol) and Ti(EtO)₄ (2.3 g, 10.20 mmol). The reaction mixture was heated to 80° C. overnight then cooled. NaBH(AcO)₃ (1.4 g, 6.80 mmol) was added at room temperature and the mixture was stirred for another 6 h. The mixture was poured into H₂O (20 mL) and extracted with EtOAc (20 mL×3). The combined organic extracts were washed with aqueous saturated sodium bicarbonate (10 mL) and brine (10 mL), dried over sodium sulfate and concentrated. The crude mixture purified by column chromatography with Petroleum Ether:EtOAc=5:1 to give Int 70-1. ¹H NMR (CDCl₃) δ 7.56 (s, 1H), 7.31-7.33 (m, 2H), 7.06-7.17 (m, 5H), 7.82 (s, 1H), 5.62 (q, J=7.2 Hz, 1H), 3.19 (s, 4H), 2.98 (d, J=14.0 Hz, 1H), 2.85 (d, J=14.0 Hz, 1H), 2.15-2.19 (m, 2H) 2.03-2.09 (m, 2H), 1.69 (d, J=7.2 Hz, 3H), 1.42 (s, 9H). MS (APCI): M/Z (M+1) 465.2.

Step B—Preparation of Int 70-2

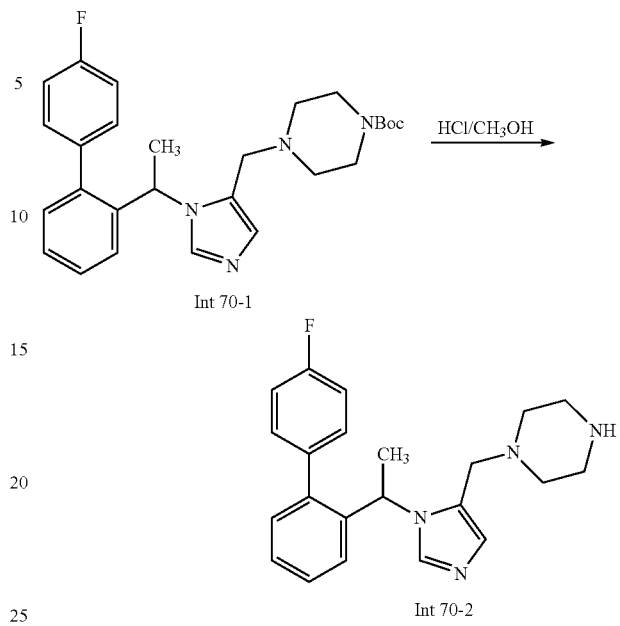

The mixture of Int 70-1 (1.0 g, 2.16 mmol) in 4M HCl/MeOH (4N, 20 mL) was stirred at 0° C. for 3 h. The mixture was concentrated to give Int 70-2 (900 mg) which was used into the next step without further purification. MS (APCI): M/Z (M+1) 365.2.

Step C—Preparation of Compound 70

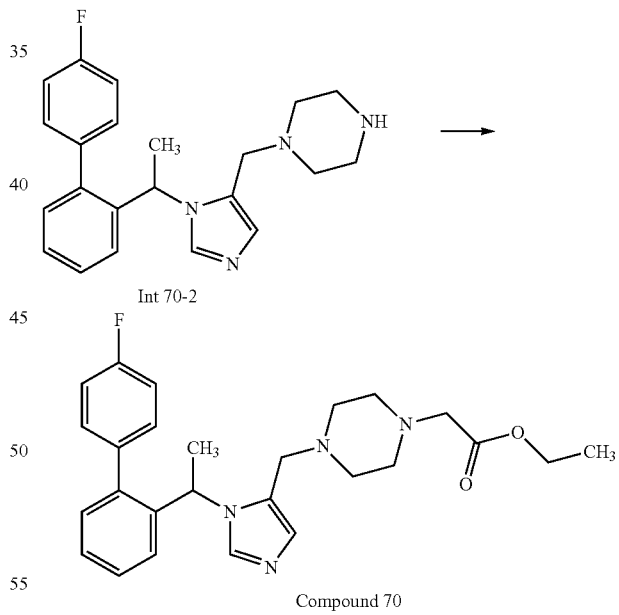

To the solution of Int 70-2 (100 mg, 0.23 mmol) in DMF (3 mL) was added Et₃N (93 mg, 0.92 mmol) and ethyl bromoacetate (0.46 mmol). The mixture was heated at 80° C. overnight. The crude mixture was and purified by HPLC to afford Compound 70 (54 mg). ¹H NMR (CD₃OD): δ 8.91 (s, 1H), 7.42-7.48 (m, 4H), 7.19-7.27 (m, 5H), 5.91 (q, J=7.0 Hz, 1H), 4.28 (q, J=7.2 Hz, 2H), 4.08 (s, 2H), 3.14 (d, J=14.4 Hz, 1H), 2.99 (d, J=14.4 Hz, 1H), 2.46-2.57 (m, 4H), 1.96 (d, J=6.8 Hz, 3H), 1.29 (t, J=7.2 Hz, 3H). MS (ESI): m/z (M+H)⁺ 451.2.

The following compounds 71-72 were prepared as described in Example 70.

| Cmpd | Structure | IUPAC name | M + 1 | ¹H NMR |
|---|---|---|---|---|
| 71 | 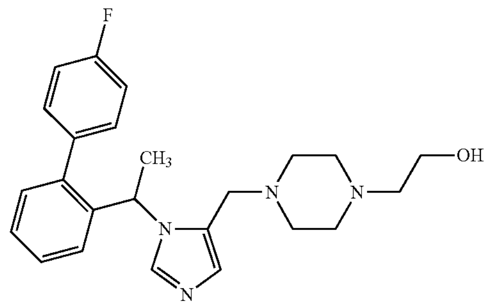 [SMILES: CC(c1ccccc1-c1ccc(F)cc1)n1cncc1CN1CCN(CCO)CC1] | 2-(4-((1-(1-(4'-fluoro-[1,1'-biphenyl]-2-yl)ethyl)-1H-imidazol-5-yl)methyl)piperazin-1-yl)ethanol | 409 | CD$_3$OD: δ 8.91 (s, 1H), 7.42-7.47 (m, 4H), 7.19-7.27 (m, 5H), 5.92 (q, J = 7.0 Hz, 1H), 3.64 (t, J = 4.8 Hz, 2H), 3.47-3.49 (m, 2H), 3.20-3.23 (m, 2H), 3.14 (d, J = 14.4 Hz, 1H), 2.99 (d, J = 14.4 Hz, 1H), 2.50-2.72 (m, 2H), 2.26-2.47 (m, 2H), 1.96 (d, J = 7.2 Hz, 3H). |
| 72 | 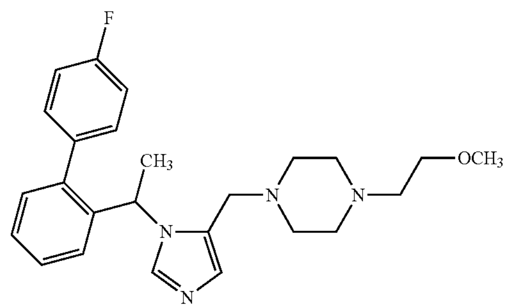 [SMILES: COCCN1CCN(Cc2cncn2C(C)c2ccccc2-c2ccc(F)cc2)CC1] | 1-((1-(1-(4'-fluoro-[1,1'-biphenyl]-2-yl)ethyl)-1H-imidazol-5-yl)methyl)-4-(2-methoxyethyl)piperazine | 423 | CD$_3$OD: δ 8.91 (s, 1H), 7.42-7.48 (m, 4H), 7.19-7.28 (m, 5H), 5.92 (q, J = 7.0 Hz, 1H), 3.67 (t, J = 4.8 Hz, 2H), 3.46 (s, 2H), 3.37 (s, 3H), 3.14 (d, J = 14.4 Hz, 1H), 2.98 (d, J = 14.4 Hz, 1H), 2.90-2.96 (m, 2H), 2.59-2.70 (m, 2H), 2.24-2.34 (m, 2H), 1.96 (d, J = 7.2 Hz, 3H). |

Example 73

Determination of IC$_{50}$ in a Cocktail Assay for CYPs 1A2, 2C9, 2C19, 2D6 and 3A4

This assay was performed in a standard 96-well plate design. IC$_{50}$ values were calculated from the percent inhibition observed for each test compound at 6 concentrations (for example, 0.0032, 0.016, 0.08, 0.4, 2 and 10 μM). The incubation substrate mix contains 10 μM phenacetin (1A2), 5 μM diclofenac (2C9), 30 μM mephenytoin (2C19), 5 μM dextromethorphan (2D6) and 2 μM midazolam (3A4), 0.1 mg/mL protein human liver microsomes (BD Gentest), 1 mM NAPDH, 3.3 mM MgCl$_2$ and 100 mM potassium phosphate buffer (pH 7.4). The production of the metabolite of each probe substrate was determined after incubation for 10 min at 37° C. Quantitation of the metabolite peak area ratio against an internal standard (tolbutamide) was determined by LC/MS/MS analysis following acetonitrile treatment of the incubations.

| Probe Substrate | Reaction (isoform) | Metabolite Detected |
|---|---|---|
| Phenacetin | O-deethylation (CYP1A2) | Acetaminophen |
| Diclofenac | 4'-hydroxylation (CYP2C9) | 4'-Hydroxydiclofenac |
| Mephenytoin | 4'-hydroxylation (CYP2C19) | 4'-Hydroxymephenytoin |
| Dextromethorphan | O-demethylation (CYP2D6) | Dextrorphan |
| Midazolam | 1'-hydroxylation (CYP3A4) | 1'-Hydroxymidazolam |

Samples were analyzed in the MRM mode with a SCIEX API-4000 mass spectrometer (Applied Biosystems, Foster City, Calif.), with a Shimadzu LC-20 AD pump (Shimadzu corporation, Kyoto, JP) and a CTC PAL autosampler (Agilent Technologies, Switzerland). A Phenomenex, Luna, 5 μm, 100 A, 2.00×30 mm HPLC column was used for the separation. The mobile phases were: (A) 0.1% formic acid in water and (B) 0.1% formic acid in acetonitrile. The binary gradient was as follows.

| AutoSampler: CTC PAL | |
|---|---|
| Loop Volume 1 (user entered) | 100 μL |
| Loop Volume 2 (user entered) | 100 μL |
| Actual Injection Volume | 10.0 μL |

| Binary Gradient Total Flow: 700 μL/min | | |
|---|---|---|
| Time (min) | A (%) | B (%) |
| 0.01 | 98 | 2 |
| 0.40 | 30 | 70 |
| 0.80 | 2 | 98 |
| 1.00 | System Controller | Stop |

The mass spectrum parameters were as follows:

| MS Parameters: | |
|---|---|
| CUR Curtain gas (psi): | 20 |
| GS1 Ion source gas1(psi): | 50 |
| GS2 Ion source gas2(psi): | 60 |
| IS IonSpray voltage (V): | 5500 |
| TEM Temperature (° C.): | 600 |
| ihe Interface heater (on/off): | ON |
| CAD Collision Activated Dissociation (psi): | 10 |
| EP Entrance Potential (V): | 10 |
| CXP Collision Cell Exit Potential (V): | 12 |

The LC/MS/MS parameters for the analytes were as follows.

| Compound | Ion Transition Q1 Mass (m/z) | Ion Transition Q3 Mass (m/z) | DP Declustering Potential (V) | CE Collision Energy (V) | RT Retention Time (min) |
| --- | --- | --- | --- | --- | --- |
| Acetaminophen | 152.2 | 110 | 40 | 23 | 0.36 |
| 4'-Hydroxydiclofenac | 312 | 231 | 32 | 29 | 0.72 |
| 4'-Hydroxymephenytoin | 235.3 | 150.3 | 45 | 25 | 0.49 |
| Dextrorphan | 258.2 | 157.2 | 40 | 55 | 0.42 |
| 1'-hydroxymidazolam | 342.2 | 203.2 | 40 | 30 | 0.53 |
| IS | 271.1 | 155.3 | 69 | 25 | 0.71 |

The peak area ratio of the analyte to the internal standard was used to quantify the metabolite. The values of peak area ratios in the presence of test compound were compared to those of maximum or minimum controls and were expressed as % inhibition by interpolating between the maximum and minimum peak area ratios. Incubations with no inhibitor were defined as the maxima.

The following equation was used to calculate the % inhibition:

$$[1-[(X-\text{Low control})/(\text{High control}-\text{Low control})]]*100$$

For the $IC_{50}$ calculation, SigmaPlot was used to plot the mean % inhibition versus the test compound concentrations and for non-linear regression analysis of the data. Depending on the range of data points defining the inhibition curve, the data may have been fit to the 4-parameter logistic equation.

Example 74

The table below provides data for compounds of Formula (I) obtained using the assays described in Example 73, above.

| Cmpd | CYP3A4 | CYP1A2 | CYP2C9 | CYP2C19 | CYP2D6 |
| --- | --- | --- | --- | --- | --- |
| 1 | 20 | >10000 | 7371 | 6222 | >10000 |
| 2 | 18 | >10000 | >10000 | >10000 | >10000 |
| 3 | 37 | >10000 | >10000 | >10000 | 8708 |
| 4 | 58 | >10000 | 3266 | 2675 | >10000 |
| 5 | 15 | 5566 | 3246 | 3738 | 7330 |
| 6 | 27 | >10000 | 5672 | 7921 | 4965 |
| 7 | 21 | >10000 | 8168 | >10000 | 8485 |
| 8 | 22 | 9177 | 2526 | 3254 | 2487 |
| 9 | 21 | >10000 | 2515 | 2270 | 2524 |
| 10 | 17 | >10000 | 2326 | 7020 | 2105 |
| 11 | 21 | 5066 | 2876 | 3307 | 5989 |
| 12 | 50 | 1474 | 5321 | 3982 | 6362 |
| 13 | 10 | >10000 | 4668 | 6397 | >10000 |
| 14 | 17 | 5522 | 2205 | 2602 | 3704 |
| 15 | 16 | 2423 | 1387 | 1246 | 2076 |
| 16 | 18 | >10000 | 7473 | 4269 | 1929 |
| 17 | 29 | >10000 | >10000 | >10000 | 4041 |
| 18 | 29 | >10000 | >10000 | 4792 | >10000 |
| 19 | 50 | >10000 | 1655 | 2419 | 9974 |
| 20 | 35 | >10000 | >10000 | 9911 | >10000 |
| 21 | 35 | >10000 | 4077 | 8705 | 7524 |
| 22 | 26 | >10000 | 1759 | 4689 | 3213 |
| 23 | 7 | >10000 | 4373 | 3160 | 2924 |
| 24 | 11 | >10000 | 3432 | 2263 | 3084 |
| 25 | 28 | >10000 | 9590 | >10000 | 2911 |
| 26 | 21 | >10000 | >10000 | >10000 | 1044 |
| 27 | 9 | >10000 | >10000 | >10000 | 1761 |
| 28 | 10 | >10000 | 3867 | 3568 | 1107 |
| 29 | 20 | >10000 | 2486 | 4973 | 2771 |
| 30 | 7 | >10000 | 5551 | 8402 | 1624 |
| 31 | 7 | >10000 | 2318 | 3740 | 2874 |
| 32 | 24 | >10000 | >10000 | >10000 | >10000 |
| 33 | 35 | >10000 | 6520 | 10000 | 2091 |
| 34 | 8 | >10000 | 10000 | 10000 | 2521 |
| 35 | 4 | >10000 | >10000 | >10000 | >10000 |
| 36 | 45 | >10000 | 6984 | 4255 | 1721 |
| 37 | 8 | >10000 | 4359 | 5385 | 1413 |
| 38 | 31 | >10000 | 6468 | 4721 | 3688 |
| 39 | 23 | >10000 | >10000 | >10000 | 1577 |
| 40 | 27 | >10000 | >10000 | >10000 | 5265 |
| 41 | 30 | >10000 | 2700 | 2230 | 2385 |
| 42 | 22 | >10000 | >10000 | 2397 | 1656 |
| 43 | 50 | >10000 | >10000 | 4012 | 2947 |
| 44 | 29 | >10000 | 5090 | 5842 | >10000 |
| 45a | 12 | >10000 | 7769 | 5499 | >10000 |
| 45b | 20 | >10000 | 3999 | 5181 | >10000 |
| 46 | 46 | >10000 | >10000 | >10000 | >10000 |
| 47 | 20 | >10000 | 9267 | 7829 | >10000 |
| 48 | 31 | >10000 | 1470 | 2001 | 4891 |
| 49 | 14 | >10000 | 1807 | 2114 | >10000 |
| 50a | 16 | >10000 | 4361 | 4331 | 4001 |
| 50b | 5 | >10000 | 1283 | 4403 | >10000 |
| 51 | 22 | >10000 | >10000 | >10000 | >10000 |
| 52a | 7 | >10000 | >10000 | 8488 | >10000 |
| 52b | 27 | >10000 | 6200 | 3672 | >10000 |
| 53 | 13 | >10000 | 6117 | >10000 | 9836 |
| 54 | 14 | >10000 | 2864 | 3346 | >10000 |
| 55 | 10 | >10000 | 2968 | 2389 | 8032 |
| 56 | 35 | >10000 | >10000 | >10000 | 7165 |
| 57 | 5 | >10000 | 2808 | 2643 | 2448 |
| 58 | 7 | >10000 | 2572 | >10000 | >10000 |
| 59 | 9 | >10000 | 6484 | 3362 | 2209 |
| 60 | 23 | >10000 | >10000 | >10000 | 4497 |
| 61 | 23 | >10000 | >10000 | 1625 | 2518 |
| 62 | 43 | 6944 | 6208 | 1144 | 5642 |
| 63 | 46 | 10000 | >10000 | >10000 | >10000 |
| 64 | 43 | 3592 | 2864 | 4523 | 3105 |
| 65 | 10 | >10000 | 8776 | 1344 | 3359 |
| 66 | 43 | >10000 | >10000 | >10000 | >10000 |
| 67 | 75 | >10000 | >10000 | >10000 | >10000 |
| 68 | 80 | >10000 | >10000 | >10000 | >10000 |
| 69 | 56 | >10000 | >10000 | >10000 | >10000 |
| 70 | 15 | >10000 | >10000 | 5952 | 7680 |
| 71 | 37 | >10000 | >10000 | >10000 | >10000 |
| 72 | 14 | >10000 | >10000 | >10000 | 1173 |

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:

1. A compound having the formula (I):

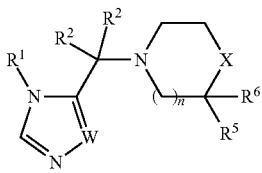

or a pharmaceutically acceptable salt thereof,
wherein:
n is 1;
W is —N= or —CH=;
X is —N($R^3$)—;
$R^1$ is selected from —($C_1$-$C_6$ alkylene)-aryl, —($C_1$-$C_6$ alkylene)-(5 or 6-membered heteroaryl), —($C_1$-$C_6$ alkylene)-O-aryl, —($C_1$-$C_6$ alkylene)-O-(5 or 6-membered heteroaryl) and $C_3$-$C_6$ cycloalkyl, wherein any aryl, heteroaryl or $C_3$-$C_6$ cycloalkyl group can be optionally substituted with up to four $R^9$ groups, which can be the same or different, and wherein said $C_3$-$C_6$ cycloalkyl group can be fused to a benzene ring and said fused benzene ring can be optionally substituted with up to four $R^9$ groups, which can be the same or different;
one occurrence of $R^2$ is H and the other occurrence of $R^2$ is $C_1$-$C_6$ alkyl;
$R^3$ is selected from Y, —O—Y, —C(O)—Y, —($C_1$-$C_6$ alkylene)-Y, —($C_1$-$C_6$ alkylene)-C(O)—Y, —($C_1$-$C_6$ alkylene)-C(O)—O—Y and —($C_1$-$C_6$ alkylene)-O—Y, wherein each Y is independently selected from:
(1) $C_1$-$C_4$ alkyl,
(2) $C_1$-$C_4$ haloalkyl,
(3) $C_1$-$C_4$ hydroxyalkyl,
(4) $C_3$-$C_6$ cyclohaloalkyl,
(5) $C_3$-$C_6$ cycloalkyl,
(6) phenyl, wherein said phenyl group can be optionally substituted with up to four $R^7$ groups,
(7) 5 or 6-membered heteroaryl, wherein said 5 or 6-membered heteroaryl group can be optionally substituted with up to four $R^7$ groups, and
(8) 5 or 6-membered monocyclic heterocycloalkyl or 9 or 10-membered bicyclic heterocycloalkyl, wherein said 5 or 6-membered monocyclic heterocycloalkyl group can optionally form a spirocycle with a $C_3$-$C_6$ cycloalkyl group or another 5 or 6-membered monocyclic heterocycloalkyl group, and wherein said 5 or 6-membered monocyclic heterocycloalkyl group and said 9 or 10-membered bicyclic heterocycloalkyl group can be optionally substituted on one or more ring carbon atoms with up to four $R^7$ groups, which can be the same or different, and wherein a ring carbon atom of a 5 or 6-membered monocyclic heterocycloalkyl group may be functionalized as a carbonyl group;
$R^5$ is selected from H, $C_1$-$C_6$ alkyl, phenyl, —C(O)N($R^8$)$_2$ and —C(O)—Z, wherein Z is selected from piperidinyl, piperazinyl and morpholinyl and wherein said Z is optionally substituted with 1 to 3 halo groups, and phenyl is optionally substituted with —N($R^8$)$_2$,
$R^6$ is H;
each occurrence of $R^7$ and each occurrence of $R^9$ are is independently selected from $C_1$-$C_6$ alkyl, phenyl, benzyl, 5 or 6-membered heteroaryl, —$CH_2$-(5 or 6-membered heteroaryl), 5 or 6-membered heterocycloalkyl, —$CH_2$-(5 or 6-membered heterocycloalkyl), $C_1$-$C_6$ hydroxyalkyl, $C_1$-$C_6$ haloalkyl, halo, —CN, —N($R^8$)$_2$, —($C_1$-$C_6$ alkylene)-N($R^8$)$_2$, —$OR^8$, —C(O)$OR^8$, —$SR^8$, —S(O)$_2R^8$, —C(O)N($R^8$)$_2$, —($C_1$-$C_6$ alkylene)-C(O)$OR^8$, —($C_1$-$C_6$ alkylene)-$SR^8$, —($C_1$-$C_6$ alkylene)-S(O)$_2R^8$ and ($C_1$-$C_6$ alkylene)-C(O)N($R^8$)$_2$, wherein said phenyl, 5 or 6-membered heteroaryl and 5 or 6-membered heterocycloalkyl groups can be optionally substituted with one to three groups selected from $C_1$-$C_6$ alkyl, halo, $C_1$-$C_6$ hydroxyalkyl, $C_1$-$C_6$ haloalkyl, halo, —CN, —N($R^8$)$_2$ and —$OR^8$; and
each occurrence of $R^8$ is independently H, $C_1$-$C_6$ alkyl or benzyl optionally substituted with one or two methoxy groups.

2. The compound of claim 1, having the formula (Ib):

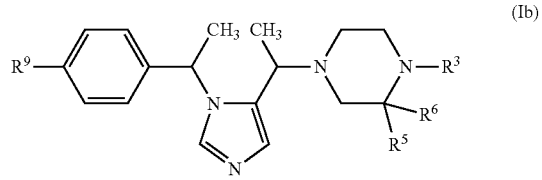

or a pharmaceutically acceptable salt thereof, wherein $R^9$ is present and is F or —CN.

3. The compound of claim 2, or a pharmaceutically acceptable salt thereof, wherein $R^3$ is thiazolyl substituted with —($C_1$-$C_6$ alkylene)-S(O)$_2R^8$, $R^5$ is H, and $R^6$ is H.

4. The compound of claim 2, or a pharmaceutically acceptable salt thereof, wherein $R^3$ is phenyl, $R^5$ is —C(O)—Z, wherein Z is selected from piperidinyl, piperazinyl and morpholinyl and wherein said Z is optionally substituted with 1 to 3 halo groups, and $R^6$ is H.

5. The compound of claim 2, or a pharmaceutically acceptable salt thereof, wherein $R^3$ is —C(O)—Y, Y is selected from (1) cyclobutyl, (2) phenyl, (3) pyridinyl, and (4) tetrahydro-2H-pyran-4-yl; $R^5$ is selected from H, $C_1$-$C_4$ alkyl and phenyl; and $R^6$ is H.

6. The compound of claim 2, or a pharmaceutically acceptable salt thereof, wherein
$R^3$ is selected from $C_1$-$C_6$ hydroxyalkyl, —($C_1$-$C_6$ alkylene)-C(O)—Y, —($C_1$-$C_6$ alkylene)-C(O)—O—Y and —($C_1$-$C_6$ alkylene)-O—Y;
Y is $C_1$-$C_4$ alkyl;
$R^5$ is H; and
$R^6$ is H.

7. A compound selected from the following:
(R)-2-(4-((1-(1-(4-fluorophenyl)ethyl)-1H-imidazol-5-yl)methyl)piperazin-1-yl)benzo[d]oxazole;
(R)-4-(1-(5-((4-(benzo[d]oxazol-2-yl)piperazin-1-yl)methyl)-1H-imidazol-1-yl)ethyl)benzonitrile;
4-(1-(5-((4-(benzo[d]oxazol-2-yl)piperazin-1-yl)methyl)-1H-imidazol-1-yl)cyclopropyl)benzonitrile;
2-(4-((1-(2-isopropoxyethyl)-1H-imidazol-5-yl)methyl)piperazin-1-yl)benzo[d]oxazole;
2-(4-((1-(3-methylbutan-2-yl)-1H-imidazol-5-yl)methyl)piperazin-1-yl)benzo[d]oxazole;
(R)-4-(1-(5-((4-(7-fluorobenzo[d]oxazol-2-yl)piperazin-1-yl)methyl)-1H-imidazol-1-yl)ethyl)benzonitrile;

(R)-4-(1-(5-((4-(7-methylbenzo[d]oxazol-2-yl)piperazin-1-yl)methyl)-1H-imidazol-1-yl)ethyl)benzonitrile;

(R)-4-(1-(5-((4-(6-fluorobenzo[d]oxazol-2-yl)piperazin-1-yl)methyl)-1H-imidazol-1-yl)ethyl)benzonitrile;

(R)-4-(1-(5-((4-(6,7-difluorobenzo[d]oxazol-2-yl)piperazin-1-yl)methyl)-1H-imidazol-1-yl)ethyl)benzonitrile;

2-(4-((1-(1-(tetrahydro-2H-pyran-4-yl)ethyl)-1H-imidazol-5-yl)methyl)piperazin-1-yl)benzo[d]oxazole;

2-(4-((1-(2-(pyridin-2-yl)ethyl)-1H-imidazol-5-yl)methyl)piperazin-1-yl)benzo[d]oxazole;

2-(4-((1-(1-(4-(methylsulfonyl)phenyl)ethyl)-1H-imidazol-5-yl)methyl)piperazin-1-yl)benzo[d]oxazole;

6,7-difluoro-2-(4-((1-(1-(tetrahydro-2H-pyran-4-yl)ethyl)-1H-imidazol-5-yl)methyl)piperazin-1-yl)benzo[d]oxazole;

2-(4-((1-(3,3,3-trifluoro-2-methylpropyl)-1H-imidazol-5-yl)methyl)piperazin-1-yl)benzo[d]oxazole;

2-(4-((1-(4-fluorophenethyl)-1H-imidazol-5-yl)methyl)piperazin-1-yl)benzo[d]oxazole;

(R)-4-(1-(5-((4-(6-methoxybenzo[d]thiazol-2-yl)piperazin-1-yl)methyl)-1H-imidazol-1-yl)ethyl)benzonitrile;

(R)-4-(1-(5-((4-(1H-benzo[d]imidazol-2-yl)piperazin-1-yl)methyl)-1H-imidazol-1-yl)ethyl)benzonitrile;

(R)-5-(ethylsulfonyl)-2-(4-((1-(1-(4-fluorophenyl)propan-2-yl)-1H-imidazol-5-yl)methyl)piperazin-1-yl)thiazole;

(R)-5-(2-(ethylsulfonyl)ethyl)-2-(4-((1-(1-(4-fluorophenyl)propan-2-yl)-1H-imidazol-5-yl)methyl)piperazin-1-yl)thiazole;

(R)-2-(4-((1-(1-(4-chlorophenyl)ethyl)-1H-imidazol-5-yl)methyl)piperazin-1-yl)-5-(2-(ethylsulfonyl)ethyl)thiazole;

(R)-2-(4-((1-(1-(4-fluorophenyl)ethyl)-1H-imidazol-5-yl)methyl)piperazin-1-yl)-5-(2-(ethylsulfonyl)ethyl)thiazole;

N-(tert-butyl)-4-((1-((R)-1-(4-cyanophenyl)ethyl)-1H-imidazol-5-yl)methyl)-1-phenylpiperazine-2-carboxamide;

4-((1R)-1-(5-((4-phenyl-3-(piperidine-1-carbonyl)piperazin-1-yl)methyl)-1H-imidazol-1-yl)ethyl)benzonitrile;

4-((1R)-1-(5-((3-(morpholine-4-carbonyl)-4-phenylpiperazin-1-yl)methyl)-1H-imidazol-1-yl)ethyl)benzonitrile;

4-((1R)-1-(5-((3-(4,4-difluoropiperidine-1-carbonyl)-4-phenylpiperazin-1-yl)methyl)-1H-imidazol-1-yl)ethyl)benzonitrile;

((S)-4-((1-((R)-1-(4-fluorophenyl)ethyl)-1H-imidazol-5-yl)methyl)-1-phenylpiperazin-2-yl)(piperidin-1-yl)methanone;

(4-((1-((R)-1-(4-fluorophenyl)ethyl)-1H-imidazol-5-yl)methyl)-2-phenylpiperazin-1-yl)(5-methylisoxazol-3-yl)methanone;

(4-((1-((R)-1-(4-fluorophenyl)ethyl)-1H-imidazol-5-yl)methyl)-2-phenylpiperazin-1-yl)(phenyl)methanone;

1-(4-((1-((R)-1-(4-fluorophenyl)ethyl)-1H-imidazol-5-yl)methyl)-2-phenylpiperazin-1-yl)ethanone;

(4-((1-((R)-1-(4-fluorophenyl)ethyl)-1H-imidazol-5-yl)methyl)-2-phenylpiperazin-1-yl)(tetrahydro-2H-pyran-4-yl)methanone;

(4-((1-((R)-1-(4-fluorophenyl)ethyl)-1H-imidazol-5-yl)methyl)-2-phenylpiperazin-1-yl)(pyridin-2-yl)methanone;

(4-((1-((R)-1-(4-fluorophenyl)ethyl)-1H-imidazol-5-yl)methyl)-2,6-dimethylpiperazin-1-yl)(1-methylcyclopropyl)methanone;

(2-(tert-butyl)-4-((1-((R)-1-(4-fluorophenyl)-1H-imidazol-5-yl)methyl)piperazin-1-yl)(phenyl)methanone;

(2,6-dimethyl-4-((1-(1-(tetrahydro-2H-pyran-4-yl)ethyl)-1H-imidazol-5-yl)methyl)piperazin-1-yl)(1-methylcyclopropyl)methanone;

(2-(4-(dimethylamino)phenyl)-4-((1-((R)-1-(4-fluorophenyl)-1H-imidazol-5-yl)methyl)piperazin-1-yl)(1-methylcyclopropyl)methanone;

4-((1R)-1-(5-((4-(3,3-difluorocyclobutanecarbonyl)-3,5-dimethylpiperazin-1-yl)methyl)-1H-imidazol-1-yl)ethyl)benzonitrile;

(4-((1-(1-(4'-fluoro-[1,1'-biphenyl]-2-yl)ethyl)-1H-imidazol-5-yl)methyl)piperazin-1-yl)(phenyl)methanone;

1-(4-((1-(1-(4'-fluoro-[1,1'-biphenyl]-2-yl)ethyl)-1H-imidazol-5-yl)methyl)piperazin-1-yl)ethanone;

(R)-1-benzyl-4-((1-(1-(4-fluorophenyl)ethyl)-1H-imidazol-5-yl)methyl)piperazin-2-one;

(R)-1-(2-((1H-1,2,4-triazol-1-yl)methyl)benzyl)-4-((1-(1-(4-fluorophenyl)ethyl)-1H-imidazol-5-yl)methyl)piperazin-2-one;

(R)-4-((1-(1-(4-fluorophenyl)ethyl)-1H-imidazol-5-yl)methyl)-1-(imidazo[1,2-a]pyridin-2-ylmethyl)piperazin-2-one;

(R)-4-((1-(1-(4-fluorophenyl)ethyl)-1H-imidazol-5-yl)methyl)-1-((5-(4-methoxyphenyl)-1,2,4-oxadiazol-3-yl)methyl)piperazin-2-one;

(R)-1-((2-((2,4-dimethoxybenzyl)amino)thiazol-5-yl)methyl)-4-((1-(1-(4-fluorophenyl)ethyl)-1H-imidazol-5-yl)methyl)piperazin-2-one;

(R)-1-((2-(dimethylamino)thiazol-5-yl)methyl)-4-((1-(1-(4-fluorophenyl)ethyl)-1H-imidazol-5-yl)methyl)piperazin-2-one;

(R)-4-((1-(1-(4-fluorophenyl)ethyl)-1H-imidazol-5-yl)methyl)-1-((2-(methylamino)thiazol-5-yl)methyl)piperazin-2-one;

(R)-4-((1-(1-(4-fluorophenyl)ethyl)-1H-imidazol-5-yl)methyl)-1-((2-morpholinothiazol-5-yl)methyl)piperazin-2-one;

(R)-4-((1-(1-(4-fluorophenyl)ethyl)-1H-imidazol-5-yl)methyl)-1-((2-(4-methylpiperazin-1-yl)thiazol-5-yl)methyl)piperazin-2-one;

ethyl 2-(4-((1-(1-(4'-fluoro-[1,1'-biphenyl]-2-yl)ethyl)-1H-imidazol-5-yl)methyl)piperazin-1-yl)acetate;

2-(4-((1-(1-(4'-fluoro-[1,1'-biphenyl]-2-yl)ethyl)-1H-imidazol-5-yl)methyl)piperazin-1-yl)ethanol; and 1-((1-(1-(4'-fluoro-[1,1'-biphenyl]-2-yl)ethyl)-1H-imidazol-5-yl)methyl)-4-(2-methoxyethyl)piperazine;

or a pharmaceutically acceptable salt thereof.

8. A pharmaceutical composition comprising an effective amount of a compound of claim 1, and a pharmaceutically acceptable carrier.

* * * * *